United States Patent
Zhu et al.

(10) Patent No.: US 11,060,094 B2
(45) Date of Patent: Jul. 13, 2021

(54) COMPOSITIONS AND METHODS FOR THE TREATMENT OF COMPLICATIONS AND DISORDERS RELATING TO VON WILLEBRAND FACTOR

(71) Applicant: BAND THERAPEUTICS, LLC, Belmont, MA (US)

(72) Inventors: Shuhao Zhu, Concord, MA (US); James C. Gilbert, Bethlehem, CT (US)

(73) Assignee: BAND THERAPEUTICS, LLC, Belmont, MA (US)

( * ) Notice: Subject to any disclaimer, the term of this patent is extended or adjusted under 35 U.S.C. 154(b) by 89 days.

(21) Appl. No.: 16/613,853

(22) PCT Filed: May 18, 2018

(86) PCT No.: PCT/US2018/033376
§ 371 (c)(1),
(2) Date: Nov. 15, 2019

(87) PCT Pub. No.: WO2018/213697
PCT Pub. Date: Nov. 22, 2018

(65) Prior Publication Data
US 2020/0165612 A1    May 28, 2020

Related U.S. Application Data

(60) Provisional application No. 62/638,579, filed on Mar. 5, 2018, provisional application No. 62/508,530, filed on May 19, 2017.

(51) Int. Cl.
| | |
|---|---|
| *C12N 15/115* | (2010.01) |
| *A61P 7/06* | (2006.01) |
| *A61P 7/02* | (2006.01) |
| *A61P 9/10* | (2006.01) |
| *A61K 9/00* | (2006.01) |

(52) U.S. Cl.
CPC .......... *C12N 15/115* (2013.01); *A61K 9/0019* (2013.01); *A61P 7/02* (2018.01); *A61P 7/06* (2018.01); *A61P 9/10* (2018.01); *C12N 2310/16* (2013.01); *C12N 2310/316* (2013.01); *C12N 2310/317* (2013.01); *C12N 2310/321* (2013.01); *C12N 2310/351* (2013.01); *C12N 2310/3521* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 7,566,701 B2 | 7/2009 | Diener | |
| 2009/0170793 A1* | 7/2009 | Gaur | A61P 43/00 514/44 R |
| 2018/0305695 A1 | 10/2018 | Hirao et al. | |

FOREIGN PATENT DOCUMENTS

| | | |
|---|---|---|
| WO | 2008/150495 A2 | 12/2008 |
| WO | 2010/091396 A2 | 8/2010 |
| WO | 2010091396 | 8/2010 |
| WO | 2017/073536 A1 | 5/2017 |

OTHER PUBLICATIONS

Reinstein, O. et al. "Engineering a Structure Switching Mechanism into a Steroid-Binding Aptamer and Hydrodynamic Analysis of the Ligand Binding Mechanism" (2011) Biochemistry 50:9368-9376.
Extended European Search Report dated Jan. 22, 2021in corresponding European patent application No. 18801554.9 entitled Compositions and Methods for the Treatment of Complications and Disorders Relating to Von Willebrand Factor.
Search Report and Written Opinion dated Mar. 29, 2021 in corresponding Singapore application No. 11201909151Y entitled Compositions and Methods for the Treatment of Complications and Disorders Relating to Von Willebrand Factor.
Matsunaga, K.-i. et al, "High-Affinity DNA Aptamer Generation Targeting von Willebrand Factor A1-Domain by Genetic Alphabet Expansion for Systematic Evolution of Ligands by Exponential Enrichment Using two Types of Libraries Composed of Five Different Bases" (20174) J. of the American Chemical Society 139(1):324-334.
Genbank Accession No. AC106539 "Rattus norvegicus clone CH230-214G17, Working Draft Sequence, 4 unordered Pieces" May 13, 2003, [online]. [Retrieved on Sep. 17, 2018]. <URL: https://www.ncbi.nlm.nih.gov/nuccore/AC106539>.
International Search Report and Written Opinion dated Oct. 2, 2018 in corresponding application PCTUS2018033376 entitled, "Compositions and Methods for the Treatment of Complications and Disorders Relating to Von Willebrand Factor".
Blackshear, J.L. et al., Indices of von Willebrand Factor as Biomarkers of Aortic Stenosis Severity: (From the Biomarkers of Aortic Stenosis Severity [BASS] Study) (2013) Am J Cardiol. 111(3):374-381.
Capoccia, M. et al., "Recurrent Early Thrombus Formation in HeartMate II Left Ventricular Assist Device" (2013) Journal of Investigative Medicine High Impact Case Reports 3 pgs.
Chen, J. et al., "The rate of hemolysis in sickle cell disease correlates with the quantity of active vonWillebrand factor in the plasma" (2011) Blood 117(13):3680-3683.
Couffinhal, T. et al., "Mouse Models to Study Angiogenesis, Vasculogenesis and Arteriogenesis in the Context of Cardiovascular Diseases" (2009) Frontiers in bioscience: a journal and virtual library 14:3310-3325.

(Continued)

*Primary Examiner* — Tracy Vivlemore
(74) *Attorney, Agent, or Firm* — DT Ward, PC; Donna T. Ward; Lingyun Jia

(57) ABSTRACT

The present invention provides VWF protective agents, including aptamers and antibodies for the treatment and or amelioration of complications or disorders arising from aberrant binding or function of VWF.

38 Claims, 4 Drawing Sheets

Specification includes a Sequence Listing.

(56) References Cited

OTHER PUBLICATIONS

Couffinhal, T. et al., "Mouse Model of Angiogenesis" (1998) American Journal of Pathology 152(6):1667-1679.
De Maistre, E. et al., "Performance of two new automated assays for measuring von Willebrand activity: HemosIL AcuStar and Innovance" (2014) Thrombosis and Haemostasis 112: 6 pgs.
De Mast, Q. et al., "ADAMTS13 Deficiency with Elevated Levels of Ultra-Large and Active von Willebrand Factor in P. falciparum and P. vivax Malaria" (2009) Am. J. Trop. Med. Hyg., 80(3):492-498.
Diener, J.L. et al., "Inhibition of von Willebrand factor-mediated platelet activation and thrombosis by the anti-von Willebrand factor A1-domain aptamer ARC1779" (2009) Journal of Thrombosis and Haemostasis 7:1155-1162.
Firbas, C. et al., "Targeting von Willebrand factor and platelet glycoprotein Ib receptor" (2010) Expert Rev. Cardiovasc. Ther. 8(12):1689-1701.
Flannery, C.J., "Thrombus Formation Under High Shear in Arterial Stenotic Flow" (2005) Thesis—Georgia Institute of Technology 176 pgs.
Fraser, K.H. et al., "Computational Fluid Dynamics Analysis of Thrombosis Potential in Left Ventricular Assist Device Drainage Cannulae" (2010) ASAIO J. 56(3): 157-163.
Fu, H. et al., "Flow-induced elongation of von Willebrand factor precedes tension-dependent activation" (2017) Nature Communications 8:324 12 pgs.
Gragnano, F. et al., "Von Willebrand factor as a novel player in valvular heart disease: from bench to valve replacement" (2017) Angiology 69(2):103-112.
Heilmann, C. et al., "Haemolysis in patients with ventricular assist devices: major differences between systems" (2009) European Journal of Cardio-thoracic Surgery 36:580-584.
Hemker, H.C. et al., "Thrombin generation, a function test of the haemostaticthrombotic system" (2006) Thromb Haemost 96: 553-561.
Hollestelle, M.J. et al., "von Willebrand factor propeptide in malaria: evidence of acute endothelial cell activation" (2006) British Journal of Haematology 133:562-569.
Huang, R.-H. et al., "A Structural Explanation for the Antithrombotic Activity of ARC1172, a DNA Aptamer that Binds ion Willebrand Factor Domain A1" (2009) Structure 17:1476-1484.
Ingram, D.A. et al., "Identification of a novel hierarchy of endothelial progenitor cells using human peripheral and umbilical cord blood" (2004) Blood 104(9):2752-2760.
Islam, S. et al., "Left Ventricular Assist Devices and Gastrointestinal Bleeding: A Narrative Review of Case Reports and Case Series" (2013) Clin. Cardiol. 36(4):190-200.
Jilma-Stohlawetz, P. et al., "A dose ranging phase I/II trial of the von Willebrand factor inhibiting aptamer ARC1779 in patients with congenital thrombotic thrombo—cytopenic purpura" (2011) Thromb Haemost 106:539-547.
Jilma-Stohlawetz, P. et al., "Inhibition of von Willebrand factor by ARC1779 in patients with acute thrombotic hrombocytopenic purpura" (2011) Thromb Haemost 105:545-552.
Jilma-Stohlawetz, P. et al., "The anti-von Willebrand factor aptamer ARC1779 increases von Willebrand factor levels and platelet counts in patients with type 2B von Willebrand disease" (2012) Thromb Haemost 108(02): 284-290.

Lawrie, A.S. et al., "A comparative evaluation of a new automated assay for von Willebrand factor activity" (2013) Haemophilia 19:338-342.
Le Behot, A. et al., "Gplbα-VWF blockade restores vessel patency by dissolving platelet aggregates formed under very high shear rate in mice" (2014) Blood 123(21): 3354-3363.
Levin, T., "Design of a High Shear Stress Experiment" (2010) Studienarbeit (Minor Thesis) 105 pgs.
Maeda, M. et al., "FK419, a nonpeptide platelet glycoprotein IIb/IIIa antagonist, ameliorates brain infarction associated with thrombotic focal cerebral ischemia in monkeys: comparison with tissue plasminogen activator" (2005) Journal of Cerebral Blood Flow & Metabolism 25:108-118.
Montgomery, R.R. "The heads and the tails of malaria and VWF" (2016) Blood 127(9):1081-1082.
Nishio, K. et al., "Binding of platelet glycoprotein Ibα to von Willebrand factor domain A1 stimulates the cleavage of the adjacent domain A2 by ADAMTS13" (2001) PNAS 101(29):10578-10583.
Randi, A.M. et al., "Von Willebrand Factor, Angiodysplasia and Angiogenesis" (2013) Mediterr J Hematol Infect Dis 5 (1): e2013060.
Rothenburger, M. et al., "Treatment of Thrombus Formation Associated With the MicroMed DeBakey VAD Using Recombinant Tissue Plasminogen Activator" (2002) 106:I189-I192.
Schneider, S.W. et al., "Shear-induced unfolding triggers adhesion of von Willebrand factor fibers" (2007) PNAS 104(19):7899-7903.
Schoergenhofer, C. et al., "The use of frozen plasma samples in thromboelastometry" (2017) Clin Exp Med 9 pgs.
Shim, K. et al., "Platelet-VWF complexes are preferred substrates of ADAMTS13 under fluid shear stress" (2007) Blood 111(2):651-657.
Siediecki, C.A. et al., "Shear-dependent changes in the three-dimensional structure of human von Willebrand factor" (1996) Blood 88(8):2939-2950.
Siller-Matula, J.M. et al., "ARC15105 Is a Potent Antagonist of Von Willebrand Factor Mediated Platelet Activation and Adhesion" (2012) Arterioscler Thromb Vasc Biol 32:902-909.
Starke, R.D. et al., "Endothelial von Willebrand factor regulates angiogenesis" (2011) Blood 117(3):1071-1080.
Starling, R.C. et al., "Unexpected Abrupt Increase in Left Ventricular Assist Device Thrombosis" (2013/2014) The New England Journal of Medicine 370:33-40.
Starling, R.C. et al., "Supplement to: Starling RC, Moazami N, Silvestry SC, et al. Unexpected abrupt increase in left ventricular assist device thrombosis." (2013/2014) N Engl J Med 51 pgs.
Suarez, J. et al., "Mechanisms of Bleeding and Approach to Patients With Axial-Flow Left Ventricular Assist Devices" (2011) Circ Heart Fail. 4:779-784.
Varga-Szabo, D. et al., "Cell Adhesion Mechanisms in Platelets" (2008) Arterioscler Thromb Vac Biol 28:403-412.
Vaz, A. et al., "Syndrome de Heyde—Associação entre estenose acirtica e hemorragia gastrointestinal [23]" (2010) Rev Port Cardiol 29(02):309-314.
Vincentelli, A. et al., "Acquired von Willebrand Syndrome in Aortic Stenosis" (2003) New Engl J Med 349:343-349.
Zheng, Y. et al., "In vitro microvessels for the study of angiogenesis and thrombosis" (2012) PNAS 109 (24):9342-9347.
Zheng, Y. et al., "Flow-driven assembly of VWF fibres and webs in in vitro microvessels" (2015) Nature Communications 6:7858 11 pgs.

* cited by examiner

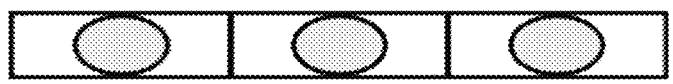
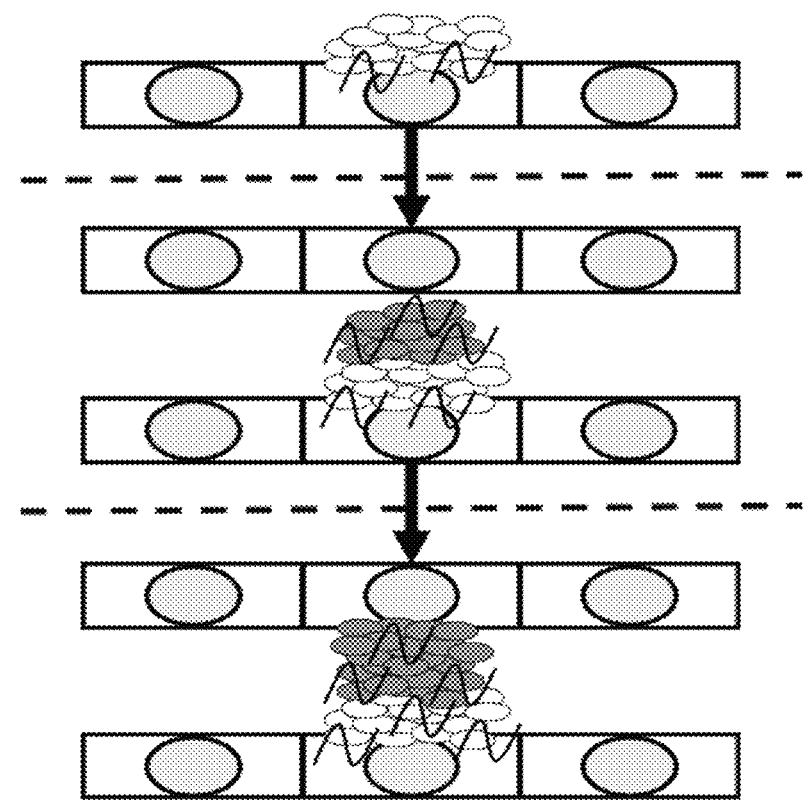
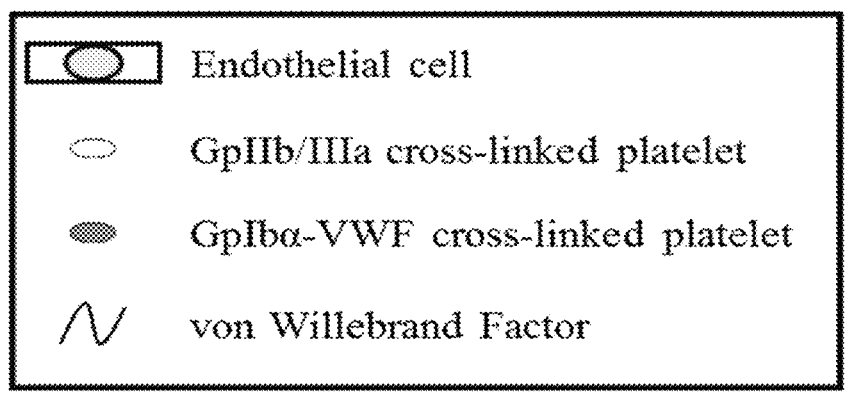

SEQUENCE LISTING

<160> NUMBER OF SEQ ID NOS: 12

<210> SEQ ID NO 1
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gccagggacc uaagacacau gucccuggc                                          29

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(29)
<223> OTHER INFORMATION: 2'-O-Methyl nucleotide
<220> FEATURE:
<221> NAME/KEY: modified_base
<222> LOCATION: (30)..(30)
<223> OTHER INFORMATION: Inverted nucleotide

<400> SEQUENCE: 2
gccagggacc uaagacacau gucccuggct                                         30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(29)
<223> OTHER INFORMATION: 2'-O-Methyl nucleotide
<220> FEATURE:
<221> NAME/KEY: modified_base
<222> LOCATION: (30)..(30)
<223> OTHER INFORMATION: Inverted nucleotide

<400> SEQUENCE: 3
gccagggacc uaagacacau gucccuggct                                         30

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
acaugugucu uaggucccug gc                                                 22

<210> SEQ ID NO 5
<211> LENGTH: 23

-continued

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(22)
<223> OTHER INFORMATION: 2'-O-Methyl nucleotide
<220> FEATURE:
<221> NAME/KEY: modified_base
<222> LOCATION: (23)..(23)
<223> OTHER INFORMATION: Inverted nucleotide

<400> SEQUENCE: 5
acaugugucu uaggucccug gct                                             23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(21)
<223> OTHER INFORMATION: 2'-O-Methyl nucleotide
<220> FEATURE:
<221> NAME/KEY: modified_base
<222> LOCATION: (22)..(22)
<223> OTHER INFORMATION: Inverted nucleotide

<400> SEQUENCE: 6
gggaccuaag acacaugucc ct                                              22

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(4)
<223> OTHER INFORMATION: 2'-O-Methyl nucleotide
<220> FEATURE:
<221> NAME/KEY: modified_base
<222> LOCATION: (8)..(18)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: modified_base
<222> LOCATION: (27)..(28)
```

```
<223> OTHER INFORMATION: 2'-O-Methyl nucleotide
<220> FEATURE:
<221> NAME/KEY: modified_base
<222> LOCATION: (30)..(30)
<223> OTHER INFORMATION: 2'-O-Methyl nucleotide
<220> FEATURE:
<221> NAME/KEY: modified_base
<222> LOCATION: (33)..(34)
<223> OTHER INFORMATION: 2'-O-Methyl nucleotide
<220> FEATURE:
<221> NAME/KEY: modified_base
<222> LOCATION: (36)..(39)
<223> OTHER INFORMATION: 2'-O-Methyl nucleotide
<220> FEATURE:
<221> NAME/KEY: modified_base
<222> LOCATION: (40)..(40)
<223> OTHER INFORMATION: Inverted nucleotide

<400> SEQUENCE: 7
gcgugcagug ccuucggccg tgcggtgccu ccgucacgct                              40

<210> SEQ ID NO 8
<211> LENGTH: 8833
<212> TYPE: DNA
<213> ORGANISM: Homo sapiens

<400> SEQUENCE: 8
agctcacagc tattgtggtg ggaaagggag ggtggttggt ggatgtcaca gcttgggctt        60
tatctccccc agcagtgggg actccacagc ccctgggcta cataacagca agacagtccg       120
gagctgtagc agacctgatt gagcctttgc agcagctgag agcatggcct agggtgggcg       180
gcaccattgt ccagcagctg agtttcccag ggaccttgga gatagccgca gccctcattt       240
gcagggaaag atgattcctg ccagatttgc cggggtgctg cttgctctgg ccctcatttt       300
gccagggacc ctttgtgcag aaggaactcg cggcaggtca tccacggccc gatgcagcct       360
tttcggaagt gacttcgtca acacctttga tgggagcatg tacagctttg cgggatactg       420
cagttacctc ctggcagggg gctgccagaa acgctccttc tcgattattg gggacttcca       480
gaatggcaag agagtgagcc tctccgtgta tcttggggaa ttttttgaca tccatttgtt       540
tgtcaatggt accgtgacac agggggacca aagagtctcc atgccctatg cctccaaagg       600
gctgtatcta gaaactgagg ctgggtacta caagctgtcc ggtgaggcct atggctttgt       660
ggccaggatc gatggcagcg gcaactttca gtcctgctg tcagacagat acttcaacaa        720
gacctgcggg ctgtgtggca actttaacat ctttgctgaa gatgacttta tgacccaaga       780
agggaccttg acctcggacc cttatgactt tgccaactca tgggctctga gcagtggaga       840
acagtggtgt gaacgggcat ctcctcccag cagctcatgc aacatctcct ctgggggaaat     900 gcagaagggc ctgtgggagc agtgccagct tctgaagagc acctcggtgt ttgcccgctg      960 ccacccctg gtggacccg agcctttgt ggccctgtgt gagaagactt tgtgtgagtg        1020
tgctgggggg ctggagtgcg cctgccctgc cctcctggag tacgcccgga cctgtgccca      1080
ggagggaatg gtgctgtacg gctggaccga ccacagcgcg tgcagcccag tgtgccctgc     1140
tggtatggag tataggcagt gtgtgtcccc ttgcgccagg acctgccaga gcctgcacat      1200
caatgaaatg tgtcaggagc gatgcgtgga tggctgcagc tgccctgagg acagctcct     1260 ggatgaaggc ctctgcgtgg agagcaccga gtgtccctgc gtgcattccg gaaagcgcta      1320 cccctcccggc acctccctct ctcgagactg caacacctgc atttgccgaa acagccagtg    1380
gatctgcagc aatgaagaat gtccagggga gtgccttgtc acaggtcaat cacacttcaa     1440
gagctttgac aacagatact tcaccttcag tgggatctgc cagtacctgc tggccgggga     1500
```

```
ttgccaggac cactccttct ccattgtcat tgagactgtc cagtgtgctg atgaccgcga    1560
cgctgtgtgc acccgctccg tcaccgtccg gctgcctggc ctgcacaaca gccttgtgaa    1620
actgaagcat ggggcaggag ttgccatgga tggccaggac gtccagctcc ccctcctgaa    1680
aggtgacctc cgcatccagc atacagtgac ggcctccgtg cgcctcagct acggggagga    1740
cctgcagatg gactgggatg ccgcgggag gctgctggtg aagctgtccc ccgtctatgc     1800
```

```
agtgtgtgag gtggctggcc ggcgttttgc ctcaggaaag aaagtcacct tgaatcccag    3900
tgaccctgag cactgccaga tttgccactg tgatgttgtc aacctcacct gtgaagcctg    3960
ccaggagccg ggaggcctgg tggtgcctcc cacagatgcc ccggtgagcc caccactct     4020
gtatgtggag gacatctcgg aaccgccgtt gcacgatttc tactgcagca ggctactgga    4080
cctggtcttc ctgctggatg ctcctccag gctgtccgag gctgagtttg aagtgctgaa     4140
ggcctttgtg gtggacatga tggagcggct gcgcatctcc cagaagtggg tccgcgtggc    4200
cgtggtggag taccacgacg gctcccacgc ctacatcggg ctcaaggacc ggaagcgacc    4260
gtcagagctg cggcgcattg ccagccaggt gaagtatgcg ggcagccagg tggcctccac    4320
cagcgaggtc ttgaaataca cactgttcca aatcttcagc aagatcgacc gccctgaagc    4380
ctcccgcatc accctgctcc tgatggccag ccaggagccc aacggatgt cccgaacctt     4440
tgtccgctac gtccagggcc tgaagaagaa gaaggtcatt gtgatcccgg tgggcattgg    4500
gccccatgcc aacctcaagc agatccgcct catcgagaag caggcccctg agaacaaggc    4560
cttcgtgctg agcagtgtgg atgagctgga gcagcaaagg gacgagatcg ttagctacct    4620
ctgtgacctt gccccctgaag ccctcctcc tactctgccc ccgacatgg cacaagtcac    4680
tgtgggcccg ggctcttgg gggtttcgac cctggggccc aagaggaact ccatggttct     4740
ggatgtggcg ttcgtcctgg aaggatcgga caaaattggt gaagccgact tcaacaggag    4800
caaggagttc atggaggagg tgattcagcg gatggatgtg gccaggaca gcatccacgt     4860
cacggtgctg cagtactcct acatggtgac tgtggagtac cccttcagcg aggcacagtc    4920
caaaggggac atcctgcagc gggtgcgaga gatccgctac cagggcggca acaggaccaa    4980
cactgggctg gccctgcggt acctctctga ccacagcttc ttggtcagcc agggtgaccg    5040
ggagcaggcg cccaacctgg tctacatggt caccggaaat cctgcctctg atgagatcaa    5100
gaggctgcct ggagacatcc aggtggtgcc cattggagtg ggccctaatg ccaacgtgca    5160
ggagctggaa aggattggct ggcccaatgc ccctatcctc atccaggact ttgagacgct    5220
ccccccgagag gctcctgacc tggtgctgca gaggtgctgc tccggagagg ggctgcagat    5280
ccccaccctc tcccctgcac ctgactgcag ccagcccctg gacgtgatcc ttctcctgga    5340
tggctcctcc agtttcccag cttcttattt tgatgaaatg aagagtttcg ccaaggcttt    5400
catttcaaaa gccaatatag ggcctcgtct cactcaggtg tcagtgctgc agtatggaag    5460
catcaccacc attgacgtgc catggaacgt ggtcccggag aaagcccatt tgctgagcct    5520
tgtggacgtc atgcagcggg agggaggcc cagccaaatc ggggatgcct tgggctttgc    5580
tgtgcgatac ttgacttcag aaatgcatgg tgccaggccg ggagcctcaa aggcggtggt    5640
catcctggtc acggacgtct ctgtggattc agtggatgca gcagctgatg ccgccaggtc    5700
caacagagtg acagtgttcc ctattggaat tggagatcgc tacgatgcag cccagctacg    5760
gatcttggca ggcccagcag gcgactccaa cgtggtgaag ctccagcgaa tcgaagacct    5820
ccctaccatg gtcaccttgg gcaattcctt cctccacaaa ctgtgctctg gatttgttag    5880
gatttgcatg gatgaggatg ggaatgagaa gaggcccggg gacgtctgga ccttgccaga    5940
ccagtgccac accgtgactt gccagccaga tggccagacc ttgctgaaga gtcatcgggt    6000
caactgtgac cgggggctga ggccttcgtg ccctaacagc cagtcccctg ttaaagtgga    6060
agagacctgt ggctgccgct ggaccctgcc ctgcgtgtgc acaggcagct ccactcggca    6120
catcgtgacc tttgatgggc agaatttcaa gctgactgga agctgttctt atgtcctatt    6180
tcaaaacaag gagcaggacc tggaggtgat tctccataat ggtgcctgca gccctggagc    6240
```

```
aaggcagggc tgcatgaaat ccatcgaggt gaagcacagt gccctctccg tcgagctgca   6300
cagtgacatg gaggtgacgg tgaatgggag actggtctct gttccttacg tgggtgggaa   6360
catggaagtc aacgtttatg gtgccatcat gcatgaggtc agattcaatc accttggtca   6420
catcttcaca ttcactccac aaaacaatga gttccaactg cagctcagcc ccaagacttt   6480
tgcttcaaag acgtatggtc tgtgtgggat ctgtgatgag aacggagcca atgacttcat   6540
gctgagggat ggcacagtca ccacagactg gaaaacactt gttcaggaat ggactgtgca   6600
gcggccaggg cagacgtgcc agcccatcct ggaggagcag tgtcttgtcc ccgacagctc   6660
ccactgccag gtcctcctct taccactgtt tgctgaatgc acaaggtcc tggctccagc    6720 cacattctat gccatctgcc agcaggacag ttgccaccag gagcaagtgt gtgaggtgat   6780
cgcctcttat gcccacctct gtcggaccaa cggggtctgc gttgactgga ggacacctga   6840
tttctgtgct atgtcatgcc caccatctct ggtctacaac cactgtgagc atggctgtcc   6900
ccggcactgt gatggcaacg tgagctcctg tggggaccat ccctccgaag ctgtttctg    6960 ccctccagat aaagtcatgt tggaaggcag ctgtgtccct gaagaggcct gcactcagtg   7020
cattggtgag gatggagtcc agcaccagtt cctggaagcc tgggtcccgg accaccagcc   7080
ctgtcagatc tgcacatgcc tcagcgggcg gaaggtcaac tgcacaacgc agccctgccc   7140
cacggccaaa gctcccacgt gtggcctgtg tgaagtagcc cgcctccgcc agaatgcaga   7200
ccagtgctgc cccgagtatg agtgtgtgtg tgacccagtg agctgtgacc tgccccagt    7260 gcctcactgt gaacgtggcc tccagcccac actgaccaac cctggcgagt gcagacccaa   7320
cttcacctgc gcctgcagga aggaggagtg caaaagagtg tccccaccct cctgccccc    7380 gcaccgtttg cccaccccttc ggaagaccca gtgctgtgat gagtatgagt gtgcctgcaa   7440
ctgtgtcaac tccacagtga gctgtccct tgggtacttg gcctcaactg ccaccaatga    7500
ctgtggctgt accacaacca cctgccttcc cgacaaggtg tgtgtccacc gaagcaccat   7560
ctaccctgtg ggccagttct gggaggaggg ctgcgatgtg tgcacctgca ccgacatgga   7620
ggatgccgtg atgggcctcc gcgtggccca gtgctcccag aagccctgtg aggacagctg   7680
tcggtcgggc ttcacttacg ttctgcatga aggcgagtgc tgtggaaggt gcctgccatc   7740
tgcctgtgag gtggtgactg gctcaccgcg gggggactcc cagtcttcct ggaagagtgt   7800
cggctcccag tgggcctccc cggagaaccc ctgcctcatc aatgagtgtg tccgagtgaa   7860
ggaggaggtc tttatacaac aaaggaacgt ctcctgcccc cagctggagg tccctgtctg   7920 ccccctcgggc tttcagctga gctgtaagac ctcagcgtgc tgcccaagct gtcgctgtga   7980
gcgcatggag gcctgcatgc tcaatggcac tgtcattggg cccgggaaga ctgtgatgat   8040
cgatgtgtgc acgacctgcc gctgcatggt gcaggtgggg gtcatctctg gattcaagct   8100
ggagtgcagg aagaccacct gcaaccctg ccccctgggt tacaaggaag aaaataacac    8160
aggtgaatgt tgtgggagat gtttgcctac ggcttgcacc attcagctaa gaggaggaca   8220
gatcatgaca ctgaagcgtg atgagacgct ccaggatggc tgtgatactc acttctgcaa   8280
ggtcaatgag agaggagagt acttctggga agagggtc acaggctgcc cacccttga     8340 tgaacacaag tgtctggctg agggaggtaa aattatgaaa attccaggca cctgctgtga   8400
cacatgtgag gagcctgagt gcaacgacat cactgccagg ctgcagtatg tcaaggtggg   8460
aagctgtaag tctgaagtag aggtggatat ccactactgc cagggcaaat gtgccagcaa   8520
agccatgtac tccattgaca tcaacgatgt gcaggaccag tgctcctgct gctctccgac   8580
```

-continued

```
acggacggag cccatgcagg tggccctgca ctgcaccaat ggctctgttg tgtaccatga    8640
ggttctcaat gccatggagt gcaaatgctc ccccaggaag tgcagcaagt gaggctgctg    8700
cagctgcatg ggtgcctgct gctgcctgcc ttggcctgat ggccaggcca gagtgctgcc    8760
agtcctctgc atgttctgct cttgtgccct tctgagccca caataaaggc tgagctctta    8820
tcttgcaaaa ggc                                                       8833
```

```
<210> SEQ ID NO 9
<211> LENGTH: 2813
<212> TYPE: PRT
<213> ORGANISM: Homo sapiens

<400> SEQUENCE: 9
```

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu

-continued

```
                325                 330                 335
Leu Asp Glu Gly Leu Cys Val Glu Ser Thr Glu Cys Pro Cys Val His
                340                 345                 350
Ser Gly Lys Arg Tyr Pro Pro Gly Thr Ser Leu Ser Arg Asp Cys Asn
                355                 360                 365
Thr Cys Ile Cys Arg Asn Ser Gln Trp Ile Cys Ser Asn Glu Glu Cys
                370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                405                 410                 415
Asp Cys Gln Asp His Ser Phe Ser Ile Val Ile Glu Thr Val Gln Cys
                420                 425                 430
Ala Asp Asp Arg Asp Ala Val Cys Thr Arg Ser Val Thr Val Arg Leu
                435                 440                 445
Pro Gly Leu His Asn Ser Leu Val Lys Leu Lys His Gly Ala Gly Val
                450                 455                 460
Ala Met Asp Gly Gln Asp Val Gln Leu Pro Leu Leu Lys Gly Asp Leu
465                 470                 475                 480
Arg Ile Gln His Thr Val Thr Ala Ser Val Arg Leu Ser Tyr Gly Glu
                485                 490                 495
Asp Leu Gln Met Asp Trp Asp Gly Arg Gly Arg Leu Leu Val Lys Leu
                500                 505                 510
Ser Pro Val Tyr Ala Gly Lys Thr Cys Gly Leu Cys Gly Asn Tyr Asn
                515                 520                 525
Gly Asn Gln Gly Asp Asp Phe Leu Thr Pro Ser Gly Leu Ala Glu Pro
                530                 535                 540
Arg Val Glu Asp Phe Gly Asn Ala Trp Lys Leu His Gly Asp Cys Gln
545                 550                 555                 560
Asp Leu Gln Lys Gln His Ser Asp Pro Cys Ala Leu Asn Pro Arg Met
                565                 570                 575
Thr Arg Phe Ser Glu Glu Ala Cys Ala Val Leu Thr Ser Pro Thr Phe
                580                 585                 590
Glu Ala Cys His Arg Ala Val Ser Pro Leu Pro Tyr Leu Arg Asn Cys
                595                 600                 605
Arg Tyr Asp Val Cys Ser Cys Ser Asp Gly Arg Glu Cys Leu Cys Gly
                610                 615                 620
Ala Leu Ala Ser Tyr Ala Ala Ala Cys Ala Gly Arg Gly Val Arg Val
625                 630                 635                 640
Ala Trp Arg Glu Pro Gly Arg Cys Glu Leu Asn Cys Pro Lys Gly Gln
                645                 650                 655
Val Tyr Leu Gln Cys Gly Thr Pro Cys Asn Leu Thr Cys Arg Ser Leu
                660                 665                 670
Ser Tyr Pro Asp Glu Glu Cys Asn Glu Ala Cys Leu Glu Gly Cys Phe
                675                 680                 685
Cys Pro Pro Gly Leu Tyr Met Asp Glu Arg Gly Asp Cys Val Pro Lys
                690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
                725                 730                 735
His Cys Thr Met Ser Gly Val Pro Gly Ser Leu Leu Pro Asp Ala Val
                740                 745                 750
```

```
Leu Ser Ser Pro Leu Ser His Arg Ser Lys Arg Ser Leu Ser Cys Arg
            755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
   1010                 1015                1020

Ser Trp  Lys Val Ser Ser Gln  Cys Ala Asp Thr Arg  Lys Val Pro
   1025                 1030                1035

Leu Asp  Ser Ser Pro Ala Thr  Cys His Asn Asn Ile  Met Lys Gln
   1040                 1045                1050

Thr Met  Val Asp Ser Ser Cys  Arg Ile Leu Thr Ser  Asp Val Phe
   1055                 1060                1065

Gln Asp  Cys Asn Lys Leu Val  Asp Pro Glu Pro Tyr  Leu Asp Val
   1070                 1075                1080

Cys Ile  Tyr Asp Thr Cys Ser  Cys Glu Ser Ile Gly  Asp Cys Ala
   1085                 1090                1095

Cys Phe  Cys Asp Thr Ile Ala  Ala Tyr Ala His Val  Cys Ala Gln
   1100                 1105                1110

His Gly  Lys Val Val Thr Trp  Arg Thr Ala Thr Leu  Cys Pro Gln
   1115                 1120                1125

Ser Cys  Glu Glu Arg Asn Leu  Arg Glu Asn Gly Tyr  Glu Cys Glu
   1130                 1135                1140

Trp Arg  Tyr Asn Ser Cys Ala  Pro Ala Cys Gln Val  Thr Cys Gln
   1145                 1150                1155
```

-continued

```
His Pro Glu Pro Leu Ala Cys Pro Val Gln Cys Val Glu Gly Cys
    1160                1165                1170
His Ala His Cys Pro Pro Gly Lys Ile Leu Asp Glu Leu Leu Gln
    1175                1180                1185
Thr Cys Val Asp Pro Glu Asp Cys Pro Val Cys Glu Val Ala Gly
    1190                1195                1200
Arg Arg Phe Ala Ser Gly Lys Lys Val Thr Leu Asn Pro Ser Asp
    1205                1210                1215
Pro Glu His Cys Gln Ile Cys His Cys Asp Val Val Asn Leu Thr
    1220                1225                1230
Cys Glu Ala Cys Gln Glu Pro Gly Gly Leu Val Val Pro Pro Thr
    1235                1240                1245
Asp Ala Pro Val Ser Pro Thr Thr Leu Tyr Val Glu Asp Ile Ser
    1250                1255                1260
Glu Pro Pro Leu His Asp Phe Tyr Cys Ser Arg Leu Leu Asp Leu
    1265                1270                1275
Val Phe Leu Leu Asp Gly Ser Ser Arg Leu Ser Glu Ala Glu Phe
    1280                1285                1290
Glu Val Leu Lys Ala Phe Val Val Asp Met Met Glu Arg Leu Arg
    1295                1300                1305
Ile Ser Gln Lys Trp Val Arg Val Ala Val Val Glu Tyr His Asp
    1310                1315                1320
Gly Ser His Ala Tyr Ile Gly Leu Lys Asp Arg Lys Arg Pro Ser
    1325                1330                1335
Glu Leu Arg Arg Ile Ala Ser Gln Val Lys Tyr Ala Gly Ser Gln
    1340                1345                1350
Val Ala Ser Thr Ser Glu Val Leu Lys Tyr Thr Leu Phe Gln Ile
    1355                1360                1365
Phe Ser Lys Ile Asp Arg Pro Glu Ala Ser Arg Ile Thr Leu Leu
    1370                1375                1380
Leu Met Ala Ser Gln Glu Pro Gln Arg Met Ser Arg Asn Phe Val
    1385                1390                1395
Arg Tyr Val Gln Gly Leu Lys Lys Lys Lys Val Ile Val Ile Pro
    1400                1405                1410
Val Gly Ile Gly Pro His Ala Asn Leu Lys Gln Ile Arg Leu Ile
    1415                1420                1425
Glu Lys Gln Ala Pro Glu Asn Lys Ala Phe Val Leu Ser Ser Val
    1430                1435                1440
Asp Glu Leu Glu Gln Gln Arg Asp Glu Ile Val Ser Tyr Leu Cys
    1445                1450                1455
Asp Leu Ala Pro Glu Ala Pro Pro Pro Thr Leu Pro Pro Asp Met
    1460                1465                1470
Ala Gln Val Thr Val Gly Pro Gly Leu Leu Gly Val Ser Thr Leu
    1475                1480                1485
Gly Pro Lys Arg Asn Ser Met Val Leu Asp Val Ala Phe Val Leu
    1490                1495                1500
Glu Gly Ser Asp Lys Ile Gly Glu Ala Asp Phe Asn Arg Ser Lys
    1505                1510                1515
Glu Phe Met Glu Glu Val Ile Gln Arg Met Asp Val Gly Gln Asp
    1520                1525                1530
Ser Ile His Val Thr Val Leu Gln Tyr Ser Tyr Met Val Thr Val
    1535                1540                1545
Glu Tyr Pro Phe Ser Glu Ala Gln Ser Lys Gly Asp Ile Leu Gln
```

```
            1550                1555                1560
Arg Val Arg Glu Ile Arg Tyr Gln Gly Gly Asn Arg Thr Asn Thr
    1565                1570                1575
Gly Leu Ala Leu Arg Tyr Leu Ser Asp His Ser Phe Leu Val Ser
    1580                1585                1590
Gln Gly Asp Arg Glu Gln Ala Pro Asn Leu Val Tyr Met Val Thr
    1595                1600                1605
Gly Asn Pro Ala Ser Asp Glu Ile Lys Arg Leu Pro Gly Asp Ile
    1610                1615                1620
Gln Val Val Pro Ile Gly Val Gly Pro Asn Ala Asn Val Gln Glu
    1625                1630                1635
Leu Glu Arg Ile Gly Trp Pro Asn Ala Pro Ile Leu Ile Gln Asp
    1640                1645                1650
Phe Glu Thr Leu Pro Arg Glu Ala Pro Asp Leu Val Leu Gln Arg
    1655                1660                1665
Cys Cys Ser Gly Glu Gly Leu Gln Ile Pro Thr Leu Ser Pro Ala
    1670                1675                1680
Pro Asp Cys Ser Gln Pro Leu Asp Val Ile Leu Leu Leu Asp Gly
    1685                1690                1695
Ser Ser Ser Phe Pro Ala Ser Tyr Phe Asp Glu Met Lys Ser Phe
    1700                1705                1710
Ala Lys Ala Phe Ile Ser Lys Ala Asn Ile Gly Pro Arg Leu Thr
    1715                1720                1725
Gln Val Ser Val Leu Gln Tyr Gly Ser Ile Thr Thr Ile Asp Val
    1730                1735                1740
Pro Trp Asn Val Val Pro Glu Lys Ala His Leu Leu Ser Leu Val
    1745                1750                1755
Asp Val Met Gln Arg Glu Gly Gly Pro Ser Gln Ile Gly Asp Ala
    1760                1765                1770
Leu Gly Phe Ala Val Arg Tyr Leu Thr Ser Glu Met His Gly Ala
    1775                1780                1785
Arg Pro Gly Ala Ser Lys Ala Val Val Ile Leu Val Thr Asp Val
    1790                1795                1800
Ser Val Asp Ser Val Asp Ala Ala Ala Asp Ala Ala Arg Ser Asn
    1805                1810                1815
Arg Val Thr Val Phe Pro Ile Gly Ile Gly Asp Arg Tyr Asp Ala
    1820                1825                1830
Ala Gln Leu Arg Ile Leu Ala Gly Pro Ala Gly Asp Ser Asn Val
    1835                1840                1845
Val Lys Leu Gln Arg Ile Glu Asp Leu Pro Thr Met Val Thr Leu
    1850                1855                1860
Gly Asn Ser Phe Leu His Lys Leu Cys Ser Gly Phe Val Arg Ile
    1865                1870                1875
Cys Met Asp Glu Asp Gly Asn Glu Lys Arg Pro Gly Asp Val Trp
    1880                1885                1890
Thr Leu Pro Asp Gln Cys His Thr Val Thr Cys Gln Pro Asp Gly
    1895                1900                1905
Gln Thr Leu Leu Lys Ser His Arg Val Asn Cys Asp Arg Gly Leu
    1910                1915                1920
Arg Pro Ser Cys Pro Asn Ser Gln Ser Pro Val Lys Val Glu Glu
    1925                1930                1935
Thr Cys Gly Cys Arg Trp Thr Cys Pro Cys Val Cys Thr Gly Ser
    1940                1945                1950
```

Ser Thr Arg His Ile Val Thr Phe Asp Gly Gln Asn Phe Lys Leu
1955                1960                1965

Thr Gly Ser Cys Ser Tyr Val Leu Phe Gln Asn Lys Glu Gln Asp
1970                1975                1980

Leu Glu Val Ile Leu His Asn Gly Ala Cys Ser Pro Gly Ala Arg
1985                1990                1995

Gln Gly Cys Met Lys Ser Ile Glu Val Lys His Ser Ala Leu Ser
2000                2005                2010

Val Glu Leu His Ser Asp Met Glu Val Thr Val Asn Gly Arg Leu
2015                2020                2025

Val Ser Val Pro Tyr Val Gly Gly Asn Met Glu Val Asn Val Tyr
2030                2035                2040

Gly Ala Ile Met His Glu Val Arg Phe Asn His Leu Gly His Ile
2045                2050                2055

Phe Thr Phe Thr Pro Gln Asn Asn Glu Phe Gln Leu Gln Leu Ser
2060                2065                2070

Pro Lys Thr Phe Ala Ser Lys Thr Tyr Gly Leu Cys Gly Ile Cys
2075                2080                2085

Asp Glu Asn Gly Ala Asn Asp Phe Met Leu Arg Asp Gly Thr Val
2090                2095                2100

Thr Thr Asp Trp Lys Thr Leu Val Gln Glu Trp Thr Val Gln Arg
2105                2110                2115

Pro Gly Gln Thr Cys Gln Pro Ile Leu Glu Glu Gln Cys Leu Val
2120                2125                2130

Pro Asp Ser Ser His Cys Gln Val Leu Leu Leu Pro Leu Phe Ala
2135                2140                2145

Glu Cys His Lys Val Leu Ala Pro Ala Thr Phe Tyr Ala Ile Cys
2150                2155                2160

Gln Gln Asp Ser Cys His Gln Glu Gln Val Cys Glu Val Ile Ala
2165                2170                2175

Ser Tyr Ala His Leu Cys Arg Thr Asn Gly Val Cys Val Asp Trp
2180                2185                2190

Arg Thr Pro Asp Phe Cys Ala Met Ser Cys Pro Pro Ser Leu Val
2195                2200                2205

Tyr Asn His Cys Glu His Gly Cys Pro Arg His Cys Asp Gly Asn
2210                2215                2220

Val Ser Ser Cys Gly Asp His Pro Ser Glu Gly Cys Phe Cys Pro
2225                2230                2235

Pro Asp Lys Val Met Leu Glu Gly Ser Cys Val Pro Glu Glu Ala
2240                2245                2250

Cys Thr Gln Cys Ile Gly Glu Asp Gly Val Gln His Gln Phe Leu
2255                2260                2265

Glu Ala Trp Val Pro Asp His Gln Pro Cys Gln Ile Cys Thr Cys
2270                2275                2280

Leu Ser Gly Arg Lys Val Asn Cys Thr Thr Gln Pro Cys Pro Thr
2285                2290                2295

Ala Lys Ala Pro Thr Cys Gly Leu Cys Glu Val Ala Arg Leu Arg
2300                2305                2310

Gln Asn Ala Asp Gln Cys Cys Pro Glu Tyr Glu Cys Val Cys Asp
2315                2320                2325

Pro Val Ser Cys Asp Leu Pro Pro Val Pro His Cys Glu Arg Gly
2330                2335                2340

```
Leu Gln Pro Thr Leu Thr Asn Pro Gly Glu Cys Arg Pro Asn Phe
2345                2350                2355

Thr Cys Ala Cys Arg Lys Glu Glu Cys Lys Arg Val Ser Pro Pro
2360                2365                2370

Ser Cys Pro Pro His Arg Leu Pro Thr Leu Arg Lys Thr Gln Cys
2375                2380                2385

Cys Asp Glu Tyr Glu Cys Ala Cys Asn Cys Val Asn Ser Thr Val
2390                2395                2400

Ser Cys Pro Leu Gly Tyr Leu Ala Ser Thr Ala Thr Asn Asp Cys
2405                2410                2415

Gly Cys Thr Thr Thr Thr Cys Leu Pro Asp Lys Val Cys Val His
2420                2425                2430

Arg Ser Thr Ile Tyr Pro Val Gly Gln Phe Trp Glu Glu Gly Cys
2435                2440                2445

Asp Val Cys Thr Cys Thr Asp Met Glu Asp Ala Val Met Gly Leu
2450                2455                2460

Arg Val Ala Gln Cys Ser Gln Lys Pro Cys Glu Asp Ser Cys Arg
2465                2470                2475

Ser Gly Phe Thr Tyr Val Leu His Glu Gly Glu Cys Cys Gly Arg
2480                2485                2490

Cys Leu Pro Ser Ala Cys Glu Val Val Thr Gly Ser Pro Arg Gly
2495                2500                2505

Asp Ser Gln Ser Ser Trp Lys Ser Val Gly Ser Gln Trp Ala Ser
2510                2515                2520

Pro Glu Asn Pro Cys Leu Ile Asn Glu Cys Val Arg Val Lys Glu
2525                2530                2535

Glu Val Phe Ile Gln Gln Arg Asn Val Ser Cys Pro Gln Leu Glu
2540                2545                2550

Val Pro Val Cys Pro Ser Gly Phe Gln Leu Ser Cys Lys Thr Ser
2555                2560                2565

Ala Cys Cys Pro Ser Cys Arg Cys Glu Arg Met Glu Ala Cys Met
2570                2575                2580

Leu Asn Gly Thr Val Ile Gly Pro Gly Lys Thr Val Met Ile Asp
2585                2590                2595

Val Cys Thr Thr Cys Arg Cys Met Val Gln Val Gly Val Ile Ser
2600                2605                2610

Gly Phe Lys Leu Glu Cys Arg Lys Thr Thr Cys Asn Pro Cys Pro
2615                2620                2625

Leu Gly Tyr Lys Glu Glu Asn Asn Thr Gly Glu Cys Cys Gly Arg
2630                2635                2640

Cys Leu Pro Thr Ala Cys Thr Ile Gln Leu Arg Gly Gly Gln Ile
2645                2650                2655

Met Thr Leu Lys Arg Asp Glu Thr Leu Gln Asp Gly Cys Asp Thr
2660                2665                2670

His Phe Cys Lys Val Asn Glu Arg Gly Glu Tyr Phe Trp Glu Lys
2675                2680                2685

Arg Val Thr Gly Cys Pro Pro Phe Asp Glu His Lys Cys Leu Ala
2690                2695                2700

Glu Gly Gly Lys Ile Met Lys Ile Pro Gly Thr Cys Cys Asp Thr
2705                2710                2715

Cys Glu Glu Pro Glu Cys Asn Asp Ile Thr Ala Arg Leu Gln Tyr
2720                2725                2730

Val Lys Val Gly Ser Cys Lys Ser Glu Val Glu Val Asp Ile His
```

-continued

```
                2735                2740                2745

Tyr Cys Gln Gly Lys Cys Ala Ser Lys Ala Met Tyr Ser Ile Asp
        2750                2755                2760

Ile Asn Asp Val Gln Asp Gln Cys Ser Cys Ser Pro Thr Arg
        2765                2770                2775

Thr Glu Pro Met Gln Val Ala Leu His Cys Thr Asn Gly Ser Val
        2780                2785                2790

Val Tyr His Glu Val Leu Asn Ala Met Glu Cys Lys Cys Ser Pro
        2795                2800                2805

Arg Lys Cys Ser Lys
        2810

<210> SEQ ID NO 10
<211> LENGTH: 10
<212> TYPE: PRT
<213> ORGANISM: Homo sapiens

<400> SEQUENCE: 10

Glu Gln Lys Leu Ile Ser Glu Glu Asp Leu
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Tyr Lys Asp Asp Asp Asp Lys
1               5

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'-O-Methyl nucleotide

<400> SEQUENCE: 12
acaugugucu uaggucccug gc                                                22
```

COMPOSITIONS AND METHODS FOR THE TREATMENT OF COMPLICATIONS AND DISORDERS RELATING TO VON WILLEBRAND FACTOR

CROSS REFERENCE TO RELATED APPLICATIONS

This application is a 35 U.S.C. § 371 U.S. National Stage Entry of International Application No. PCT/US2018/033376 filed May 18, 2018, which claims priority to U.S. Provisional Patent Application No. 62/508,530, filed May 19, 2017, entitled "Compositions and Methods for the Treatment of Complications and Disorders Relating to Von Willebrand Factor"; and U.S. Provisional Patent Application No. 62/638,579, filed Mar. 5, 2018, entitled "Compositions and Methods for the Treatment of Complications and Disorders Relating to Von Willebrand Factor"; the contents of each of which are herein incorporated by reference in their entirety.

SEQUENCE LISTING

The present application is being filed along with a Sequence Listing in electronic format. The Sequence Listing is provided as a file entitled 2059-1002US371SL.txt, created on Nov. 14, 2019, which is 40,988 bytes in size. The information in the electronic format of the sequence listing is incorporated herein by reference in its entirety.

FIELD OF THE INVENTION

The present invention relates to the field of therapeutic modalities useful in the treatment of complications and disorders relating to von Willebrand factor.

BACKGROUND OF THE INVENTION

Von Willebrand Factor (VWF) is essential for the first step in maintaining hemostasis, i.e., arresting hemorrhage at sites where there has been a break in the integrity of the vasculature. VWF makes a molecular bridge between the collagen structural matrix which underlies the vascular endothelium and circulating blood platelets, enabling platelets to adhere to sites of vessel damage and initiate formation of thrombus in order to arrest hemorrhage. This essential function of VWF is performed by high molecular weight multimers of individual VWF molecules, and these multimers are activated to bind platelets when they are exposed to hemodynamic shear forces (in a manner analogous to uncoiling a rope). Activation of VWF has been shown to occur through a two-step conformational transition: flow-induced elongation followed by a tension-dependent local transition to a state with high affinity for platelet GpIbα (Fu H, et al., *Flow-induced elongation of von Willebrand factor precedes tension-dependent activation*. Nat Commun. 2017 Aug. 23; 8(1):324). At the same time, the uncoiling which activates VWF multimers also exposes them to destruction by proteolysis, thus providing a feedback loop that prevents excessive thrombus formation. More recently, VWF has been found to be involved in a number of processes in the vasculature, including the regulation of new blood vessel formation (Randi A M, et al., *Von Willebrand Factor, Angiodysplasia and Angiogenesis*. Mediterr J Hematol Infect Dis. 2013; 5(1): e2013060; eCollection 2013).

Recent advances in the design of the medical device known as a ventricular assist device ("VAD") have improved VAD performance and the hemodynamic support such devices can provide to patients with severe heart failure. One such advance was the introduction of continuous (as opposed to pulsatile) flow systems, exemplified in devices such as HeartWare's HVAD® or Thoratec's HEARTMATE®. However, one of the major drawbacks of mechanically supporting blood flow is the fact that the blood is locally exposed to non-physiological flow conditions, such as high pressures and steep velocity gradients. Thus, in VAD patients, VWF (and other blood components) are continuously subjected to high shear force created by the VAD itself. The hemodynamic shear forces produced by the continuous flow pump design can cause a defect in the function of the coagulation system known as Acquired Von Willebrand Syndrome (aVWS) and, as a result, a substantial incidence of major bleeding, especially from the gastrointestinal (GI) tract. Abnormal blood vessel formation is also observed in these patients and contributes to the bleeding (Suarez J, et al., *Mechanisms of bleeding and approach to patients with axial-flow left ventricular assist devices*. Circ. Heart Fail. 2011 4:779-84 and references therein).

The effect of this mechanical shear force is further amplified by the tethering of circulating platelets as the VWF multimer begins to uncoil and expose its platelet binding sites (sites which are biochemically designated "A1 domains"). That is, as platelets in flowing blood are bound to A1 domains exposed on the partially uncoiled VWF multimer, the bound platelets apply traction and fully stretch out the multimeric strand. Once fully extended the VWF multimer is most susceptible to proteolytic degradation. This pathophysiologic paradigm predicts that VAD patients would manifest reduced amounts of the fully functional, high molecular weight VWF multimers, which is indeed the case. Administration of exogenous VWF or stimulation of secretion of endogenous stores of VWF would not be predicted to provide a lasting correction to the problem, since the supplemental VWF would soon also become proteolytically degraded in the same manner.

Another drawback of ventricular assist devices, in particular, left ventricular assist devices (LVADs), as a result of the high shear forces has recently been reported by Starling et al., who have observed an increase in the rate of thrombosis in the VAD instrument among patients who received the HeartMate II™ LVAD. Starling R C, et al., *Unexpected Abrupt Increase in Left Ventricular Assist Device Thrombosis*, 2014, N. Engl. J Med., 370:33-40. Others have reported similar findings with LVADs. Capoccia M, et al., *Recurrent Early Thrombus Formation in Heartmate II Left Ventricular Assist Device*, 2013, J. Inv. Med., 1:DOI:10, 1177/2324709613490676; Meyer A L, et al., *Thrombus Formation in a Heartmate II Left Ventricular Assist Device*, 2008, J. Thorac Cardiovasc Surg, 135:203-204. The high shear rate at the VAD activates VWF, causing local thrombus formation at the VAD inlet and systemic VWF depletion leading to aVWS.

As discussed above, platelet aggregation at sites of vascular injury is central to the arrest and control of bleeding, as well as for subsequent vascular repair; however, an exaggerated platelet aggregation response at sites of vascular damage or atherosclerotic plaque rupture can lead to the development of vascular occlusive thrombi. Studies have shown that VWF-platelet interactions mediate occlusive thrombi formation under very high shear rates. Le Behot A, et al., *GpIbα-VWF blockade restores vessel patency by dissolving platelet aggregates formed under very high shear rate in mice*. Blood, 2013: Feb. 19, 2014; DOI 10.1182/blood-2013-12-543074. Thus, elevated levels of shear stress in VAD are associated with both aVWS (as a result of VWF multimer formation and subsequent destruction by proteolysis) and thrombus formation (as a result of the VWF-platelet aggregation response).

Thrombus development in the coronary and cerebral arteries is the most common cause of mortality and morbidity worldwide, precipitating diseases such as myocardial infarction and ischemic stroke, respectively. Current thrombolytic treatments target only one constituent of the thrombus, fibrin, and are therefore only partially effective in dissolving arterial and platelet-rich thrombi. Furthermore, while treatment that seeks to disrupt the platelet-fibrin interaction (i.e., platelet GpIIb/IIIa inhibitors) is effective for preventing initial thrombus formation and dissolving fresh platelet aggregates, such disruption does not significantly prevent thrombus formation in pre-occluded arteries having very high shear rates or have a significant impact on the patency of pre-occluded arteries (vessels that are at least 50% occluded). More recent studies have shown, however, that blockage of the interaction between VWF (A1 domain) and its cognate ligand on platelets (GpIb) slows the rate of occlusive thrombus formation under very high shear rates and dissolves already-formed occlusive thrombi, thereby effectively increasing the patency of occluded arteries.

Another disorder associated with VWF interactions is sickle cell disease.

Sickle cell disease results from inheritance of a mutant β-globin allele (Glu6Val), either as 2 copies or with an allele specifying deficient or defective β-globin, yielding rigid, adhesive, lysis-prone erythrocytes. These properties account for the clinical manifestations of sickle cell disease, including chronic hemolytic anemia and episodic vaso-occlusion, affecting many organs. Patients with the highest hemolytic rates are at risk for a syndrome composed of pulmonary artery hypertension, priapism, and leg ulcers. Several adhesive molecules have been implicated in sickle vaso-occlusion, including VWF. Acutely activated endothelial cells can release massive quantities of very large and hyperadhesive VWF molecules which are capable of spontaneously binding erythrocytes, especially sickle cells.

There is extensive medical literature describing the phenomenon of VAD-associated acquired Von Willebrand Syndrome (aVWS); however, no known cure is currently available (See: Suarez J, et al., *Mechanisms of Bleeding and Approach to Patients with Axial-Flow Left Ventricular Assist Devices*. Circulation: Heart Failure 2011; 4(6):779-784). Current treatments involve administration of additional clotting factors or concentrated VWF, each of which carries significant risk.

Likewise, there is recent literature describing the observation of thrombosis in the VAD instrument among patients who received VAD treatment and, in particular LVAD treatment. Such thrombosis is referred to herein as "VAD-associated pump thrombosis." See, for example, FIG. 2 in Starling R C, et al., *Unexpected Abrupt Increase in Left Ventricular Assist Device Thrombosis*, 2014, N. Engl. J Med., 370:33-40, which shows thrombus formation in LVAD. To date, however, no therapies have been proposed or adopted to prevent the incidence of thrombosis, other than anticoagulant therapies.

Consequently, there remains a need for drugs or biotherapeutic agents which target VWF interactions. Specifically, there remains a need for pharmacologic antagonists of the processes by which VWF multimers are destroyed in VAD patients and which are antagonists of thrombi formed under very high shear rates, such as those found in VAD patients and also in pre-occluded vascular vessels (which may be present in both VAD and non-VAD subjects). There also remains a need for antagonists of thrombus formation in VAD instruments. In each of these various conditions, such agents may antagonize the binding interaction between the A1 domain of VWF and its cognate ligand on platelets, erythrocytes and/or GpIb, thereby strengthening the VWF multimers and/or slowing their destruction. Utilization of such compounds or compositions as a therapy in VAD patients for aVWS is quite counterintuitive as it entails administration of an anti-clotting agent (which increases bleeding) to correct a bleeding problem. The therapeutic rationale however is sound in that preservation of the high molecular weight VWF multimers in VAD patients will prevent the downstream cascade which ultimately leads to VWF proteolysis. Such agents may also antagonize the binding interaction between the A1 domain of VWF and its cognate ligand on platelets and/or GpIb, thereby disrupting and/or slowing the formation of occlusive thrombi.

There also remains a need for agents that antagonize platelet aggregation or cross-linking during closure (occlusion) of a vessel lumen (i.e., under very high shear rates, such as those found in VAD patients and/or subjects with pre-occluded vessels) and agents that are able to disaggregate or disrupt already-formed occlusive thrombi in a vessel. Such agents may antagonize the interaction between VWF and platelets, thereby restoring vessel patency after occlusive thrombosis by disaggregating existing thrombi. Such agents are useful for the treatment of cardiovascular and coronary diseases, such as myocardial infarction and ischemic stroke. Such agents may also be useful to discourage the development of occlusive thrombi during VAD treatment.

There also remains a further need for therapeutic intervention in complications and disorders arising from other interactions of VWF multimers with erythrocytes, particularly in the case of aberrant binding of VWF to erythrocytes in sickle cell disease. Such agents may modulate the binding of VWF to erythrocytes in sickle cell disease.

As stated, there remains a need for therapeutics for the treatment of vascular assist device (VAD) associated complications and disorders, such as aVWS and occlusive thrombosis, and for disorders arising from interactions of VWF multimers with erythrocytes, such as the interaction that occurs between VWF multimers and erythrocytes in sickle cell disease. There additionally remains a need for therapeutics that antagonize platelet aggregation during occlusion of a vessel lumen or during thrombus formation during treatment with a VAD instrument, and agents that are able to disaggregate or disrupt already-formed occlusive thrombi in a vessel or already-formed thrombi in a VAD pump in the treatment of cardiovascular and/or coronary diseases, such as stroke.

SUMMARY OF THE INVENTION

The present disclosure provides, among other things, antagonists of the VWF-platelet interaction and of the VWF-erythrocyte interaction which may occur in circumstances such as sickle cell disease either independently or in combination with VAD treatment, and which may occur in circumstances of platelet aggregation during occlusive thrombus formation in VAD patients or during closure of the lumen of a vessel such as that which may occur in any number of conditions, such as, for example ischemic stroke. Such antagonists may serve as VWF protective agents. Such antagonists may also serve as therapeutic agents in the regulation and modulation of hemostasis, therapeutic agents for the treatment of vascular assist device (VAD) associated complications and disorders, such as aVWS and occlusive thrombosis, and therapeutic agents for the treatment of disorders arising from interactions of VWF multimers with erythrocytes, such as in sickle cell disease. In addition, such agents may serve as therapeutic agents in the treatment of cardiovascular and cerebrovascular disorders, such as myocardial infarction and stroke.

Also provided are VWF protective agents comprising synthetic polynucleotides comprising at least 21 contiguous nucleotides of SEQ ID NO: 1, which exhibit a double stranded region having at least 6 base pairs. VWF protective agents having a double stranded region of at least 6 base pairs may have greater thermostability at higher temperatures and thereby greater affinity for VWF and increased functionality as compared to protective agents with a shorter double stranded region of 5 base pairs or less. Shorter double stranded regions may lead to unraveling of the stem-loop structure at higher temperatures and associated loss of affinity and functionality.

In some embodiments, the synthetic polynucleotide of the present invention may be 25-30 nucleotides in length. The double stranded region may be from about 6 to about 9 base pairs. Furthermore, the double stranded region is formed by 6 or more of the 3' and 5' nucleotides at or near the termini.

The synthetic polynucleotides of the present invention may be chemically modified. Each nucleotide may contain at least one chemical modification. Such chemical modification may be at the sugar, nucleobase or internucleoside linker of the synthetic polynucleotide. Modifications to the sugar may consist of a 2' O-methyl modification.

Terminal cap structures may also be incorporated to the 3' and/or 5' termini. Such structures include, but are not limited to at least one inverted deoxythymidine or amino group ($NH_2$). In one aspect, the 3' terminal cap comprises an inverted deoxythymidine and the 5' terminal cap comprises an amino group ($NH_2$). In one aspect, the synthetic polynucleotide is SEQ ID NO: 2.

The VWF protective agents comprising nucleic acid aptamers may be modified by any number of conjugates. One such conjugate is a PEG (polyethylene glycol) moiety. Such moieties may be of any size or branch configuration. In one aspect, the PEG moiety may be conjugated to the 5' terminus of the nucleic acid aptamer. In another aspect, the PEG moiety may be conjugated to the 3' terminus of the nucleic acid aptamer. In one aspect, the synthetic polynucleotide is SEQ ID NO: 3.

Further provided herein are complementary synthetic polynucleotides which are capable of hybridizing with, or binds to, in whole or in part any of the VWF protective agents described above. In one aspect, the complementary synthetic polynucleotide may comprise at least 12 contiguous nucleotides of SEQ ID NO: 4. In another aspect, the complementary synthetic polynucleotide may comprise at least 15 contiguous nucleotides of SEQ ID NO: 4. In yet another aspect, the complementary synthetic polynucleotide may comprise at least 18-22 contiguous nucleotides of SEQ ID NO: 4.

The complementary synthetic polynucleotides may be chemically modified. Chemical modifications may be made to at least one nucleotide of the complementary synthetic polynucleotide. In some aspects, each of the nucleotides contains at least one chemical modification. The chemical modification may be a 2'-O-methyl modification to a nucleotide sugar. The complementary synthetic polynucleotides may further comprise a 3' terminal cap. In one aspect, the 3' terminal cap may be an inverted deoxythymidine.

In some embodiments, the complementary synthetic polynucleotide comprises SEQ ID NO: 5.

Further provided herein are methods of preventing dissociation of VWF multimers in a sample such as whole blood or plasma or within a medical or surgical device which is subject to hemodynamic flow. While dissociation of multimers may, in part, leave functional VWF species, in some instances dissociation can result in reduced function. As such, VWF protective agents may function to mitigate this loss in or reduction of function.

In some embodiments, provided are uses of the synthetic polynucleotides or complementary synthetic polynucleotides described herein in preparation of a medicament for the treatment of a disease, disorder or complication relating to VWF. In one aspect, the disorder is a thrombotic disorder. In one aspect, the thrombotic disorder is ischemic stroke.

In other embodiments, provided are uses of the synthetic polynucleotides or complementary synthetic polynucleotides described herein in preparation of a medicament for the treatment of a VAD associated complication or disorder. In one aspect, the complication or disorder may be acquired Von Willebrand Syndrome (aVWS), angiodysplasia, occlusive thrombosis, or VAD-associated pump thrombosis.

In other embodiments, provided are uses of any of the synthetic polynucleotides or complementary synthetic polynucleotides described herein in preparation of a medicament for the treatment of a complication or disorder which comprises aberrant binding of VWF to erythrocytes. In one aspect, the complication or disorder may be sickle cell disease.

In other embodiments, provided are uses of any of the synthetic polynucleotides or complementary synthetic polynucleotides described herein in preparation of a medicament for the treatment of a complication or disorder associated with gastrointestinal (GI) bleeding associated with angiodysplasia.

In other embodiments, provided are uses of any of the synthetic polynucleotides or complementary synthetic polynucleotides described herein in preparation of a medicament for restoring vessel patency in a subject having one or more vessel(s) occluded with at least one occlusive thrombus, wherein the vessel(s) are at least 50% occluded, the method comprising contacting said subject with a VWF protective agent such that vessel patency is restored.

In other embodiments, provided are uses of any of the synthetic polynucleotides or complementary synthetic polynucleotides described herein in preparation of a medicament for disaggregating one or more occlusive thrombi in a subject having at least one vessel that is at least 50% occluded. Such method includes contacting the subject with a VWF protective agent such that the one or more occlusive thrombi are disaggregated.

In certain embodiments of any of the above methods relating to occlusive thrombosis, the agent disaggregates the external layer of the occlusive thrombi. In certain embodiments of any of the above methods relating to occlusive thrombosis, the occlusive thrombi are formed under conditions of shear rates that are 10,000 $s^{-1}$ or greater. In certain embodiments of any of the above methods relating to occlusive thrombosis, the occlusive thrombi are resistant to fibrinolysis and/or antithrombotic agents. Diseases or disorders arising from the formation of occlusive thrombi may include an acute coronary syndrome, acute occlusion thrombosis, and ischemic stroke.

Further provided are uses of any of the synthetic polynucleotides or complementary synthetic polynucleotides described herein in preparation of a medicament for preventing platelet aggregation in a subject having a thrombotic disorder or complication. The synthetic polynucleotide may be administered via intravenous injection or subcutaneous injection. In one aspect, the bioavailability of subcutaneous injection is at least 85% relative to intravenous injection. In another aspect, the bioavailability of subcutaneous injection is at least 95% relative to intravenous injection. In some embodiments, the synthetic polynucleotide may be administered at a dose of from about 0.01 mg/kg to about 0.5 mg/kg of the subject body weight. The synthetic polynucleotide may have a plasma half-life of from about 70 hours to about 100 hours. In some embodiments, the synthetic polynucleotide may not function as an anticoagulant. The synthetic polynucleotide may not prolong clotting time and/or alter thrombin generation. In one aspect, the thrombotic disorder or complication is myocardial infarction. In other aspect, the thrombotic disorder or complication is ischemic stroke.

In some embodiments are provided methods of treating thrombotic disorders and complications thereof, comprising contacting a patient diagnosed with said disorder or complication with any of the VWF protective agents of the invention. In one aspect, the thrombotic disorder is ischemic stroke.

In some embodiments are provided methods of treating a VAD associated complication or disorder, such as, for example, aVWS and occlusive thrombosis, comprising contacting a patient diagnosed with said complication or disorder with any of the VWF protective agents of the invention. In certain embodiments, the thrombosis occurs in the VAD instrument. In other embodiments, occlusive thrombosis occurs in the lumen of a cardiovascular or cerebrovascular vessel in a VAD patient or a non-VAD subject. In some instances, it may also be necessary to reverse or titrate the effects of the present VWF protective agents. In this case, the present invention provides certain reversal agents.

In other embodiments, are provided methods for treating diseases or disorders arising from aberrant interactions of VWF with erythrocytes using VWF protective agents. In certain embodiments, the erythrocytes are sickle cells. The treatment of such diseases or disorders may be in combination with a VAD treatment or independent of a VAD treatment.

In other embodiments, are provided methods of treating a complication or disorder which comprises gastrointestinal bleeding associated with angiodysplasia with a VWF protective agent, in combination with a VAD treatment or independent of a VAD treatment.

In other embodiments, are provided methods of treating a complication or disorder which comprises thrombosis associated with VAD treatment with a VWF protective agent. In one embodiment, occlusive thrombus formation can occur in one or more of the patient's vessels. In another embodiment, thrombus formation can occur in the VAD instrument itself. Additionally, provided are methods for disaggregating one or more thrombi in a VAD patient comprising contacting a VAD patient with a VWF protective agent. Further provided are methods for decreasing the rate of thrombosis in a VAD patient comprising contacting a VAD patient with a VWF protective agent such that the rate of thrombosis is decreased relative to the rate of thrombosis in an untreated VAD patient.

In other embodiments, are provided methods of treating a complication or disorder which comprises occlusive thrombus formation associated with very high shear rate ($\geq 10,000$ $s^{-1}$), such as the shear rate found in an occluded vessel, with a VWF protective agent. The occlusive thrombus formation can occur in one or more of the subject's vessels.

Additionally, provided are methods for restoring vessel patency in a subject having one or more occluded vessels comprising contacting said subject with a VWF protective agent. Also provided are methods for disaggregating occlusive thrombi in one or more occluded vascular vessels comprising contacting a subject having at least one occluded vessel with a VWF protective agent. Further provided are methods for decreasing the rate of vessel occlusion in a subject comprising contacting said subject with a VWF protective agent such that the rate of vessel occlusion is decreased relative to the rate of vessel occlusion in an untreated subject.

In certain embodiments of any of the above methods relating to occlusive thrombosis, the one or more vessels are at least 50% occluded. In certain embodiments of any of the above methods relating to occlusive thrombosis, the agent disaggregates the external layer of the occlusive thrombi. In certain embodiments of any of the above methods relating to occlusive thrombosis, the occlusive thrombi are formed under conditions of shear rates that are 10,000 $s^{-1}$ or greater. In certain embodiments of any of the above methods relating to occlusive thrombosis, the occlusive thrombi are resistant to fibrinolysis and/or antithrombotic agents.

Further provided are methods for treating diseases or disorders arising from the formation of occlusive thrombi in a vascular vessel. In certain embodiments, the disease or disorder is acute occlusion thrombosis or an acute coronary syndrome, including, for example, myocardial infarction and unstable angina. In other embodiments, the disease or disorder is ischemic stroke.

In further embodiments, are provided uses for any of the synthetic polynucleotides or complementary synthetic polynucleotides described herein in preparation of a medicament for the treatment of central nervous system (CNS) thrombosis associated with severe and/or cerebral malaria.

In further embodiments, are provided uses for any of the synthetic polynucleotides or complementary synthetic polynucleotides described herein in preparation of a medicament for the treatment of gastrointestinal (GI) bleeding associated with Heyde's Syndrome.

BRIEF DESCRIPTION OF THE DRAWINGS

The foregoing and other objects, features and advantages will be apparent from the following description of particular embodiments of the invention, as illustrated in the accompanying drawings. The drawings are not necessarily to scale, emphasis instead being placed upon illustrating the principles of various embodiments of the invention.

FIG. 2 discloses SEQ ID NOs 3 and 12, respectively, in order of appearance.

FIG. 4 is a schematic drawing depicting the sequential steps of thrombus formation. FIG. 4A shows the initial stage of thrombus formation at <50% occlusion under physiological shear stress with platelet-platelet cross-linking involving mainly GpIIb/IIIa interaction. FIG. 4B shows the next step of thrombus formation at ≥50% occlusion under very high shear stress with platelet-platelet cross-linking involving mainly GpIbα-VWF interaction. FIG. 4C shows the next step of fully occlusive thrombosis (100% occluded) which in the early stages is resistant to GpIIb/IIIa inhibitors and sensitive to inhibitors of the GpIbα-VWF interaction.

DETAILED DESCRIPTION OF THE INVENTION

Figure 1:
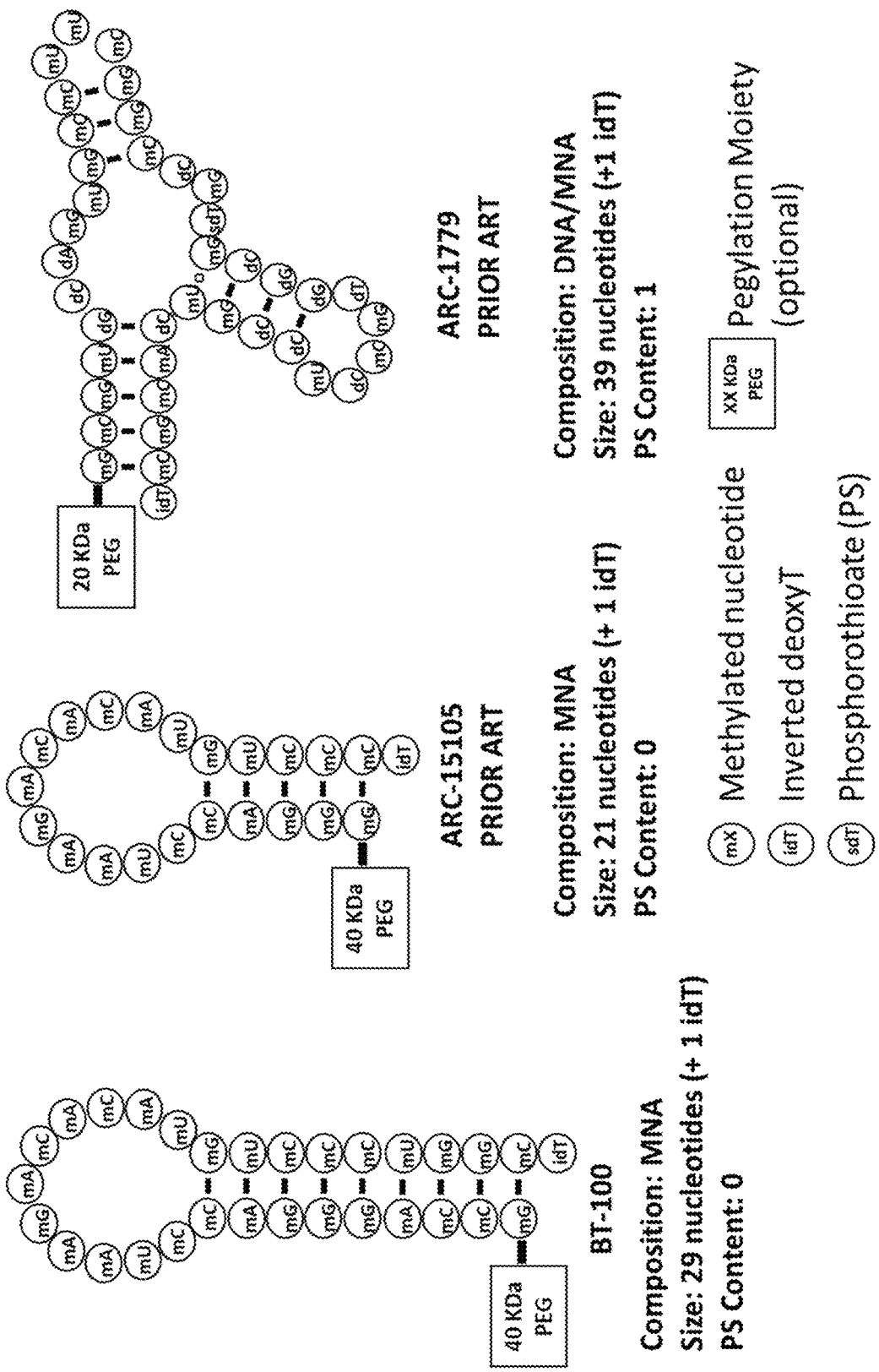
FIG. 1 is a diagram illustrating three aptamer constructs. BT-100 (SEQ ID NO: 2) of the present invention is shown for comparison to PRIOR ART compounds ARC15105 (SEQ ID NO: 6) and ARC1779 (SEQ ID NO: 7).

While the expert consensus is that the mechanical cause of the phenomenon is the hemodynamic shear force created by axial flow pumps acting on VWF, the fluid shear force created by a VAD is not alone sufficient to cause extensive proteolysis of VWF (Siediecki C A, et al., *Shear-dependent changes in the three-dimensional structure of human von Willebrand factor*. Blood 1996; 88(8):2939-2950; Schneider S W, et al. *Shear-induced unfolding triggers adhesion of von Willebrand factor fibers*. Proceedings of the National Academy of Sciences 2007; 104(19):7899-7903; Selgrade B P and Truskey G A. *Computational fluid dynamics analysis to determine shear stresses and rates in a centrifugal left ventricular assist device*. Artif Organs 2012; 36(4):E89-E96; Zheng Y, et al., *Flow-driven assembly of VWF fibres and webs in in vitro microvessels*. Nat Commun. 2015 Jul. 30; 6:7858; the contents of which are each incorporated herein by reference in their entirety).

For example, it is well known that platelet tethering to the A1 domain of VWF increases uncoiling under shear conditions and enhances VWF proteolysis and that drugs or biotherapeutic agents which bind to the A1 domain antagonize the VWF-platelet interaction (Shim K, et al., *Platelet-VWF complexes are preferred substrates of ADAMTS13 under fluid shear stress*. Blood 2008; 111(2):651-657; Nishio K, et al., *Binding of platelet glycoprotein Ibα to von Willebrand factor domain A1 stimulates the cleavage of the adjacent domain A2 by ADAMTS13*. Proceedings of the National Academy of Sciences of the United States of America 2004; 101(29): 10578-10583; Huang R H, et al., *A structural explanation for the antithrombotic activity of ARC1172, a DNA aptamer that binds von Willebrand factor domain A1*. Structure 2009; 17(11): 1476-1484; Siller-Matula J M, et al., *ARC15105 Is a Potent Antagonist of Von Willebrand Factor Mediated Platelet Activation and Adhesion*. Arteriosclerosis, Thrombosis, and Vascular Biology 2012; 32(4):902-909; and Diener J L, et al., *Inhibition of von Willebrand factor-mediated platelet activation and thrombosis by the anti-von Willebrand factor A1-domain aptamer ARC1779*. Journal of Thrombosis and Haemostasis 2009; 7(7):1155-1162; the contents of which are each incorporated herein by reference in their entirety). In addition, it was known that VWF-platelet interactions mediate occlusive thrombi formation under very high shear rates, such as shear rates observed in VAD treatment. Blockage of the interaction between VWF (A1 domain) and its ligand on platelets (GpIb) slows the rate of occlusive thrombi formed under very high shear rates and dissolves already-formed occlusive thrombi. Le Behot A, et al., *GpIbα-VWF blockade restores vessel patency by dissolving platelet aggregates formed under very high shear rate in mice*, Blood, 2013: Feb. 19, 2014; DOI 10.1182/blood-2013-12-543074; Starling R C, et al., *Unexpected Abrupt Increase in Left Ventricular Assist Device Thrombosis*, 2014, N. Engl. J Med., 370:33-40; Capoccia M, et al., *Recurrent Early Thrombus Formation in Heartmate II Left Ventricular Assist Device*, 2013, J. Inv. Med., 1:DOI:10, 1177/2324709613490676; Meyer A L, et al., *Thrombus Formation in a Heartmate II Left Ventricular Assist Device,* 2008, J. Thorac Cardiovasc Surg, 135:203-204; the contents of which are each incorporated herein by reference in their entirety.

On this background, the present inventors hypothesized that administration of a VWF antagonist should prevent and/or ameliorate VAD-associated complications and/or disorders or side effects, such as aVWS and occlusive thrombosis.

The therapeutic utility of Von Willebrand Factor antagonists has been demonstrated in diseases of excessive activation of VWF-platelet binding. One such example is a thrombotic disorder known as Thrombotic Thrombocytopenic Purpura (TTP), in which failure of proteolysis of high molecular weight multimers of VWF leads to their accumulation, which in turn may cause disseminated intravascular thrombosis. Administration of a VWF antagonist to patients with TTP has been demonstrated to correct thrombocytopenia, a hallmark of this disease, and clinical experiments to demonstrate improvement of clinical outcome by this means are underway.

Another example of the therapeutic utility of VWF antagonism is in treatment of a rare, inherited disorder known as Von Willebrand Disease Type 2b (VWD Type 2b). Patients with this disease have a mutation in the A1 domain of VWF that renders it constitutively active, eliminating the normal requirement for activation of VWF by hemodynamic shear force. As a result of this unregulated activation of VWF and binding of platelets these patients develop thrombocytopenia and reduced levels of high molecular weight multimers of VWF, and are prone to spontaneous mucocutaneous bleeding (especially epistaxis or menorrhagia).

Administration of a VWF antagonist to patients with VWD Type 2b has been demonstrated to correct their thrombocytopenia and to normalize their high molecular weight VWF multimer mass (See Jilma-Stohlawetz P, et al., *A dose ranging phase I/II trial of the von Willebrand factor inhibiting aptamer ARC1779 in patients with congenital thrombotic thrombocytopenic purpura*. Thromb Haemost 2011; 106(3); Jilma-Stohlawetz P, et al., *Inhibition of von Willebrand factor by ARC1779 in patients with acute thrombotic thrombocytopenic purpura*. Thromb Haemost 2011; 105(3):545-552; US Publication 2009/0203766; International Publication WO2010/091396 and Jilma-Stohlawetz P, et al., *The anti-von Willebrand factor aptamer ARC1779 increases von Willebrand factor levels and platelet counts in patients with type 2B von Willebrand disease*. Thromb Haemost 2012; 108(2), the contents of which are each incorporated herein by reference in their entirety).

Yet given all of the foregoing there is still no satisfactory treatment of acquired Von Willebrand Syndrome (aVWS) that occurs in patients after VAD implantation. In theory, one might surmise that administration of exogenous VWF from donor plasma concentrates that contain VWF or from recombinant sources (not yet commercially available) could transiently restore high molecular weight VWF multimer levels. However, administration of exogenous VWF would not correct the underlying problem resulting from the causal chain starting with mechanically-induced elevated shear force causing inappropriate activation of VWF, in turn causing excessive platelet binding to VWF in turn causing exposure of VWF to proteolysis which results in a deficiency of functional VWF multimers. Other than removing the source of shear force (i.e., the VAD), which patients depend upon for hemodynamic support, the next best way to interrupt this causal chain would be to preserve the multimers themselves as proposed herein, by any of several ways including, but not limited to, blocking the binding of platelets to the shear-force-activated and partially uncoiled VWF multimers.

One of skill might also suggest that the compounds found to be useful in Thrombotic Thrombocytopenic Purpura or Von Willebrand Disease Type 2b (VWD Type 2b) such as ARC1779 or ARC15105 noted above may be effective. The present inventor has surprisingly discovered that this is not the case.

It has been found that sickle cell disease at baseline is associated with high concentrations of hyperadhesive VWF, which correlates closely with the rate of hemolysis (Chen J, et al. *The rate of hemolysis in sickle cell disease correlates with the quantity of von Willebrand factor in the plasma*. Blood 2011, 117, 3680-3683; the contents of which are incorporated herein by reference in their entirety). Thus, VWF represents a therapeutic target to ameliorate hemolysis in sickle cell disease, either in combination with VAD treatment or independently of VAD treatment.

Along with its role in maintenance of hemostasis (i.e., arresting hemorrhage), VWF has been implicated in a number of processes in the vasculature, including the vascular inflammation and smooth muscle cell proliferation. VWF is also known to be a negative regulator of angiogenesis. As used herein, "angiogenesis" is defined as the formation of new blood vessels. VWF has been found to act as a "brake" by constraining angiogenesis, through control of VEGFR2 signaling (Starke R D, et al., *Endothelial von Willebrand factor regulates angiogenesis*. Blood, 2011, 117:1071-80; the contents of which are each incorporated herein by reference in their entirety).

Bleeding from the GI tract in VAD patients is known to be caused by angiodysplasia (Islam S, et al, *Left ventricular assist devices and gastrointestinal bleeding: a narrative review of case reports and case series*. Clin Cardiol. 2013, 36:190-200 and Suarez J, Patel C B, Felker G M, Becker R, Hernandez A F, Rogers J G. *Mechanisms of bleeding and approach to patients with axial-flow left ventricular assist devices*. Circ. Heart Fail. 2011 4:779-84 and references therein; the contents of which are incorporated herein by reference in their entirety). "Angiodysplasia" as used herein, is defined as vascular malformations in the GI tract which are associated with dysregulated angiogenesis.

Without wishing to be bound by theory, systemic depletion of VWF through proteolysis of VWF multimers caused by exposure to the hemodynamic shear forces may lead to a reduction of VWF in the vascular endothelium of the GI tract and result in angiodysplasia in VAD patients. Thus, through its roles in maintaining hemostasis and/or constraining angiogenesis, functional VWF may be critical to maintaining healthy vascular endothelium in the GI tract.

The present invention provides VWF agents compositions and methods which prevent depletion of VWF in the vascular endothelium. In some embodiments, these compositions prevent formation of vascular malformations in the GI tract and GI bleeding in VAD patients. In head-to-head studies described herein, the inventors demonstrate that protection of VWF multimers is provided by an aptamer distinct from those in the art.

It is known that interactions between platelet glycoprotein IIb/IIIa (GpIIb/IIIa) and plasma proteins mediate platelet cross-linking in arterial thrombi. However, past studies show that GpIIb/IIIa inhibitors do not significantly impact the patency of pre-occluded arteries, failing to disperse platelet aggregates after myocardial infarction or ischemic stroke (Mehilli J, et al., *Abciximab in patients with acute ST-segment-elevation myocardial infarction undergoing primary percutaneous coronary intervention after clopidogrel loading: a randomized double-blind trial*. Circulation. 2009; 119(14):1933-1940; Kleinschnitz C, et al., *Targeting platelets in acute experimental stroke: impact of glycoprotein Ib, VI, and IIb/IIIa blockade on infarct size, functional outcome, and intracranial bleeding*. Circulation. 2007; 115(17):2323-2330; Adams H P Jr, et al; AbESTT-II Investigators, *Emergency administration of abciximab for treatment of patients with acute ischemic stroke: results of an international phase III trial: Abciximab in Emergency Treatment of Stroke Trial (AbESTT-II)*. Stroke. 2008; 39(1):87-99; Kellert L, et al., *Endovascular stroke therapy: tirofiban is associated with risk of fatal intracerebral hemorrhage and poor outcome*. Stroke. 2013; 44(5): 1453-1455; the contents of which each are incorporated herein by reference in their entirety.

On the other hand, studies have demonstrated that blockade of the interaction between GpIbα and VWF leads to reperfusion after photothrombosis-induced stroke in guinea pigs (whereas GpIIb/IIIa inhibitors are ineffective). Momi S, et al., *Reperfusion of cerebral artery thrombosis by the GPIb-VWF blockade with the Nanobody ALX-0081 reduces brain infarct size in guinea pigs*. Blood. 2013; 121(25): 5088-5097; the contents of which are incorporated herein by reference in their entirety. Likewise, additional studies have shown the beneficial effect of GpIbα-VWF targeting through inhibition of the post-reperfusion thrombo-inflammatory reaction in transient mechanical stroke models. Kleinschnitz C, et al., *Deficiency of von Willebrand factor protects mice from ischemic stroke*. Blood. 2009; 113(15): 3600-3603; Pham M, et al., *Sustained reperfusion after blockade of glycoprotein-receptor-Ib in focal cerebral ischemia: an MRI study at 17.6 Tesla*. PLoS One. 2011; 6(4): e18386; Stoll G, et al., *The role of glycoprotein Ibalpha and von Willebrand factor interaction in stroke development*. Hamostaseologie. 2010; 30(3):136-138; Kleinschnitz C, et al., *Targeting platelets in acute experimental stroke: impact of glycoprotein Ib, VI, and IIb/IIIa blockade on infarct size, functional outcome, and intracranial bleeding*. Circulation. 2007; 115 (17):2323-2330; the contents of which each are incorporated herein by reference in their entirety.

Recently, computational fluid dynamic (CFD) simulations of the blood flow in the middle cerebral artery at different stages of development, as well as in vivo thrombotic stroke models have demonstrated that platelet cross-linking during closure of the vessel lumen is dependent on GpIbα-VWF interactions and that disruption of GpIbα-VWF interactions restores vessel patency by specifically disaggregating the external layer of occlusive thrombi, which contains platelet aggregates formed under very high shear rates (10,000 $s^{-1}$ or greater). Le Behot A, et al., *GpIbα-VWF blockade restores vessel patency by dissolving platelet aggregates formed under very high shear rate in mice*. Blood, 2013: Feb. 19, 2014; DOI 10.1182/blood-2013-12-543074; the contents of which are incorporated herein by reference in their entirety.

It has been further demonstrated that occlusive thrombus formation occurs in three distinct stages of development, in which each stage is subjected to different local shear rates and regulated by different mechanisms, resulting in three different regions of occlusive thrombi as follows: (1) the base of the thrombus that is exposed to shear rates below 1,500 $s^{-1}$ throughout the entire thrombotic process (fibrin); (2) the core of the thrombus, corresponding to the portion of the thrombus formed during the first steps of development (0% to <50% occlusive thrombus formation) at shear rates between about 1500 $s^{-1}$ and about 10,000 $s^{-1}$ (see FIG. 4A); and (3) the external layer of the thrombus, which is formed during the last step(s) of thrombus formation (≥50% to 100% occlusive thrombus formation) at very high shear rates (10,000 s$^{-1}$ or greater) (see FIG. 4B) and is responsible for vessel lumen closure (see FIG. 4C). The core of the thrombus is primarily made up of platelets cross-linked by GpIIb/IIIa-dependent interactions, whereas formation of the external layer of the thrombus is dependent upon GpIbα-VWF interactions. Le Behot A, et al., Blood, 2013: Feb. 19, 2014; DOI 10.1182/blood-2013-12-543074.

Shear-dependent thrombogenesis caused by GpIbα-VWF interactions occurs in stenotic coronary arteries or ruptured atherosclerotic plaque lesions (Sadler J E. *Biochemistry and genetics of von Willebrand factor.* Annu Rev Biochem. 1998; 67:395-424; the contents of which are incorporated herein by reference in their entirety). VWF levels are also heightened in patients, who experienced adverse cardiac events that are linked to a poorer prognosis (Collet J P, et al., Acute release of plasminogen activator inhibitor-1 in ST-segment elevation myocardial infarction predicts mortality. Circulation. 2003; 108:391-394; Fuchs I, et al., *Platelet function in patients with acute coronary syndrome (ACS) predicts recurrent ACS.* J Thromb Haemost. 2006; 4:2547-2552; Thompson S G, et al., *Hemostatic factors and the risk of myocardial infarction or sudden death in patients with angina pectoris. European Concerted Action on Thrombosis and Disabilities Angina Pectoris Study Group.* N Engl J Med. 1995; 332:635-641; the contents of which each are incorporated herein by reference in their entirety). Conventional therapy of myocardial infarction reduces platelet activation and aggregation, but mostly addresses receptors and targets other than VWF. Targeting the initial adhesion steps, by antagonizing either GpIb or collagen binding might be very powerful in the development of antiplatelet drugs, especially since little redundancy for these interactions can be found. Furthermore, due to the specific requirement of the GpIb-VWF interaction in high shear conditions, the arterial side can be targeted without interfering with the venous system, therefore probably reducing the risk of bleeding problems, which is the most prominent side-effect of currently used antiplatelet drugs. In addition, drugs that interfere with platelet adhesion would have the extra advantage of reducing platelet activation and secretion, which might even turn out to be beneficial in the prevention of restenosis (De Meyer S F, et al., *Antiplatelet drugs.* British Journal of Haematology, 142, 515-528; the contents of which are incorporated herein by reference in their entirety).

The present disclosure provides VWF agents, compositions and methods which disaggregate occlusive thrombi formed under very high shear rates, such as shear rates found in pre-occluded vessels or in VAD treatment. In particular, the VWF agents dissolve occlusive thrombi containing platelet aggregates formed under shear rates of 10,000 s$^{-1}$ or greater, i.e., those found in the external layer of the occlusive thrombus. These agents and compositions restore vessel patency in patients having acute occlusion thrombosis or acute coronary syndrome, including, for example, myocardial infarction and unstable angina. In other embodiments, the agents and compositions restore vessel patency in patients who have suffered an ischemic stroke. In other embodiments, the agents and compositions restore vessel patency in VAD patients. In other embodiments, the agents and compositions disaggregate one or more thrombi in the VAD instrument.

The present disclosure also provides VWF agents, compositions and methods which slow the development of occlusive thrombi formed under very high shear rates, such as shear rates found in pre-occluded vessels or in VAD treatment. In particular, the VWF agents slow the development of occlusive thrombi containing platelet aggregates formed under shear rates of 10,000 s$^{-1}$ or greater, i.e., those found in the external layer of occlusive thrombi. In other embodiments, the agents and compositions slow the development of thrombi in the VAD instrument.

The present disclosure also provides VWF agents, compositions and methods for decreasing the rate of vessel occlusion in a subject having one or more vessel(s) that are at least 50% occluded with one or more occlusive thrombi, the method comprising contacting the subject with a VWF protective agent such that the rate of vessel occlusion is decreased relative to the rate of vessel occlusion in an untreated vessel that is at least 50% occluded.

In additional embodiments, the VWF agents, compositions and methods of the present disclosure may be useful for treating or preventing an orphan disease or indication associated with VWF, such as, but not limited to, severe and/or cerebral malaria, and Heyde's Syndrome.

Severe malaria is a life-threatening condition of *Plasmodium falciparum*: infection where the infection is complicated with serious failure of the body's major organs. Sometimes severe malaria is associated with coma and is known as cerebral malaria. Elevated levels of VWF, VWF propeptide (markers of chronic and acute endothelial cell activation, respectively), and activated VWF have been identified in the plasma of patients with cerebral malaria (Hollestelle M J, et al., *von Willebrand factor propeptide in malaria: evidence of acute endothelial cell activation.* Br J Haematol. 2006; 133(5):562-9; de Mast Q, et al., *Thrombocytopenia and release of activated von Willebrand Factor during early Plasmodium falciparum malaria.* J Infect Dis. 2007; 196(4):622-8; the contents of which each are incorporated herein by reference in their entirety). This is supported by additional studies revealing that severe malaria is also associated with a deficiency of the VWF cleaving protease, ADAMTS13, and an accumulation of hyperreactive ultra-large VWF multimers (de Mast Q, et al. *ADAMTS13 deficiency with elevated levels of ultra-large and active von Willebrand factor in P. falciparum and P. vivax malaria.* Am J Trop Med Hyg. 2009; 80(3):492-8; Larkin D, et al. *Severe Plasmodium falciparum: malaria is associated with circulating ultra-large von Willebrand multimers and ADAMTS13 inhibition.* PLoS Pathog. 2009; 5(3):e1000349; Lowenberg E C, et al. *Severe malaria is associated with a deficiency of von Willebrand factor cleaving protease, ADAMTS13.* Thromb Haemost. 2010; 103(1): 181-7; the contents of which each are incorporated herein by reference in their entirety). A recent study further demonstrated that VWF plays an active role in modulating malaria pathogenesis, possibly by sequestering platelets, recruiting malaria-infected red blood cells, inducing increased endothelial cell permeability, and eventually causing central nervous system (CNS) thrombosis (O'Regan N, et al. *A novel role for von Willebrand factor in the pathogenesis of experimental cerebral malaria.* Blood. 2016; 127(9):1192-201; Montgomery, R. R., *The heads and the tails of malaria and VWF.* Blood, 2016. 127(9): p. 1081-2; the contents of which each are incorporated herein by reference in their entirety). In light of these findings, the present inventors anticipate that disruption the interaction of VWF with platelets using the VWF agents of the present invention may prevent thrombus formation or disaggregate platelet-rich thrombi in cerebral malaria.

Heyde's Syndrome is a syndrome of gastrointestinal bleeding from angiodysplasia in the presence of aortic stenosis. Loss of high-molecular-weight multimers of VWF has been identified as a link between GI bleeding and aortic stenosis (Warkentin T E, et al. *Aortic stenosis and bleeding gastrointestinal angiodysplasia: is acquired von Willebrand's disease the link?* Lancet. 1992; 340(8810):35-7), and has been reported to be present in 67-92% of patients with severe aortic stenosis (Vincentelli A, et al. *Acquired von Willebrand syndrome in aortic stenosis*. N Engl J Med. 2003 Jul. 24; 349(4):343-9; the contents of which are incorporated herein by reference in their entirety). Moreover, VWF activity is significantly correlated with the severity of stenosis and the rate of bleeding (Blackshear J L, et al. *Indexes of von Willebrand factor as biomarkers of aortic stenosis severity (from the Biomarkers of Aortic Stenosis Severity [BASS] study)*. Am J Cardiol. 2013; 111(3):374-81; the contents of which are incorporated herein by reference in their entirety). It is thought that high shear stress caused by valve obstruction leads to changes in the structure of VWF multimers, increasing their proteolysis by the protease ADAMTS13 (Vaz A, et al. *Heyde syndrome—the link between aortic stenosis and gastrointestinal bleeding*. Rev Port Cardiol. 2010 February; 29(2):309-14; Loscalzo J. *From clinical observation to mechanism—Heyde's syndrome*. N Engl J Med. 2012; 367(20): 1954-6; the contents of which each are incorporated herein by reference in their entirety). This is supported by the fact that aortic valve replacement restores the VWF abnormalities and decreases the rick of GI bleeding. There is also increased interaction between platelets and VWF with the formation of platelet microaggregates that are associated with increased degradation and clearance of VWF multimers. According to the present disclosure, VWF agents described herein can protect the loss of VWF multimers and/or antagonizes the interaction of VWF with platelets, thereby preventing GI bleeding in patients with Heyde's Syndrome.

I. Compositions of the Invention

Provided herein are compounds, compositions (including pharmaceutical compositions) and methods for the design, preparation, use and manufacture of compounds which prevent and/or ameliorate conditions associated with, or side effects of, utilization of ventricular assist devices (VADs, including left VAD or LVAD) such as LVAD-associated angiodysplasia, acquired Von Willebrand Syndrome (aVWS), Type 2 VWD and other cardiovascular and cerebrovascular disorders such as acute coronary syndrome, acute occlusion thrombosis, stroke, aneurism, and ischemic events, as well as sickle cell disease, severe and/or cerebral malaria, and Heyde's Syndrome, either in combination with VAD treatment or independently of VAD treatment.

In some embodiments, the VWF protective agent may be used to treat GI bleeding associated with angiodysplasia. In some embodiments, the VWF protective agent may be used to treat a VAD patient with GI bleeding.

As such, the compounds and/or compositions of the invention interact with or bind to VWF monomers or multimers in a way that preserves, protects or prevents the loss, reduction or destruction of VWF multimers and/or antagonizes the interaction of VWF multimers with erythrocytes such as sickle cells for example. The compounds and/or compositions can also antagonize the interaction of VWF monomers and/or multimers with platelets such that occlusive thrombi in pre-occluded vessels are disaggregated. As used herein, such protective compounds or compositions are referred to as "VWF multimer protective agents" or "VWF protective agents."

In some embodiments, the VWF protective agent may interact with or bind to VWF monomers or multimers in a way that preserves, protects or prevents the loss, reduction or destruction of VWF multimers to restore VWF mediated constraint on angiogenesis in vascular endothelial cells and prevent neovascularization in a VAD patient.

In other embodiments, the VWF protective agent can be used to restore vessel patency in a subject having one or more pre-occluded vessels, such as subjects with acute occlusion thrombosis or acute coronary syndrome, including, for example, myocardial infarction and unstable angina, or ischemic stroke. Under these conditions, the compounds and/or compositions interact with or bind to VWF in a way that antagonizes the interaction of VWF with platelets such that occlusive thrombi in pre-occluded vessels (vessels that are at least 50% occluded) are disaggregated. In certain embodiments, the VWF protective agent disaggregates the external layer of the occlusive thrombi. In certain embodiments, the occlusive thrombi that are disaggregated are formed under conditions of shear rates of 10,000 $s^{-1}$ or greater (that is, the occlusive thrombi contain platelet aggregates formed under very high shear rates of 10,000 $s^{-1}$ or greater). In some embodiments, the occlusive thrombi are resistant to fibrinolysis and/or antithrombotic agents. In other embodiments, the VWF protective agents can be used to restore vessel patency in a subject undergoing VAD treatment.

In further embodiments, the VWF protective agent can be used to decrease the rate of vessel occlusion in a subject comprising contacting said subject with a VWF protective agent such that the rate of vessel occlusion is decreased relative to the rate of vessel occlusion in an untreated vessel. In other embodiments, the VWF protective agents can be used to decrease the rate of vessel occlusion in a subject undergoing VAD treatment.

As used herein, the term "occlusive thrombus" or "occlusive thrombi" refers to a thrombus or thrombi containing platelet aggregates formed under very high shear rates (10,000 $s^{-1}$ or greater). Such occlusive thrombus or thrombi are formed during the closure of the vessel lumen, i.e., when the lumen is at least 50% occluded. As used herein, the term "pre-occluded vessel(s)" or "occluded vessel(s)" refers to a vessel(s) that is at least 50% occluded and can include fully occluded vessel(s). The term "fully occluded vessel(s)" refers to a vessel(s) that is 100% occluded or, in other words, a vessel with a closed lumen.

As used herein, the term "thrombotic disorder" refers to any disease or disorder characterized by abnormal thrombus formation. In one embodiment, the abnormal thrombus formation characterizing the disorder is the formation of one or more occlusive thrombi. Non-limiting examples of thrombotic disorders include von Willebrand's Disease, ischemic stroke, acute coronary syndrome, myocardial infarction, transient ischemic attack, thrombotic thrombocytopenic purpura, and thrombotic microangiopathies. A thrombotic disorder may occur either in combination with VAD treatment or independently of VAD treatment. In one embodiment, the thrombotic disorder is ischemic stroke.

In additional embodiments, the VWF protective agent can be used to treat an orphan disease associated with VWF abnormality, such as, but not limited to, severe and/or cerebral malaria, and Heyde's Syndrome.

In one embodiment, the VWF protective agent can be used to antagonize the interaction of VWF with platelets in a subject with severe and/or cerebral malaria such that the CNS thrombus formation is prevented or reduced.

In another embodiment, the VWF protective agent can be used to treat GI bleeding associated with Heyde's Syndrome. The VWF protective agent may prevent or reduce the loss of VWF multimers and/or antagonize the interaction of VWF with platelets, thereby preventing the GI bleeding in the subject with Heyde's Syndrome.

VWF Protective Agents: Aptamers

In some embodiments, the VWF protective agents of the invention comprise an aptamer.

As used herein, an "aptamer" is a biomolecule that binds to a specific target molecule and modulates the target's activity, structure, or function. An aptamer of the present invention may be nucleic acid or amino acid based. Nucleic acid aptamers have specific binding affinity to molecules through interactions other than classic Watson-Crick base pairing. Nucleic acid aptamers, like peptides generated by phage display or monoclonal antibodies (mAbs), are capable of specifically binding to selected targets and, through binding, block their targets' ability to function. In some cases, aptamers may also be peptide aptamers. As used herein, an "aptamer" specifically refers to either a nucleic acid aptamer or peptide aptamer.

Aptamers, often called "chemical antibodies," have similar characteristics as antibodies. A typical nucleic acid aptamer is approximately 10-15 kDa in size (20-45 nucleotides), binds its target with sub-nanomolar affinity, and discriminates against closely related targets.

Aptamers may be either monovalent or multivalent. Aptamers may be monomeric, dimeric, trimeric, tetrameric or other higher multimeric. Individual aptamer monomers may be linked to form multimeric aptamer fusion molecules. As a non-limiting example, a linking oligonucleotide (i.e., linker) may be designed to contain sequences complementary to both 5'-arm and 3'-arm regions of random aptamers to form dimeric aptamers. For trimeric or tetrameric aptamers, a small trimeric or tetrameric (i.e., a Holliday junction-like) DNA nanostructure will be engineered to include sequences complementary to the 3'-arm region of the random aptamers, therefore creating multimeric aptamer fusion through hybridization. In addition, 3 to 5 or 5 to 10 dT rich nucleotides can be engineered into the linker polynucleotides as a single stranded region between the aptamer-binding motifs, which offers flexibility and freedom of multiple aptamers to coordinate and synergize multivalent interactions with cellular ligands or receptors. Alternatively, multimeric aptamers can also be formed by mixing biotinylated aptamers with streptavidin.

As used herein, the term "multimeric aptamer" or "multivalent aptamer" refers to an aptamer that comprises multiple monomeric units, wherein each of the monomeric units can be an aptamer on its own. Multivalent aptamers have multivalent binding characteristics. A multimeric aptamer can be a homomultimer or a heteromultimer. The term "homomultimer" refers to a multimeric aptamer that comprises multiple binding units of the same kind, i.e., each unit binds to the same binding site of the same target molecule. The term "heteromultimer" refers to a multimeric aptamer that comprises multiple binding units of different kinds, i.e., each binding unit binds to a different binding site of the same target molecule, or each binding unit binds to a binding site on different target molecule. Thus, a heteromultimer can refer to a multimeric aptamer that binds to one target molecule at different binding sites or a multimeric aptamer that binds to different target molecules. A heteromultimer that binds to different target molecules can also be referred to as a multi-specific multimer.

Nucleic acid aptamers comprise a series of linked nucleosides or nucleotides.

The term "nucleic acid", in its broadest sense, includes any compound and/or substance that comprise a polymer of nucleotides. These polymers are often referred to as polynucleotides. Exemplary nucleic acid molecules or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure, the ribofuranosyl ring or in the ribose-phosphate backbone.

Nucleic acid aptamers may be ribonucleic acid, deoxyribonucleic acid, or mixed ribonucleic acid and deoxyribonucleic acid. Aptamers may be single stranded ribonucleic acid, deoxyribonucleic acid or mixed ribonucleic acid and deoxyribonucleic acid.

In one embodiment, the VWF protective agent may be an aptamer or salt thereof.

In one embodiment, the VWF protective agent may be an aptamer or salt thereof which may comprise synthetic polynucleotides. The synthetic polynucleotides may comprise at least 21 contiguous nucleotides of SEQ ID NO: 1. Additionally, the synthetic polynucleotides may exhibit a double stranded region having at least 6 base pairs. While not wishing to be bound by theory, shorter double stranded regions of 5 base pairs or less may lead to the unraveling of the stem-loop structure at higher temperatures and the associated loss of affinity and functionality of the protective agents.

In one embodiment, the VWF protective agent may be an aptamer or salt thereof which may comprise synthetic polynucleotides, where the synthetic polynucleotides comprise at least 21 contiguous nucleotides of SEQ ID NO: 1, and where the synthetic polynucleotides comprise a double stranded region having at least 6 base pairs. While not wishing to be bound by theory, VWF protective agents having a double stranded region of at least 6 base pairs may have greater thermostability at higher temperatures. This increased thermostability at higher temperatures may provide a greater affinity for VWF and increased functionality as compared to protective agents which a shorter double stranded region of 5 base pairs or less.

In one embodiment, the double stranded region of 6 or more base pairs is at or near (e.g., within 1-10 nucleotides) the termini of the synthetic polynucleotide.

In some embodiments, nucleic acid aptamers comprise at least one chemical modification. Modifications may be used to increase the stability of an aptamer, e.g., by increasing its resistance to degradation by ribonucleases (RNases) present in a cell, thereby causing its half-life in the cell to be increased. Modifications may also or alternatively be used to decrease the likelihood or degree to which aptamer introduced into cells elicit innate immune responses. Such responses, which have been well characterized in the context of RNA interference (RNAi), including small-interfering RNAs (siRNAs), as described in the art, tend to be associated with reduced half-life of the RNA and/or the elicitation of cytokines or other factors associated with immune responses.

Potential modifications include, but are not limited to, for example, (a) end modifications, e.g., 5' end modifications (phosphorylation, dephosphorylation, conjugation, inverted linkages, etc.), 3' end modifications (conjugation, DNA nucleotides, inverted linkages, etc.), (b) sugar modifications (e.g., at the 2' position or 4' position) or replacement of the sugar, (c) base modifications, e.g., replacement with modified bases, stabilizing bases, destabilizing bases, or bases that base pair with an expanded repertoire of partners, or conjugated bases, as well as (d) internucleoside linkage modifications, including modification or replacement of the phosphodiester linkages. Specific examples of modified aptamer compositions useful with the methods described herein include, but are not limited to, nucleic acid molecules containing modified or non-natural internucleoside linkages. Modified aptamer having modified internucleoside linkages include, among others, those that do not have a phosphorous atom in the internucleoside linkage. In other embodiments, modified aptamer has a phosphorus atom in its internucleoside linkage(s).

In some embodiments, the chemical modification is selected from a chemical substitution of the nucleic acid at a sugar position, a chemical substitution at a phosphate position and a chemical substitution at a base position. In other embodiments, the chemical modification is selected from incorporation of a modified nucleotide; 3' capping; 5' capping; conjugation to a high molecular weight, non-immunogenic compound; conjugation to a lipophilic compound; and incorporation of phosphorothioate into the phosphate backbone.

In one embodiment, each nucleotide of the nucleic acid aptamers may contain at least one chemical modification. Such chemical modification may be at the sugar, nucleobase or internucleoside linker of the synthetic polynucleotide. Modifications to the sugar may consist of a 2' O-methyl modification.

According to the nucleic acid aptamers provided by the present disclosure, terminal cap structures may also be incorporated to the 3' and/or 5' termini. Such structures include, but are not limited to, at least one inverted deoxythymidine or amino group ($NH_2$).

In one embodiment, the 3' cap is an inverted deoxythymidine cap.

In another embodiment, the 3' cap is an amino group ($NH_2$).

In one embodiment, the 5' cap is an inverted deoxythymidine cap.

In another embodiment, the 5' cap is an amino group ($NH_2$).

In one embodiment, VWF protective agents of the present invention may be modified by any number of conjugates. As a non-limiting example, the conjugates may be high molecular weight non-immunogenic compounds.

In one embodiment, the high molecular weight, non-immunogenic compound is polyalkylene glycol, and more preferably is polyethylene glycol (PEG).

In some embodiments, a PEG moiety is conjugated to the 5' terminus of the nucleic acid aptamer.

In some embodiments, a PEG moiety is conjugated to the 3' terminus of the nucleic acid aptamer.

As non-limiting examples, a nucleic acid aptamer can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside (e.g., β-D-ribo configuration, α-LNA having an α-L-ribo configuration (a diastereomer of LNA), 2'-amino-LNA having a 2'-amino functionalization, and 2'-amino-α-LNA having a 2'-amino functionalization), an abasic nucleoside, an inverted deoxynucleoside or inverted ribonucleoside, a 2'-deoxy-2'-fluoro modified nucleoside, a 2'-amino-modified nucleoside, a 2'-alkyl-modified nucleoside, a 2'-O-alkyl-modified nucleoside, a 2'-O-alkyl-O-alkyl-modified nucleoside, a 2'-fluoro-modified nucleoside, a 2'-fluoro-modified nucleoside, morpholino nucleoside, a phosphoramidate or a non-natural base comprising nucleoside, or any combination thereof. Alternatively, a nucleic acid aptamer can comprise at least two modified ribonucleosides, at least 3, at least 4, at least 5, at least 6, at least 7, at least 8, at least 9, at least 10, at least 15, at least 20 or more, up to the entire length of the molecule. The modifications need not be the same for each of such a plurality of modified deoxy- or ribonucleosides in a nucleic acid molecule.

Nucleic acid aptamers described herein may also contain one of the following at the 2' position: H (deoxyribose); OH (ribose); F; O—, S—, or N-alkyl; O—, S—, or N-alkenyl; O—, S- or N-alkynyl; or O-alkyl-O-alkyl, wherein the alkyl, alkenyl and alkynyl can be substituted or unsubstituted C1 to C10 alkyl or C2 to C10 alkenyl and alkynyl. Exemplary modifications include $O[(CH_2)_nO]_mCH3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In some embodiments, nucleic acid aptamers include one of the following at the 2' position: C1 to C10 lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, a reporter group, an intercalator, a group for improving the pharmacokinetic properties of an aptamer, or a group for improving the pharmacodynamic properties of a nucleic acid aptamer, and other substituents having similar properties. In some embodiments, the modification includes a 2' methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$.

Similar modifications may also be made at other positions on the aptamer, particularly the 3' position of the sugar on the 3' terminal nucleotide and the 5' position of 5' terminal nucleotide. Aptamers may also have sugar mimetics, such as cyclobutyls in place of the pentofuranosyl group. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

VWF protective agents which are nucleic acid based may include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993; the contents of which each are incorporated herein by reference in their entirety.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly $CH_2$—NH—O—$CH_2$, $CH_2$—N($CH_3$)—O—$CH_2$ (known as a methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones (wherein the native phosphodiester backbone is represented as O—P—O—$CH_2$—), amide backbones [see De Mesmaeker et al., Ace. Chem. Res., 28:366-374 (1995); which is incorporated by reference in its entirety]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497; which is incorporated by reference in its entirety). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050; the contents of which each are incorporated herein by reference in their entirety.

Morpholino-based oligomeric compounds are described in Braasch and David Corey, Biochemistry, 41(14): 4503-4510 (2002); Genesis, Volume 30, Issue 3, (2001); Heasman, Dev. Biol., 243: 209-214 (2002); Nasevicius et al., Nat. Genet., 26:216-220 (2000); Lacerra et al., Proc. Natl. Acad. Sci., 97: 9591-9596 (2000); and U.S. Pat. No. 5,034,506, issued Jul. 23, 1991, each of which is incorporated by reference in its entirety.

Cyclohexenyl nucleic acid oligonucleotide mimetics are described in Wang et al., J. Am. Chem. Soc., 122: 8595-8602 (2000), which is hereby incorporated by reference in its entirety. Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts; see U.S. Pat. Nos. 5,034,506; 5,166, 315; 5,185,444; 5,214,134; 5,216,141; 5,235,033; 5,264, 562; 5,264,564; 5,405,938; 5,434,257; 5,466,677; 5,470, 967; 5,489,677; 5,541,307; 5,561,225; 5,596,086; 5,602, 240; 5,610,289; 5,602,240; 5,608,046; 5,610,289; 5,618, 704; 5,623,070; 5,663,312; 5,633,360; 5,677,437; and 5,677,439, each of which is incorporated by reference in its entirety.

In some embodiments, nucleic acid aptamers are provided in which the P(O)O group is replaced by P(O)S ("thioate"), P(S)S ("dithioate"), P(O)NR$_2$ ("amidate"), P(O)R, P(O)OR', CO or $CH_2$ ("formacetal") or 3'-amine (—NH—$CH_2$—$CH_2$—), wherein each R or R' is independently H or substituted or unsubstituted alkyl. Linkage groups can be attached to adjacent nucleotide through an —O—, —N—, or —S— linkage. Not all linkages in the nucleic acid aptamers are required to be identical.

Additional modifications which may be useful in the nucleic acid aptamers of the invention include those taught in, for example, International Publication PCT/US2012/058519, the contents of which are incorporated herein by reference in their entirety.

A suitable nucleotide length for an aptamer ranges from about 15 to about 100 nucleotide (nt), and in various other preferred embodiments, 15-30 nt, 20-25 nt, 30-100 nt, 30-60 nt, 25-70 nt, 25-60 nt, 40-60 nt, 25-40 nt, 30-40 nt, any of 22, 23, 24, 25, 26, 27, 28, 29, 30, 31, 32, 33, 34, 35, 36, 37, 38, 39 or 40 nt or 40-70 nt in length. However, the sequence can be designed with sufficient flexibility such that it can accommodate interactions of aptamers with two targets at the distances described herein.

In some embodiments, the nucleic acid aptamer comprises one or more regions of double stranded character. Such double stranded regions may arise from internal self-complementarity or complementarity with a second or further aptamer molecule. In some embodiments, the double stranded region may be from 4-12, 4-10, 4-8 base pairs in length. In some embodiments, the double stranded region may be 5, 6, 7, 8, 9, 10, 11 or 12 base pairs. In some embodiments, the double stranded region may form a stem region. Such extended stem regions having double stranded character can serve to stabilize the nucleic acid aptamer. Extended stem regions of at least 6 base pairs may contribute to greater thermostability at higher temperatures and thereby, greater affinity for VWF and increased overall functionality as compared to shorter stem regions of 5 base pairs or less. Shorter stem regions may lead to unraveling of the stem-loop structure at higher temperatures and associated loss of affinity and overall functionality.

As used herein, the term "double stranded character" means that over any length of two nucleic acid molecules, their sequences form base pairings (standard or nonstandard) of more than 50 percent of the length. The secondary structure of aptamers described herein may be confirmed by computational models known in the art that predict nucleic acid folding based on free energy calculation, such as Mfold.

Those of ordinary skill in the art will appreciate that the composition of an oligonucleotide can influence complement activation. For example, the number of phosphorothioate substitutions is directly related to the relative degree of complement activation. Thus, in a preferred embodiment, the aptamers used in the pharmaceutical compositions and formulations and methods provided herein has a nucleotide sequence that includes no more than four, no more than three, no more than two or no more than one phosphorothioate backbone modification. In some embodiments, the nucleic acid aptamer contains no phosphorothioate modifications.

Aptamers of the present invention may be modified to increase thermostability. Thermostability of nucleic acid aptamers is an important factor that controls the structure, hybridization, and functions of aptamers. As non-limiting examples, modifications that may be used to enhancer aptamer thermostability include 2'-O-Methyl nucleosides, 2' Fluoro nucleosides, locked nucleic acids (LNAs), 2,6-Diaminopurine (2-Amino-dA), 5-Methyl dC, and Super T (5-hydroxybutynl-2'-deoxyuridine). The presence of 2'-O-Methyl nucleosides in DNA or RNA strands enhances thermostability of the duplexes and the effect is more prominent in RNA:RNA duplexes than in RNA:DNA duplexes. Modification of the 2'-deoxyribose with 2'-fluoro enhances the thermostability of the DNA-DNA duplexes by 1.3° C. per insertion. LNA bases have a modification to the ribose backbone that locks the base in the C3'-endo position, which favors RNA A-type helix duplex geometry. LNA modification significantly increases Tm and is also very nuclease resistant.

The thermostability of the nucleic acid aptamers is characterized by melting temperature ($T_m$) at which half of the DNA or RNA molecules are in a double stranded form, while the other half of the molecules are represented by single strand form. Tm may be determined by any method known in the art, such as UV absorbance measurement, circular dichroism spectroscopy, and thermal measurement. $T_m$ may be influenced by a number of factors such as aptamer concentration, pH, monovalent cation ($Na^+$, $K^+$) concentration, or divalent cation ($Mg^{2+}$) concentration. According to the present invention, aptamers have $T_m$ greater than 37° C. and maintain intact stem-loop structure in vivo.

Aptamers may be further modified to protect the aptamers from nuclease and other enzymatic activities. The aptamer sequence can be modified by any suitable methods known in the art. For example, phosphorothioate can be incorporated into the backbone, and 5'-modified pyrimidine can be included in 5' end of ssDNA for DNA aptamers. For RNA aptamers, modified nucleotides such as substitutions of the 2'—OH groups of the ribose backbone, e.g., with 2'-deoxy-NTP or 2'-fluoro-NTP, can be incorporated into the RNA molecule using T7 RNA polymerase mutants. 2'-O-Methyl nucleosides and LNAs can also contribute to the resistance to nucleases. The resistance of these modified aptamers to nuclease can be tested by incubating them with either purified nucleases or nuclease from mouse serum, and the integrity of aptamers can be analyzed by gel electrophoresis.

In some embodiments, such modified nucleic acid aptamers may be synthesized entirely of modified nucleotides, or with a subset of modified nucleotides. The modifications can be the same or different. All nucleotides may be modified, and all may contain the same modification. All nucleotides may be modified, but contain different modifications, e.g., all nucleotides containing the same base may have one type of modification, while nucleotides containing other bases may have different types of modification. For example, all purine nucleotides may have one type of modification (or are unmodified), while all pyrimidine nucleotides have another, different type of modification (or are unmodified). In this way, oligonucleotides, or libraries of oligonucleotides are generated using any combination of modifications as disclosed herein.

In some embodiments, the VWF aptamer is an aptamer or a salt thereof comprising the sequence, 5'GCCAGGGACC-UAAGACACAUGUCCCUGGC-3' (SEQ ID NO: 1).

In some embodiments, the VWF aptamer is an aptamer or a salt thereof comprising the structure: NH$_2$-mGmCmC-mAmGmGmGmAmCmCmUmAmAmGmAmCmAmC-mAmUmGmUmCmCmC mUmGmGmC-idT (SEQ ID NO: 2) (BT-100), where "NH" is a 5'-hexylamine linker phosphoramidite, "idT" is an inverted deoxythymidine, "mN" is a 2'-O-Methyl containing residue.

In some embodiments, the VWF aptamer is an aptamer or a salt thereof comprising the structure: PEG40K-NH-mGmCmCmAmGmGmGmAmCmCmUmAmAmGmAm-CmAmCmAmUmGmUmCmCmC mUmGmGmC-idT (SEQ ID NO: 3) (BT-200), where "NH" is a 5'-hexylamine linker phosphoramidite, "idT" is an inverted deoxythymidine, "mN" is a 2'-O-Methyl containing residue and "PEG" is a polyethylene glycol and PEG40K is a pegylation moiety having a molecular weight of approximately 40 KDa. It should be understood that the presence of a PEG moiety is optional but when present, may be of varied size.

In some embodiments, reversal agents are provided.

Figure 2:
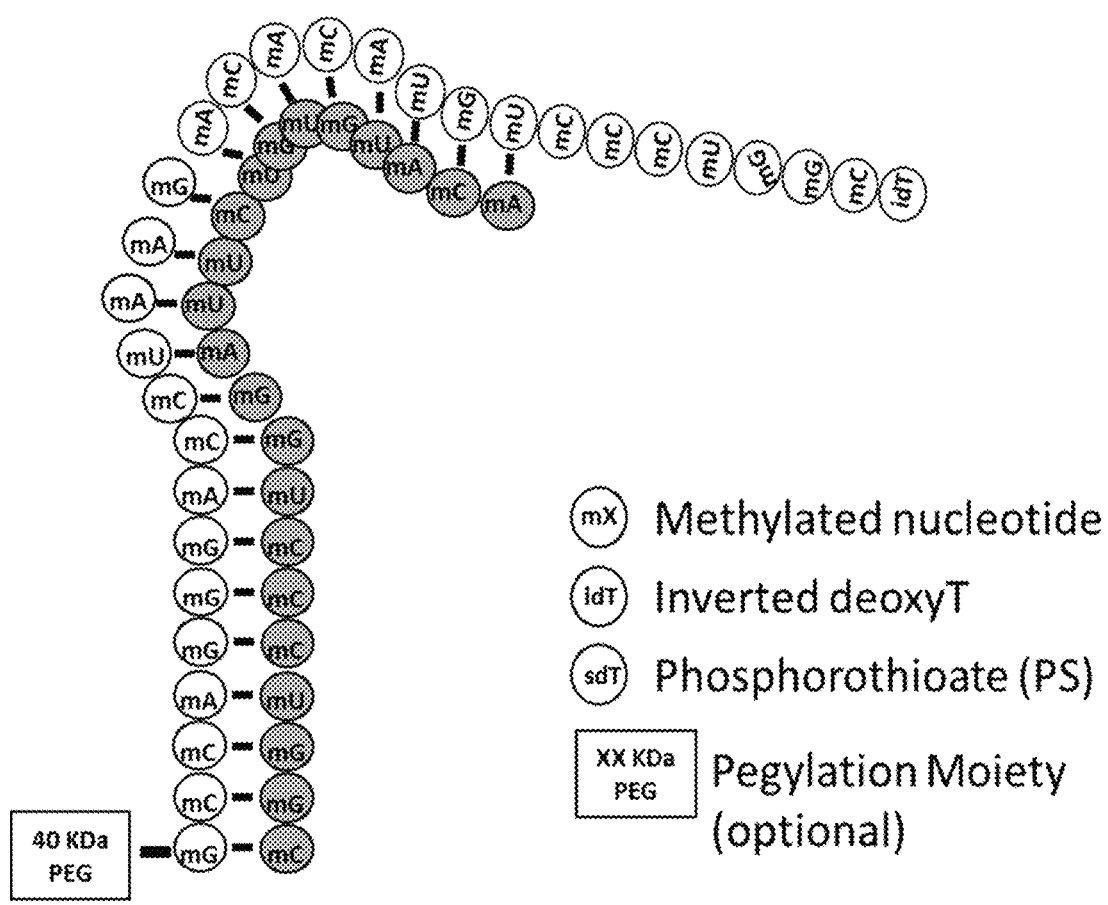
FIG. 2 is a diagram illustrating a BT-100 reversal agent.

According to the present invention, a "reversal agent" is one which alters, mitigates or reverses the effect of a VWF protective agent. In some embodiments, the reversal agents are nucleic acid based. In some embodiments, reversal agents are competitive binding molecules. In some embodiments, reversal agents bind VWF protective agents. In some embodiments, reversal agents hybridize with a portion of a VWF protective agent. In the case of nucleic acid based VWF protective agents such as aptamers, reversal agents may hybridize with all, a portion, a region of a protective aptamers. Reversal agents may comprise any or all of the modifications described herein. An example is illustrated in FIG. 2.

In some embodiments, the reversal agent comprises at least 15 contiguous nucleotides of the sequence 5'-ACAU-GUGUCUUAGGUCCCUGGC-3' (SEQ ID NO: 4). In some embodiments, the reversal agent comprises at least 12, 13, 14, 15, 16, 17, 18, 19, 20 or 21 contiguous nucleotides of SEQ ID NO: 4.

In some embodiments, the reversal agent comprises at least 12, 13, 14, 15, 16, 17, 18, 19, 20 or 21 contiguous nucleotides which are complementary to or bind to SEQ ID NO: 1.

In some embodiments, the least 12, 13, 14, 15, 16, 17, 18, 19, 20 or 21 contiguous nucleotides which are complementary to or bind to SEQ ID NO: 1 may be chemically modified. In some embodiments, at least one of the nucleotides contains at least one chemical modification. In some embodiments, each of the nucleotides contains at least one chemical modification. As a non-limiting example, the chemical modification may be a 2'-O-methyl modification to a nucleotide sugar. Additionally, least 12, 13, 14, 15, 16, 17, 18, 19, 20 or 21 contiguous nucleotides which are complementary to or bind to SEQ ID NO: 1 may further comprise a 3' terminal cap. In one embodiment, the 3' terminal cap may be an inverted deoxythymidine In some embodiments, the reversal agent is BT-201 having the sequence 5'mAmCmAmUmGmUmGmUmC-mUmUmAmGmGmUmCmCmUmGmGmC-idT 3' (SEQ ID NO: 5), where "idT" is an inverted deoxythymidine, "mN" is a 2'-O-Methyl containing residue.

In some embodiments, the VWF aptamer may comprise the sequence PEG40K-NH-mGmGmGmAmCmCmUmA-mAmGmAmCmAmCmAmUmGmUmCmCmC-idT (ARC15105) (SEQ ID NO: 6) or PEG20K-NH-mGmCmGmUdGdCdAmGmUmGmCmCmU-mUmCmGmGmCdCmGsdTmGdCdGdGdTm GmCdCmUdCdCmGmUdCmAmCmGmCidT (ARC1779) (SEQ ID NO:7), where "NH" is a 5'-hexylamine linker phosphoramidite, "idT" is an inverted deoxythymidine, "mN" is a 2'-O-Methyl containing residue, "dN" is a deoxynucleotide residue, "sdT" is a phosphorothioate deoxythymidine residue and "PEG" is a polyethylene glycol and PEG20K is a pegylation moiety having a molecular weight of approximately 20 KDa.

In some embodiments, the VWF aptamer, when used in methods of treating VAD disorders, may comprise the sequence PEG40K-NH-mGmGmGmAmCmCmUmA-mAmGmAmCmAmCmAmUmGmUmCmCmC-idT (ARC15105)(SEQ ID NO: 6) or PEG20K-NH-mGmCmGmUdGdCdAmGmUmGmCmCmU-mUmCmGmGmCdCmGsdTmGdCdGdGdTm GmCdCmUdCdCmGmUdCmAmCmGmCidT (ARC1779) (SEQ ID NO:7), where "NH" is a 5'-hexylamine linker phosphoramidite, "idT" is an inverted deoxythymidine, "mN" is a 2'-O-Methyl containing residue, "dN" is a deoxynucleotide residue, "sdT" is a phosphorothioate deoxythymidine residue and "PEG" is a polyethylene glycol and PEG20K is a pegylation moiety having a molecular weight of approximately 20 KDa.

In some embodiments, BT-200 preserves one or more characteristics and/or properties of BT-100. In other embodiments, BT-200 has one or more improved or altered characteristics and/or properties compared to BT-100. In one aspect, BT-200 has a longer plasma half-life than BT-100. In another aspect, BT-200 has a longer duration of action than BT-100.

In some embodiments, BT-200 preserves one or more characteristics and/or properties of ARC15105 or ARC1779. In some embodiments, BT-200 has one or more improved or altered characteristics and/or properties compared to ARC15105 or ARC1779. In one aspect, BT-200 has a longer plasma half-life than ARC15105 or ARC1779. In another aspect, BT-200 has a longer duration of action than ARC15105 or ARC1779. In another aspect, BT-200 has higher subcutaneous bioavailability. In another aspect, BT-200 has greater potency compared to ARC15105 or ARC1779 as a VWF protective agent.

Variations of VWF Protective Agents

The present invention contemplates several types of VWF protective agents which are nucleic acid based including variants and derivatives. These include substitutional, insertional, deletion and covalent variants and derivatives. As such, included within the scope of this invention are VWF protective agents containing substitutions, insertions and/or additions, deletions and covalently modifications.

The term "derivative" is used synonymously with the term "variant" and refers to a molecule that has been modified or changed in any way relative to a reference molecule or starting molecule.

The term "polynucleotide variant" refers to molecules which differ in their nucleic acid sequence from a reference sequence. The nucleic acid sequence variants may possess substitutions, deletions, and/or insertions at certain positions within the nucleic acid sequence, as compared to a reference sequence. Ordinarily, variants will possess at least about 50% identity (homology) to a reference sequence, and preferably, they will be at least about 80%, more preferably at least about 90% identical (homologous) to a reference sequence.

In some embodiments "variant mimics" are provided. As used herein, the term "variant mimic" is one which contains one or more nucleic acids which would mimic a reference sequence. The nucleic acid sequences of the VWF protective agents of the invention may comprise naturally occurring nucleic acids. Alternatively, the VWF protective agents may comprise both naturally and non-naturally occurring nucleic acids.

Ordinarily, variants will possess at least about 70% homology to a reference sequence, and preferably, they will be at least about 80%, more preferably at least about 90% homologous to a reference sequence.

"Homology" as it applies to nucleic acid sequences is defined as the percentage of residues in the candidate sequence that are identical with the residues in the sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

The term "analogs" is meant to include polynucleotide variants which differ by one or more nucleic acid alterations, respectively, e.g., substitutions, additions or deletions of residues that still maintain the properties of the parent polypeptide or polynucleotide.

"Substitutional variants" are those that have at least one nucleoside (or nucleotide) in a starting sequence removed and a different nucleoside (or nucleotide) inserted in its place at the same position. The substitutions may be single, where only one nucleoside (or nucleotide) in the molecule has been substituted, or they may be multiple, where two or more nucleosides (or nucleotides) have been substituted in the same molecule.

"Insertional variants" are those variants with one or more nucleosides (or nucleotides) inserted immediately adjacent to a nucleoside (or nucleotide) at a particular position in a starting sequence. "Immediately adjacent" to a nucleoside (or nucleotide) means directly to the 5' or 3' of the instant nucleoside or nucleotide of the polynucleotide.

"Deletional variants", are those with one or more nucleosides (or nucleotides) in the starting sequence removed. Ordinarily, deletional variants will have one or more nucleosides (or nucleotides) deleted in a particular region of the molecule.

Covalent modifications are traditionally introduced by reacting targeted nucleoside (or nucleotide) residues of the molecule with an organic derivatizing agent that is capable of reacting with selected atoms or residues. Such modifications are within the ordinary skill in the art and are performed without undue experimentation.

Covalent derivatives specifically include fusion molecules in which nucleic acids of the invention are covalently bonded to a non-proteinaceous polymer. The non-proteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol. The VWF protective agents may be linked to various non-proteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337; the contents of which are incorporated herein by reference in their entirety.

"Features" are defined as distinct nucleoside (or nucleotide) sequence-based components of a molecule. Features of the VWF protective agents of the present invention include surface manifestations, local conformational shape, folds, loops, half-loops, domains, half-domains, sites, termini or any combination thereof.

As used herein the term "surface manifestation" refers to a component of a polynucleotide appearing on an outermost surface.

As used herein the term "local conformational shape" means a structural manifestation which is located within a definable space of the polynucleotide.

As used herein the term "fold" means the resultant conformation of a nucleoside (or nucleotide) sequence upon energy minimization. A fold may occur at the secondary or tertiary level of the folding process.

As used herein the term "turn" means a bend which alters the direction of the backbone of a polynucleotide and may involve one, two, three or more nucleoside (or nucleotide) residues.

As used herein the term "loop" refers to a structural feature of a polynucleotide which reverses the direction of the backbone of the sequence and comprises four or more nucleoside (or nucleotide) residues.

As used herein the term "domain" refers to a motif of polynucleotide having one or more identifiable structural or functional characteristics or properties (e.g., binding capacity), serving as a site for molecular interactions.

As used herein the term "site" as it pertains to nucleoside (or nucleotide) based embodiments is used synonymous with "nucleic acid residue". A site represents a position within a polynucleotide that may be modified, manipulated, altered, derivatized or varied within the polynucleotide based molecules of the present invention.

As used herein the term "termini or terminus" refers to an extremity of a polynucleotide. Such extremity is not limited only to the first or final site of the polynucleotide but may include additional nucleosides (or nucleotides) in the terminal regions. The polynucleotide based molecules of the present invention may be characterized as having both a 5' terminus and a 3' terminus.

Once any of the features have been identified or defined as a component of a molecule of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full-length molecule would.

Modifications and manipulations can be accomplished by methods known in the art such as site directed mutagenesis. The resulting modified molecules may then be tested for activity using in vitro or in vivo assays such as those described herein or any other suitable screening assay known in the art.

Isotopic Variations

The VWF protective agents of the present invention may contain one or more atoms that are isotopes. As used herein, the term "isotope" refers to a chemical element that has one or more additional neutron. In one embodiment, compounds of the present invention may be deuterated. As used herein, the term "deuterated" refers to a substance that has had one or more hydrogen atoms replaced by deuterium isotopes. Deuterium isotopes are isotopes of hydrogen. The nucleus of hydrogen contains one proton while deuterium nuclei contain both a proton and a neutron. The VWF protective agents may be deuterated in order to change a physical property of the compound, such as stability, or to allow the compounds to be used in diagnostic and experimental applications.

Conjugates and Combinations

It is contemplated by the present invention that the VWF protective agents of the present invention may be complexed, conjugated or combined with one or more homologous or heterologous molecules. As used herein, "homologous molecule" means a molecule which is similar in at least one of structure or function relative to a starting molecule while a "heterologous molecule" is one that differs in at least one of structure or function relative to a starting molecule. Structural homologs are therefore molecules which are substantially structurally similar. They can be identical. Functional homologs are molecules which are substantially functionally similar. They can be identical.

VWF protective agents of the invention may comprise conjugates. Such conjugates of the invention may include a naturally occurring substance or ligand, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

VWF protective agents of the present invention can be designed to be conjugated to other polynucleotides, dyes, intercalating agents (e.g. acridines), cross-linkers (e.g. psoralene, mitomycin C), porphyrins (TPPC4, texaphyrin, Sapphyrin), reporter molecules, polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug.

The conjugates can also include targeting groups, e.g., a cell or tissue targeting agent or group, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers.

The targeting group can be any ligand that is capable of targeting a specific receptor. Examples include, without limitation, folate, GalNAc, galactose, mannose, mannose-6P, aptamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein.

In still other embodiments, the VWF protective agent is covalently conjugated to a cell penetrating polypeptide. The cell-penetrating peptide may also include a signal sequence. The conjugates of the invention can be designed to have increased stability; increased cell transfection; and/or altered the biodistribution (e.g., targeted to specific tissues or cell types).

VWF protective agents of the present invention may be designed to be conjugated to any number of conjugates. As a non-limiting example, the conjugates may be high molecular weight non-immunogenic compounds.

Conjugating moieties may be added to the VWF protective agents such that they allow labeling or flagging the VWF for clearance. Such tagging/flagging molecules include, but are not limited to ubiquitin, fluorescent molecules, human influenza hemaglutinin (HA), c-myc (a 10 amino acid segment of the human protooncogene myc with sequence EQKLISEEDL (SEQ ID NO: 10)), histidine (His), flag (a short peptide of sequence DYKDDDDK (SEQ ID NO: 11)), glutathione S-transferase (GST), V5 (a paramyxovirus of simian virus 5 epitope), biotin, avidin, streptavidin, horse radish peroxidase (HRP) and digoxigenin.

In some embodiments, VWF protective agents may be combined with other VWF protective agents, or other molecules in the treatment of a disease or condition.

The VWF protective agents may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body.

In some embodiments, the combination may include a therapeutic agent such as a cytotoxin, radioactive ion, chemotherapeutic, or other therapeutic agent. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020 incorporated herein by reference in its entirety), rachelmycin (CC-1065, see U.S. Pat. Nos. 5,475,092, 5,585,499, and 5,846,545, all of which are incorporated herein by reference in their entirety), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol, and maytansinoids).

In some embodiments, the combination may include a detectable agent, such as various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}F$, $^{67}Ga$, $^{81m}Kr$, $^{82}Rb$, $^{111}In$, $^{123}I$, $^{133}$Xe, $^{201}$Tl, $^{125}$I, $^{35}$S, $^{14}$C, $^{3}$H, or $^{99m}$Tc (e.g., as pertechnetate (technetate(VII), TcO$_4^-$)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), or ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2, 2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and-6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with N,N-diethylethanamine (1:1) (IR144); 5-chloro-2-[2-[3-[(5-chloro-3-ethyl-2(3H)-benzothiazol-ylidene)ethylidene]-2-(diphenylamino)-1-cyclopenten-1-yl] ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives (e.g., pyrene, pyrene butyrate, and succinimidyl 1-pyrene); butyrate quantum dots; Reactive Red 4 (CIBACRON™ Brilliant Red 3B-A); rhodamine and derivatives (e.g., 6-carboxy-X-rhodamine (ROX), 6-carboxyrhodamine (R6G), lissamine rhodamine B sulfonyl chloride rhodarnine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable agent may be a non-detectable pre-cursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical)). In vitro assays in which the enzyme labeled compositions can be used include, but are not limited to, enzyme linked immunosorbent assays (ELISAs), immunoprecipitation assays, immunofluorescence, enzyme immunoassays (EIA), radioimmunoassays (RIA), and Western blot analysis.

II. Targets of the Invention: VWF Monomers or Multimers

The present invention provides aptamers (themselves monomers or multimers) that bind to von Willebrand Factor (VWF) monomers or multimers. These aptamers are referred to herein as "VWF aptamers." As stated above, VWF aptamers may be nucleic acid based or amino acid based.

In some embodiments, the target of the VWF protective agents is the VWF protein or protein multimers. In some embodiments, VWF protective agents may be designed to bind or associate with proteins or other biomolecules which themselves associate with the VWF protein.

*Homo sapiens* Von Willebrand Factor mRNA is provided herein as SEQ ID NO: 8 (NM_000552; 8833 nt) and the protein as SEQ ID NO: 9 (NP_000543; 2813 amino acids).

The human VWF mRNA sequence is shown here: >gi|89191867|ref|NM_000552.3| *Homo sapiens* von Willebrand factor (VWF), mRNA: AGCTCACAGCTAT-
TGTGGTGGGAAAGGGAGGGTGGTTGGTGGATGT-
CACAGCTT
GGGCTTTATCTCCCCCAGCAGTGGGGACTC-
CACAGCCCCTGGGCTACATAACAGC
AAGACAGTCCGGAGCTGTAGCAGACCTGATT-
GAGCCTTTGCAGCAGCTGAGAGC
ATGGCCTAGGGTGGGCGGCACCAT-
TGTCCAGCAGCTGAGTTTCCCAGGGACCTTG
GAGATAGCCGCAGCCCTCATTTGCAGGGGAAGAT-
GATTCCTGCCAGATTTGCCGG
GGTGCTGCTTGCTCTGGCCCTCAT-
TTTGCCAGGGACCCTTTGTGCAGAAGGAACT
CGCGGCAGGTCATCCACGGCCC-
GATGCAGCCTTTTCGGAAGTGACTTCGTCAACA
CCTTTGATGGGAGCATGTACAGCTTTGCGGGA-
TACTGCAGTTACCTCCTGGCAGG
GGGCTGCCAGAAACGCTCCTTCTCGATTAT-
TGGGGACTTCCAGAATGGCAAGAG AGT-
GAGCCTCTCCGTGTATCTTGGGGAATTTTTGA-
CATCCATTTGTTTGTCAATG
GTACCGTGACACAGGGGGACCAAAGAGTCTC-
CATGCCCTATGCCTCCAAAGGGC
TGTATCTAGAAACTGAGGCTGGGTACTA-
CAAGCTGTCCGGTGAGGCCTATGGCTT
TGTGGCCAGGATCGATGGCAGCGGCAACTTT-
CAAGTCCTGCTGTCAGACAGATAC TTCAACAA-
GACCTGCGGGCTGTGTGGCAACTTTAA-
CATCTTTGCTGAAGATGACT
TTATGACCCAAGAAGGGACCTTGACCTCGGACCCT-
TATGACTTTGCCAACTCATG GGCTCTGAGCAGTG-
GAGAACAGTGGTGTGAACGGG-
CATCTCCTCCCAGCAGCTC
ATGCAACATCTCCTCTGGG-
GAAATGCAGAAGGGCCTGTGG-
GAGCAGTGCCAGCT TCT-
GAAGAGCACCTCGGTGTTTGCCCGCTGCCACCC
TCTGGTGGACCCCGAGCCT TTTGTGGCCCTGTGT-
GAGAAGACTTTGTGTGAGTGTGCTGGGGGGCTG-
GAGTGCG CCTGCCCTGCCCTCCTG-
GAGTACGCCCGGACCTGTGCCCAGGAGGGAAT
GGTGCT GTACGGCTGGACCGAC-
CACAGCGCGTGCAGCCCAGTGTGCCCTGCTG
GTATGGA
GTATAGGCAGTGTGTGTCCCCTTGCGCCAGGA
CCTGCCAGAGCCTGCACATCAAT
GAAATGTGTCAGGAGCGATGCGTG- GATGGCTGCAGCTGCCCTGAGGGACAGCTC CTGGATGAAGGCCTCTGCGTG-
GAGAGCACCGAGTGTCCCTGCGTGCATTCCGGA
AAGCGCTACCCTCCCGGCACCTCCCTCTCTCGA-
GACTGCAACACCTGCATTTGCC
GAAACAGCCAGTGGATCTGCAGCAAT-
GAAGAATGTCCAGGGGAGTGCCTTGTCA CAGGT-
CAATCACACTTCAAGAGCTTTGACAACAGATACTT-
CACCTTCAGTGGGAT
CTGCCAGTACCTGCTGGCCCGGGATTGCCAGGAC-
CACTCCTTCTCCATTGTCATT
GAGACTGTCCAGTGTGCT-
GATGACCGCGACGCTGTGTGCACCCGCTCCGT-
CACCG
TCCGGCTGCCTGGCCTGCACAACAGCCTTGT-
GAAACTGAAGCATGGGGCAGGAG TTGCCATG-
GATGGCCAGGACGTCCAGCTCCCCCTCCT-
GAAAGGTGACCTCCGCAT
CCAGCATACAGTGACGGCCTCCGTGCGCCTCAGC-
TACGGGGAGGACCTGCAGAT GGACTGG-
GATGGCCGCGGGAGGCTGCTGGT-
GAAGCTGTCCCCGTCTATGCCGG
GAAGACCTGCGCCTGTGTGGGAATTA-
CAATGGCAACCAGGGCGACGACTTCCT
TACCCCCTCTGGGCTGGCGGAGCCCCGGGTG-
GAGGACTTCGGGAACGCCTGGAA
GCTGCACGGGGACTGCCAGGACCTGCAGAAG
CAGCACAGCGATCCCTGCGCCCT CAACCCGCG-
CATGACCAGGTTCTCCGAG-
GAGGCGTGCGCGGTCCTGACGTCCCCC ACAT-
TCGAGGCCTGCCATCGTGCCGTCAGCCCGC
TGCCCTACCTGCGGAACTGCC
GCTACGACGTGTGCTCCTGCTCGGACGGCCGC-
GAGTGCCTGTGCGGCGCCCTGGC CAGC-
TATGCCGCGGCCTGCGCGGG-
GAGAGGCGTGCGCGTCGCGTGGCGCGAGCC
AGGCCGCTGTGAGCT-
GAACTGCCCGAAAGGCCAGGTGTACCTGCAGT
GCGGGAC
CCCCTGCAACCTGACCTGCCGCTCTCTCTCT-
TACCCGGATGAGGAATGCAATGAG GCCTGCCTG-
GAGGGCTGCTTCTGCCCCCCAGGGCTCTACATG-
GATGAGAGGGGG
GACTGCGTGCCCAAGGCCCAGTGCCCCTGTTAC-
TATGACGGTGAGATCTTCCAGC CAGAAGA-
CATCTTCTCAGACCATCACACCATGTGCTACTGT-
GAGGATGGCTTCAT
GCACTGTACCATGAGTGGAGTCCCCG-
GAAGCTTGCTGCCTGACGCTGTCCTCAGC
AGTCCCTGTCTCATCGCAGCAAAAGGAGCC-
TATCCTGTCGGCCCCCCATGGTCA
AGCTGGTGTGTCCCGCTGACAACCTGCGGGCT-
GAAGGGCTCGAGTGTACCAAAA CGTGCCAGAAC-
TATGACCTGGAGTGCATGAG-
CATGGGCTGTGTCTCTGGCTGCCT
CTGCCCCCGGGCATGGTCCGGCATGAGAACA-
GATGTGTGGCCCTGGAAAGGTG TCCCTGCTTC-
CATCAGGGCAAGGAGTATGCCCCTG-
GAGAAACAGTGAAGATTGG
CTGCAACACTTGTGTCTGTCGGACCGGAAGTG-
GAACTGCACAGACCATGTGTGT GATGC-
CACGTGCTCCACGATCGGCATGGCCCACTACCT-
CACCTTCGACGGGCTCA
AATACCTGTTCCCCGGG-
GAGTGCCAGTACGTTCTGGTGCAGGAT-
TACTGCGGCAG TAACCCTGGGACCTTTCG-
GATCCTAGTGGGGAATAAGGGATGCAGCCAC

CCCTCA GTGAAATGCAAGAAACGGGTCAC-
CATCCTGGTGGAGGGAGGAGAGATTGAGCTG
TTTGACGGGGAGGTGAATGTGAAGAGGCCCAT-
GAAGGATGAGACTCACTTTGAG GTGGTG-
GAGTCTGGCCGGTACATCAT-
TCTGCTGCTGGGCAAAGCCCTCTCCGTGG
TCTGGGACCGCCACCTGAGCATCTCCGTGGTCCT-
GAAGCAGACATACCAGGAGA
AAGTGTGTGGCCTGTGTGGGAATTTTGATGG-
CATCCAGAACAATGACCTCACCAG CAGCAACCTC-
CAAGTGGAGGAAGACCCTGTGGACTTTGG-
GAACTCCTGGAAAGT
GAGCTCGCAGTGTGCTGACACCAGAAAAGTG
CCTCTGGACTCATCCCCTGCCACC TGCCATAACAA-
CATCATGAAGCAGACGATGGTGGAT-
TCCTCCTGTAGAATCCTTA
CCAGTGACGTCTTCCAGGACTGCAACAAGCT
GGTGGACCCCGAGCCATATCTGG ATGTCTGCATT-
TACGACACCTGCTCCTGTGAGTCCAT-
TGGGGACTGCGCCTGCTTC TGCGACACCAT-
TGCTGCCTATGCCCACGTGTGTGCCCAGCATGG
CAAGGTGGTA CCTGGAGGACGGCCACAT-
TGTGCCCCAGAGCTGCGAGGAGAG-
GAATCCCGGG AGAAGGGTATGAGTGT-
GAGTGGCGCTATAACAGCTGTGCACCTGCCTGT
CAAG TCACGTGTCAGCACCCTGAGC-
CACTGGCCTGCCCTGTGCAGTGTGTGGAGGGCTG
CCATGCCCACTGCCCTCCAGGGAAAATCCTGGAT-
GAGCTTTTGCAGACCTGCGTT GACCCTGAA-
GACTGTCCAGTGTGT-
GAGGTGGCTGGCCGGCGTTTTGCCTCAGGAA
AGAAAGTCACCTTGAATCCCAGTGACCCT-
GAGCACTGCCAGATTTGCCACTGTGA TGTTGT-
CAACCTCACCTGTGAAGCCTGCCAGGAGCCGG-
GAGGCCTGGTGGTGCCT
CCCACAGATGCCCCGGTGAGCCCCAC-
CACTCTGTATGTGGAGGACATCTCGGAAC
CGCCGTTGCACGATTTCTACTGCAGCAGGC-
TACTGGACCTGGTCTTCCTGCTGGA
TGGCTCCTCCAGGCTGTCCGAGGCTGAGTTT-
GAAGTGCTGAAGGCCTTTGTGGTG GACATGATG-
GAGCGGCTGCG-
CATCTCCCAGAAGTGGGTCCGCGTGGCCGTGGTG
GAGTACCACGACGGCTCCCACGCCTACATCGGGCT-
CAAGGACCGGAAGCGACCG TCAGAGCTGCGGCG-
CATTGCCAGCCAGGT-
GAAGTATGCGGGCAGCCAGGTGGCC
TCCACCAGCGAGGTCTTGAAATACACACTGTTC-
CAAATCTTCAGCAAGATCGACC GCCCT-
GAAGCCTCCCGCATCACCCTGCTCCT-
GATGGCCAGCCAGGAGCCCCAACG
GATGTCCGGAACTTTGTCCGC-
TACGTCCAGGGCCTGAAGAAGAAGAAGGTCAT
TGTGATCCCGGTGGGCATTGGGCCCATGC-
CAACCTCAAGCAGATCCGCCTCATC
GAGAAGCAGGCCCCT-
GAGAACAAGGCCTTCGTGCTGAGCAGTGTGGAT-
GAGCTG GAGCAGCAAAGGGACGAGATCGTTAGC-
TACCTCTGTGACCTTGCCCCTGAAGCC
CCTCCTCCTACTCTGCCCCCGACATGGCACAAGT-
CACTGTGGGCCGGGGCTCT
TGGGGGTTTCGACCCTGGGGCCCAAGAGGAACTC-
CATGGTTCTGGATGTGGCGTT CGTCCTG-
GAAGGATCGGACAAAATTGGTGAAGCCGACTT
CAACAGGAGCAAGGA
GTTCATGGAGGAGGTGATTCAGCGGATG-
GATGTGGGCCAGGACAGCATCCACGT

CACGGTGCTGCAGTACTCCTACATGGTGACTGTGGAGTACCCCTTCAGCGAGGCA CAGTCCAAAGGGGACATCCTGCAGCGGGTGCGAGAGATCCGCTACCAGGGCGGC AACAGGACCAACACTGGGCTGGCCCTGCGGTACCTCTCTGACCACAGCTTCTTGG TCAGCCAGGGTGACCGGGAGCAGGCGCCCAACCTGGTCTACATGGTCACCGGAA ATCCTGCCTCTGATGAGATCAAGAGGCTGCCTGGAGACATCCAGGTGGTGCCCAT TGGAGTGGGCCCTAATGCCAACGTGCAGGAGCTGGAGAGGATTGGCTGGCCCAATGCCCCTATCCTCATCCAGGACTTTGACGCTCCCCGAGAGGCTCCTGACCTGGTGCTGCAGAGGTGCTGCTCCGGAGAGGGGCTGCAGATCCCCACCCTCTCCCTGCACCTGACTGCAGCCAGCCCTGGACGTGATCCTTCTCCTGGATGGCTCCTCCAGTTTCCCAGCTTCTTATTTTGATGAAATGAAGAGTTTCGCCAAGGCTTTCATTTCAA AAGCCAATATAGGGCCTCGTCTCACTCAGGTGTCAGTGCTGCAGTATGGAAGCATCACCACCATTGACGTGCCATGGAACGTGGTCCCGGAGAAAGCCCATTTGCTGAG CCTTGTGGACGTCATGCAGCGGGAGGGAGGCCCCAGCCAAATCGGGGATGCCTT
GGGCTTTGCTGTGCGATACTTGACTTCAGAAATGCATGGTGCCAGGCCGGGAGCC
TCAAAGGCGGTGGTCATCCTGGTCACGGACGTCTCTGTGGATTCAGTGGATGCAGCAGCTGATGCCGCCAGGTCCAACAGAGTGACAGTGTTCCCTATTGGAATTGGAGATCGCTACGATGCAGCCCAGCTACGATCTTGGCAGGCCCAGCAGGCGACTCCAACGTGGTGAAGCTCCAGCGAATCGAAGACCTCCCTACCATGGTCACCTTGGGCA ATTCCTTCCTCACAAACTGTGCTCTGGATTTGTTAGGATTTGCATGGATGAGGATGGGAAT
GAGAAGAGGCCCGGGGACGTCTGGACCTTGCCAGACCAGTGCCACACC GTGACTTGCCAGCCAGATGGCCAGAACCCTTGCTGAAGAGTCATCGGGTCAACTGTG ACCGGGGCTGAGGCCTTCGTGCCCTAACAGCCAGTCCCCTGTTAAAGTGGAAG
AGACCTGTGGCTGCCGCTGGACCTGCCCCT GCGTGTGCACAGGCAGCTCCACTCG GCACATCGTGACCTTTGATGGGCAGAATTTCAAGCTGACTGGCAGCTGTTCTTAT GTCCTATTTCAAAACAAGGAGCAGGACCTGGAGGTGATTCTCCATAATGGTGCCT GCAGCCCTGGAGCAAGGCAGGGCTGCATGAAATCCATCGAGGTGAAGCACAGTG
CCCTCTCCGTCGAGCTGCACAGTGACATGGAGGTGACGGTGAATGGGAGACTGG TCTCTGTTCCTTACGTGGGTGGGAACATGGAAGTCAACGTTTATGGTGCCATCAT GCATGAGGTCAGATTCAATCACCTTGGTCACATCTTCACATTCACTCCACAAAAC
AATGAGTTCCAACTGCAGCTCAGCCCCAAGACTTTTGCTTCAAAGACGTATGGTC TGTGTGGGATCTGTGATGAACGGAGCCAATGACTTCATGCTGAGGGATGCA
CAGTCACCACAGACTGGAAAACACTTGTTCAGGAATGGACTGTGCAGCGGCCAG GGCAGACGTGCCAGCCCATCCTGGAGGAGCAGTGTCTTGTCCCCGACAGCTCCCA

CTGCCAGGTCCTCCTCTTACCACTGTTTGCTGAATGCCACAAGGTCCTGGCTCCA GCCACATTCTATGCCATCTGCCAGCAGGACAGTTGCCACCAGGAGCAAGTGTGTG
AGGTGATCGCCTCTTATGCCCACCTCTGTCGGACCAACGGGGTCTGCGTTGACTG GAGGACACCTGATTTCTGTGCTATGTCATGCCCACCATCTCTGGTCTACAACCAC
TGTGAGCATGGCTGTCCCCGGCACTGTGATGGCAACGTGAGCTCCTGTGGGGACC ATCCCTCCGAAGGCTGTTTCTGCCCTCCAGATAAAGTCATGTTGGAAGGCAGCTG TGTCCCTGAAGAGGCCTGCACTCAGTGCATTGGTGAGGATGGAGTCCAGCACCA
GTTCCTGGAAGCCTGGGTCCCGGACCACCAGCCCTGTCAGATCTGCACATGCCTC AGCGGGCGGAAGGTCAACTGCACAACGCAGCCCTGCCCCACGGCCAAAGCTCCC ACGTGTGGCCTGTGTGAAGTAGCCCGCCTCCGCCAGAATGCAGACCAGTGCTGCC CCGAGTATGAGTGTGTGTGACCCAGTGAGCTGTGACCTGCCCCAGTGCCTCA CTGTGAACGTGGCCTCCAGCCCACACTGACCAACCCTGGCGAGTGCAGACCCAA CTTCACCTGCGCCTGCAGGAAGGAGGAGTGCAAAAGAGTGTCCCCACCCTCCTG CCCCCCGCACCGTTTGCCCACCCTTCGGAAGACCCAGTGCTGTGATGAGTATGAG
TGTGCCTGCAACTGTGTCAACTCCACAGTGAGCTGTCCCCTTGGGTACTTGGCCT CAACTGCCACCAATGACTGTGGCTGTACCACAACCACCTGCCTTCCCGACAAGGT
GTGTGTCCACCGAAGCACCATCTACCCTGTGGGCCAGTTCTGGGAGGAGGGCTGC GATGTGTGCACCTGCACCGACATGGAGGATGCCGTGATGGGCCTCCGCGTGGCC
CAGTGCTCCCAGAAGCCCTGTGAGGACAGCTGTCGGTCGGGCTTCACTTACGTTC TGCATGAAGGCGAGTGCTGTGGAAGGTGCCTGCCATCTGCCTGTGAGGTGGTGA CTGGCTCACCGCGGGGGGACTCCCAGTCTTCCTGGAAGAGTGTCGGCTCCCAGTG GGCCTCCCCGGAGAACCCTGCCTCATCAATGAGTGTGTCCGAGTGAAGGAGGA GGTCTTTATACAACAAAGGAACGTCTCCTGCCCCCAGCTGGAGGTCCCTGTCTGC
CCCTCGGGCTTTCAGCTGAGCTGTAAGACCTCAGCGTGCTGCCCAAGCTGTCGCT GTGAGCGCATGGAGGCCTGCATGCTCAATGGCACTGTCATTGGGCCCGGGAAGA CTGTGATGATCGATGTGTGCACGACCTGCCGCTGCATGGTGCAGGTGGGGTCAT CTCTGGATTCAAGCTGGAGTGCAGGAAGACCACCTGCAACCCCTGCCCCTGGGT TACAAGGAAGAAAATAACACAGGT
GAATGTTGTGGGAGATGTTTGCCTACGGCT TGCACCATTCAGCTAAGAGGAGGACAGATCATGACACTGAAGCGTGATGAGACG
CTCCAGGATGGCTGTGATACTCACTTCTGCAAGGTCAATGAGAGAGGAGAGTAC TTCTGGGAGAAGAGGGTCACAGGCTGCCCACCCTTTGATGAACACAAGTGTCTG
GCTGAGGGAGGTAAAATTATGAAAATTCCAGGCACCTGCTGTGACACATGTGAG GAGCCTGAGTGCAACGACATCACTGCCAGGCTGCAGTATGTCAAGGTGGGAAGC
TGTAAGTCTGAAGTAGAGGTGGATATCCACTACTGCCAGGGCAAATGTGCCAGC AAAGC

CATGTACTCCATTGACATCAACGATGTGCAGGACCAGTGCTCCTGCTGCTCTCCGACACGGACGGAGCCCATGCAGGTGGCCCTGCACTGCACCAATGGCTCTGT TGTGTACCATGAGGTTCTCAATGCCATGGAGTGCAAATGCTCCCCCAGG AAGTGC AGCAAGTGAGGCTGCTGCAGCTGCATGGGTGCCTGCTGCTGCCTGCCTTGGCCTG ATGGCCAGGCCAGAGTGCTGCCAGTCCTCTGCATGTTCTGCTCTTGTGCCCTTCTG AGCCCACAATAAAGGCTGAGCTCTTATCTTGCAAAAGGC (SEQ ID NO: 8). It is noted that in this mRNA, Uridine is represented by Thymidine.

The protein sequence is shown here: >gi|89191868|ref|NP_000543.2| von Willebrand factor preproprotein [*Homo sapiens*].

```
                                        (SEQ ID NO: 9)
MIPARFAGVLLALALILPGTLCAEGTRGRSSTARCSLFGSDFVNTFDGSM

YSFAGYCSYLLAGGCQKRSFSIIGDFQNGKRVSLSVYLGEFFDIHLFVNG

TVTQGDQRVSMPYASKGLYLETEAGYYKLSGEAYGFVARIDGSGNFQVLL

SDRYFNKTCGLCGNFNIFAEDDFMTQEGTLTSDPYDFANSWALSSGEQWC

ERASPPSSSCNISSGEMQKGLWEQCQLLKSTSVFARCHPLVDPEPFVALC

EKTLCECAGGLECACPALLEYARTCAQEGMVLYGWTDHSACSPVCPAGME

YRQCVSPCARTCQSLHINEMCQERCVDGCSCPEGQLLDEGLCVESTECPC

VHSGKRYPPGTSLSRDCNTCICRNSQWICSNEECPGECLVTGQSHFKSFD

NRYFTFSGICQYLLARDCQDHSFSIVIETVQCADDRDAVCTRSVTVRLPG

LHNSLVKLKHGAGVAMDGQDVQLPLLKGDLRIQHTVTASVRLSYGEDLQM

DWDGRGRLLVKLSPVYAGKTCGLCGNYNGNQGDDFLTPSGLAEPRVEDFG

NAWKLHGDCQDLQKQHSDPCALNPRMTRFSEEACAVLTSPTFEACHRAVS

PLPYLRNCRYDVCSCSDGRECLCGALASYAAACAGRGVRVAWREPGRCEL

NCPKGQVYLQCGTPCNLTCRSLSYPDEECNEACLEGCFCPPGLYMDERGD

CVPKAQCPCYYDGEIFQPEDIFSDHHTMCYCEDGFMHCTMSGVPGSLLPD

AVLSSPLSHRSKRSLSCRPPMVKLVCPADNLRAEGLECTKTCQNYDLECM

SMGCVSGCLCPPGMVRHENRCVALERCPCFHQGKEYAPGETVKIGCNTCV

CRDRKWNCTDHVCDATCSTIGMAHYLTFDGLKYLFPGECQYVLVQDYCGS

NPGTFRILVGNKGCSHPSVKCKKRVTILVEGGEIELFDGEVNVKRPMKDE

THFEVVESGRYIILLLGKALSVVWDRHLSISVVLKQTYQEKVCGLCGNFD

GIQNNDLTSSNLQVEEDPVDFGNSWKVSSQCADTRKVPLDSSPATCHNNI

MKQTMVDSSCRILTSDVFQDCNKLVDPEPYLDVCIYDTCSCESIGDCACF

CDTIAAYAHVCAQHGKVVTWRTATLCPQSCEERNLRENGYECEWRYNSCA

PACQVTCQHPEPLACPVQCVEGCHAHCPPGKILDELLQTCVDPEDCPVCE

VAGRRFASGKKVTLNPSDPEHCQICHCDVVNLTCEACQEPGGLVVPPTDA

PVSPTTLYVEDISEPPLHDFYCSRLLDLVFLLDGSSRLSEAEFEVLKAFV

VDMMERLRISQKWVRVAVVEYHDGSHAYIGLKDRKRPSELRRIASQVKYA

GSQVASTSEVLKYTLFQIFSKIDRPEASRITLLLMASQEPQRMSRNFVRY

VQGLKKKKVIVIPVGIGPHANLKQIRLIEKQAPENKAFVLSSVDELEQQR

DEIVSYLCDLAPEAPPPTLPPDMAQVTVGPGLLGVSTLGPKRNSMVLDVA

FVLEGSDKIGEADFNRSKEFMEEVIQRMDVGQDSIHVTVLQYSYMVTVEY

PFSEAQSKGDILQRVREIRYQGGNRTNTGLALRYLSDHSFLVSQGDREQA

PNLVYMVTGNPASDEIKRLPGDIQVVPIGVGPNANVQELERIGWPNAPIL

IQDFETLPREAPDLVLQRCCSGEGLQIPTLSPAPDCSQPLDVILLLDGSS

SFPASYFDEMKSFAKAFISKANIGPRLTQVSVLQYGSITTIDVPWNVVPE

KAHLLSLVDVMQREGGPSQIGDALGFAVRYLTSEMHGARPGASKAVVILV

TDVSVDSVDAAADAARSNRVTVFPIGIGDRYDAAQLRILAGPAGDSNVVK

LQRIEDLPTMVTLGNSFLHKLCSGFVRICMDEDGNEKRPGDVWTLPDQCH

TVTCQPDGQTLLKSHRVNCDRGLRPSCPNSQSPVKVEETCGCRWTCPCVC

TGSSTRHIVTFDGQNFKLTGSCSYVLFQNKEQDLEVILHNGACSPGARQG

CMKSIEVKHSALSVELHSDMEVTVNGRLVSVPYVGGNMEVNVYGAIMHEV

RFNHLGHIFTFTPQNNEFQLQLSPKTFASKTYGLCGICDENGANDFMLRD

GTVTTDWKTLVQEWTVQRPGQTCQPILEEQCLVPDSSHCQVLLLPLFAEC

HKVLAPATFYAICQQDSCHQEQVCEVIASYAHLCRTNGVCVDWRTPDFCA

MSCPPSLVYNHCEHGCPRHCDGNVSSCGDHPSEGCFCPPDKVMLEGSCVP

EEACTQCIGEDGVQHQFLEAWVPDHQPCQICTCLSGRKVNCTTQPCPTAK

APTCGLCEVARLRQNADQCCPEYECVCDPVSCDLPPVPHCERGLQPTLTN

PGECRPNFTCACRKEECKRVSPPSCPPHRLPTLRKTQCCDEYECACNCVN

STVSCPLGYLASTATNDCGCTTTTCLPDKVCVHRSTIYPVGQFWEEGCDV

CTCTDMEDAVMGLRVAQCSQKPCEDSCRSGFTYVLHEGECCGRCLPSACE

VVTGSPRGDSQSSWKSVGSQWASPENPCLINECVRVKEEVFIQQRNVSCP

QLEVPVCPSGFQLSCKTSACCPSCRCERMEACMLNGTVIGPGKTVMIDVC

TTCRCMVQVGVISGFKLECRKTTCNPCPLGYKEENNTGECCGRCLPTACT

IQLRGGQIMTLKRDETLQDGCDTHFCKVNERGEYFWEKRVTGCPPFDEHK

CLAEGGKIMKIPGTCCDTCEEPECNDITARLQYVKVGSCKSEVEVDIHYC

QGKCASKAMYSIDINDVQDQCSCCSPTRTEPMQVALHCTNGSVVYHEVLN

AMECKCSPRKCSK.
```

It should be understood that all or any fragment (of from 5 amino acids to the full length) of the VWF protein may be used to produce VWF protective agents as described herein. Mutated versions or variants of SEQ ID NO: 9 may also be used to design VWF protective agents.

According to the present invention, and while not wishing to be bound by theory, the VWF protective agents may completely or partially inhibit VWF monomer or multimers degradation by partially or completely blocking the ability of VWF to bind to platelets or erythrocytes. The VWF aptamers are considered to completely inhibit VWF degradation when the level of protection of a monomer or multimers of at least 2 monomers is at least 95%, e.g., by 96%, 97%, 98%, 99% or 100% as compared to the level of intact monomer or multimers in the absence of the VWF protective agent.

The VWF aptamers are considered to partially inhibit VWF degradation when the level of protection of a monomer or multimers of at least 2 monomers is at least 10%, 20%, 25%, 30%, 40%, 50%, 60%, 75%, 80%, 85% or 90% as compared to the level of intact monomer or multimers in the absence of the VWF protective agent.

In other embodiments in which at least one vessel of a subject is partially (at least 50%) occluded or fully occluded by occlusive thrombi, the VWF protective agents may completely or partially disaggregate occlusive thrombi by partially or completely blocking the ability of VWF to bind to platelets. The VWF aptamers are considered to completely disaggregate occlusive thrombi when the occlusive thrombi are at least 95% disaggregated, e.g., 95%, 96%, 97%, 98%, 99% or 100% disaggregated, as compared to the level of occlusive thrombi in the absence of the VWF protective agent.

The VWF aptamers are considered to partially disaggregate occlusive thrombi when the occlusive thrombi are at least 10%, 20%, 25%, 30%, 40%, 50%, 60%, 75%, 80%, 85% or 90% disaggregated as compared to the level of occlusive thrombi in the absence of the VWF protective agent.

A VWF protective agent which is a nucleic acid aptamer may comprise a dissociation constant for human von Willebrand Factor domain A1 or a variant thereof, of less than 100 uM, less than 1 uM, less than 500 nM, less than 100 nM, preferably 50 nM or less, preferably 10 nM or less, preferably 5 nM or less, preferably 1 nM or less, and more preferably 500 pM or less.

III. VWF Protective Agents: Therapeutics

Aptamers have a number of desirable characteristics for use as therapeutics including high specificity and affinity to molecular targets, biological efficacy, and excellent pharmacokinetic properties. In addition, they offer specific competitive advantages over other biologics, for example:

Speed and Control.

Aptamers may be produced by an entirely in vitro process. In vitro selection allows the specificity and affinity of the aptamer to be tightly controlled and allows the generation of leads against both toxic and non-immunogenic targets. Aptamers may also be produced synthetically, whether by chemical synthesis such as solid phase synthesis or enzymatic synthesis using polymerase enzymes such as T7 RNA polymerase.

Toxicity and Immunogenicity.

Aptamers as a class have demonstrated little or no toxicity or immunogenicity. Such immunogenicity may be further controlled by incorporating chemical modifications which mute or ameliorate such immune responses. Such modifications are taught in International Publication PCT/US2012/058519, the contents of which are incorporated herein by reference in their entirety.

Administration.

Whereas all currently approved antibody therapeutics are administered by intravenous infusion (typically over 2-4 hours), aptamers can be administered by subcutaneous injection or by other routes. Aptamer bioavailability via subcutaneous administration has been shown to be >80% in monkey studies. In some embodiments, subcutaneous administration of VWF protective agents to a subject may yield a bioavailability of at least about 50%, about 70%, about 80%, about 85%, about 90%, about 95%, or about 98%, or about 99% relative to that of an intravenous administration.

Scalability and Cost.

Aptamers are chemically or enzymatically synthesized and consequently can be readily scaled as needed to meet production demand.

Stability.

Aptamers may be adapted to regain activity following exposure to heat, denaturants, etc. and can be stored for extended periods (>1 year).

Combination Therapy.

One embodiment of the invention comprises a VWF protective agent formulation of the invention used in combination with one or more other treatments for coagulation, bleeding or VAD-associated disorders. In another embodiment, a VWF protective agent formulation can be used in combination with one or more other treatments for acute coronary syndrome or acute occlusion thrombosis, including for example, but not limited to, aspirin, thrombolytics (i.e., tissue plasminogen activator, alteplase), nitroglycerin, beta blockers, angiotensin-converting enzyme (ACE) inhibitors, angiotensin receptor blockers (ARBs), $Ca^{2+}$ channel blockers, cholesterol-lowering drugs, (i.e., tissue plasminogen activator (tPA), alteplase), and clot preventing drugs (i.e., clopidogrel and prasugrel). In another embodiment, a VWF protective agent formulation can be used in combination with one or more other treatments used to disaggregate platelet aggregates, such as, for example, thrombolytic treatments targeting fibrin, and treatments that seeks to disrupt the platelet —-fibrin interaction, i.e., platelet GpIIb/IIIa inhibitors, such as abciximab, eptifibatide, tirofiban). In another embodiment, a VWF protective agent formulation can be used in combination with one or more other treatments used to treat ischemic stroke, such as, for example, anti-coagulants, thrombolytics (tPA, alteplase), anti-platelet therapy (e.g., aspirin, dabigatran, clopidogrel, dipyridamole), and warfarin. The VWF protective agent formulation of the invention may contain, for example, more than one aptamer. In some embodiments, a VWF protective agent formulation of the invention, containing one or more aptamers, is administered in combination with another useful formulation or drug. In another embodiment, the aptamer formulations are used in combination with non-drug therapies or treatments, such as surgical procedures. In general, the currently available dosage forms of the known therapeutic agents and the uses of non-drug therapies for use in such combinations will be suitable.

"Combination therapy" (or "co-therapy") includes the administration of a VWF protective agent formulation of the invention and at least a second agent or treatment as part of a specific treatment regimen intended to provide the beneficial effect from the co-action of these therapeutic agents or treatments. The beneficial effect of the combination includes, but is not limited to, pharmacokinetic or pharmacodynamic co-action resulting from the combination of therapeutic agent or treatments. Administration of these therapeutic agents or treatments in combination typically is carried out over a defined time period (usually minutes, hours, days or weeks depending upon the combination selected).

Combination therapy may, but generally is not, intended to encompass the administration of two or more of these therapeutic agents or treatments as part of separate monotherapy regimens that incidentally and arbitrarily results in the combinations of the present invention. Combination therapy is intended to embrace administration of these therapeutic agents or treatments in a sequential manner, that is, wherein each therapeutic agent or treatment is administered at a different time, as well as administration of these therapeutic agents or treatments, or at least two of the therapeutic agents or treatments, in a substantially simultaneous manner. Substantially simultaneous administration can be accomplished, for example, by administering to the subject a single injection having a fixed ratio of each therapeutic agent or in multiple, single injections for each of the therapeutic agents.

Sequential or substantially simultaneous administration of each therapeutic agent or treatment can be affected by any appropriate route including, but not limited to, topical routes, oral routes, intravenous routes, subcutaneous, intramuscular routes, and direct absorption through mucous membrane tissues. The therapeutic agents or treatments can be administered by the same route or by different routes. For example, a first therapeutic agent or treatment of the combination selected may be administered by injection while the other therapeutic agents or treatments of the combination may be administered subcutaneously. Alternatively, for example, all therapeutic agents or treatments may be administered subcutaneously or all therapeutic agents or treatments may be administered by injection. The sequence in which the therapeutic agents or treatments are administered is not critical unless noted otherwise.

Combination therapy also can embrace the administration of the therapeutic agent or treatments as described above in further combination with other biologically active ingredients. Where the combination therapy comprises a non-drug treatment, the non-drug treatment may be conducted at any suitable time so long as a beneficial effect from the co-action of the combination of the therapeutic agent and non-drug treatment is achieved. For example, in appropriate cases, the beneficial effect is still achieved when the non-drug treatment is temporally removed from the administration of the therapeutic agent, perhaps by days or even weeks.

Pharmacokinetic or Pharmacodynamic Properties.

Aptamers may be modified to improve pharmacokinetic or pharmacodynamic properties such as half-life and/or duration of action. As used herein, the term "half-life" or "plasma half-life" refers to the amount of time by which half of the administered amount of aptamer is cleared from the blood stream. "Duration of action" refers to the length of time that an aptamer is effective. The duration of action of aptamers may depend on several parameters such as plasma half-life, the administered dose, the pharmaceutical preparation, and the influence of disease on drug elimination (Carruthers S G. Duration of drug action. Am Fam Physician. 1980 February; 21(2): 119-26, which is incorporated herein by reference in its entirety). Modification of the aptamers, such as altering the stem region, or attaching the aptamers to polymers (e.g., PEG), may alter the half-life and/or duration of action.

In some embodiments, aptamers of the present invention may have a plasma half-life of from about 20 hours to about 40 hours, from about 30 hours to about 50 hours, from about 40 hours to about 60 hours, from about 50 hours to about 70 hours, from about 55 hours to about 75 hours, from about 60 hours to about 80 hours, from about 70 hours to about 85 hours, from about 75 hours to about 90 hours, from about 85 to about 100 hours, or at least 100 hours after administered to a subject.

In some embodiments, aptamers of the present invention may have a duration of action of at least 8 hours, at least 16 hours, at least 24 hours, at least 36 hours, at least 48 hours, at least 72 hours, from about 72 hours to about 96 hours, from about 90 hours to 120 hours, from about 110 hours to about 135 hours, from about 120 hours to 150 hours, from about 135 hours to 168 hours, from about 150 hours to 180 hours, from about 180 hours to about 210 hours, from about 210 hours to about 240 hours, from about 240 hours to 300 hours, from about 300 hours to 360 hours, or at least 360 hours.

Anticoagulation and clotting. In some embodiments, the aptamers of the present invention do not function as anticoagulants and/or alter clotting function. As used herein, the term "anticoagulant" refers to a chemical substance that prevent or reduce coagulation of blood, prolonging the clotting time. Coagulation of blood may be assayed via the techniques and methods described herein and those known in the art, such as activated partial thromboplastin time (aPTT) assays, prothrombin time (PT) test, thrombin time test, fibrinogen test, anti-factor Xa assays, rotational thrombelastometry, and thrombin generation assays (e.g., calibrated automated thrombogram).

In some embodiments, aptamers of the present invention do not prolong clotting time. In some embodiments, aptamers of the present invention do not prolong activated partial thromboplastin time. In some embodiments, aptamers of the present invention do not prolong prothrombin time. In some embodiments, aptamers of the present invention do not prolong thrombin time. In some embodiments, aptamers of the present invention do not alter fibrinogen concentration. In some embodiments, aptamers of the present invention do not alter thrombin generation.

IV. Formulations, Dosing and Administration

Pharmaceutical Compositions and Formulations

The pharmaceutical compositions of the present invention comprise at least one VWF protective agent as the active ingredient. In some embodiments, the compositions are suitable for internal use and include an effective amount of a pharmacologically active compound of the invention, alone or in combination, with one or more pharmaceutically acceptable carriers. The compounds are especially useful in that they have very low, if any toxicity.

Formulations which may be suitable for the pharmaceutical compositions of the present invention, particularly the nucleic acid based compositions, are taught in International Publication WO2013/090648 (Application PCT/US2012/069610), the contents of which are incorporated herein by reference in their entirety.

The formulations may comprise any amount of aptamers of the present invention or a pharmaceutically acceptable salt thereof. As used herein, the term "pharmaceutically acceptable salt" refers to salt forms of the active compound that are prepared with counter ions that are non-toxic under the conditions of use and are compatible with a stable formulation. Examples of pharmaceutically acceptable salts of aptamers include sodium salts, hydrochlorides, sulfates, phosphates, acetates, fumarates, maleates and tartrates. The formulations may comprise any aptamer or a combination of aptamers that bind to the full length of the polypeptide or a variant or a fragment thereof. The polypeptide may be from any species, but is preferably from human.

The formulations also comprise a pharmaceutically acceptable solvent. As used herein, the term "pharmaceutically acceptable solvent" refers to being compatible with the other ingredients of the formulation and not deleterious to the recipient thereof. Pharmaceutically acceptable solvents are well known in the art. Examples of pharmaceutically acceptable solvents can be found, for example, in Goodman and Gillmans, *The Pharmacological Basis of Therapeutics*, latest edition, the contents of which are incorporated herein by reference in their entirety. Preferably, the pharmaceutically acceptable solvent is selected from the group consisting of 0.9% saline (also known as physiological saline or sterile isotonic saline solution) or phosphate buffered saline. Most preferably, the pharmaceutically acceptable solvent is 0.9% saline.

The formulations may comprise any amount of pharmaceutically acceptable solvent.

Various embodiments of the formulations may, optionally, include one or more of the following: buffer, pH adjuster, tonicity agent, cosolvent or pharmaceutically acceptable carrier.

In some embodiments, the formulations may further comprise a buffer. A buffer is any substance that, when added to a solution, is capable of neutralizing both acids and bases without appreciably changing acidity or alkalinity of the solution. Examples of buffers include, but are not limited to, pharmaceutically acceptable salts and acids of acetate, glutamate, citrate, tartrate, benzoate, lactate, histidine or other amino acids, gluconate, phosphate, malate, succinate, formate, propionate and carbonate.

In some embodiments, the formulations may further comprise a pH adjuster. A pH adjuster is used to adjust the pH of the formulation. Suitable pH adjusters typically include at least an acid or a salt thereof and/or a base or a salt thereof. Acids and bases can be added on an as needed basis in order to achieve a desired pH. For example, if the pH is greater than the desired pH, an acid may be used to lower the pH to the desired pH. Examples of acids include, but are not limited to, hydrochloric acid, phosphoric acid, citric acid, ascorbic acid, acetic acid, sulphuric acid, carbonic acid and nitric acid. By way of another example, if the pH is less than the desired pH, a base can be used to adjust the pH to the desired pH. Examples of bases include, but are not limited to, sodium hydroxide, potassium hydroxide, calcium hydroxide, sodium carbonate, sodium citrate, sodium acetate and magnesium hydroxide.

In some embodiments, the formulations may further comprise a tonicity agent. Tonicity agents are used to adjust the osmolality of the formulations in order to bring them closer to the osmotic pressure of body fluids, such as blood or plasma. Examples of tonicity agents include, but are not limited to, anhydrous or hydrous forms of sodium chloride, dextrose, sucrose, xylitol, fructose, glycerol, sorbitol, mannitol, potassium chloride, mannose, calcium chloride, magnesium chloride and other inorganic salts.

In some embodiments, the formulations may further comprise a cosolvent. A cosolvent is a solvent that is added to the aqueous formulation in a weight amount that is less than that of water and assists in the solubilization of the aptamer. Examples of cosolvents include, but are not limited to, glycols, ethanol and polyhydric alcohols.

In some embodiments, the formulations may further comprise a pharmaceutically acceptable carrier. As used herein, the term "pharmaceutically acceptable carrier" refers to being compatible with the other ingredients of the formulation and not deleterious to the recipient thereof. Pharmaceutically acceptable carriers are well known in the art. Examples of pharmaceutically acceptable carriers can be found, for example, in Goodman and Gillmans, *The Pharmacological Basis of Therapeutics*, latest edition.

The formulations described herein are stable. The term "stable", as used herein, means remaining in a state or condition that is suitable for administration to a patient.

The formulations are, preferably, substantially pure. As used herein, "substantially pure" means that the active ingredient (aptamer) is the predominant species present (i.e., on a molar basis it is more abundant than any other individual species in the composition), and preferably a substantially purified fraction is a composition wherein the active ingredient comprises at least about 50 percent (on a molar basis) of all macromolecular species present. Generally, a substantially pure composition will comprise more than 80% of all macromolecular species present in the composition, more preferably more than 85%, 90%, 95% and 99%. Most preferably, the active ingredient is purified to essential homogeneity (contaminant species cannot be detected in the composition by conventional detection methods) wherein the composition consists essentially of a single macromolecular species.

Dosing

Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/ml to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In some embodiments, the total dose of aptamers is administered so as to achieve and then maintain a steady state blood concentration equal to at least the $EC_{90}$, which is the concentration of drug that leads to 90% maximal response. Alternatively, the total dose of aptamers is administered so as to achieve and then maintain a steady state blood concentration equal to at least the $EC_{80}$, which is the concentration of drug that leads to 80% maximal response.

The total dosage may be administered in a single dose, multiple doses, repeated doses, as a continual dose or a combination thereof.

In one instance, the formulations are administered with a loading dose, a maintenance dose and a tapered dose.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 1000 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Effective plasma levels of the compounds of the present invention range from 0.002 mg to 50 mg per kg of body weight per day.

Compounds of the present invention may be administered in a single daily dose, or the total daily dosage may be administered in divided doses of two, three or four times daily.

The formulations and dosages described herein are designed to maximize clinical efficacy in the treatment of VAD-mediated diseases and for disorders arising from interactions of VWF multimers with erythrocytes, such as the interaction that occurs between VWF multimers and erythrocytes in sickle cell disease, as well as the treatment of diseases and disorders arising from interactions of VWF monomers or multimers with platelets during the formation of occlusive thrombi that occurs during closing of the lumen of a vessel and/or under very high shear rates ($10,000$ $s^{-1}$ or greater) (such as the disorders of acute coronary syndromes, acute occlusion thrombosis, and ischemic stroke), while simultaneously decreasing or minimizing adverse side effects, without the need for an antidote.

Administration

A pharmaceutical composition described herein can be formulated into a dosage form described herein, such as a topical, intranasal, intratracheal, or injectable (e.g., intravenous, intraocular, intravitreal, intramuscular, intracardiac, intraperitoneal, subcutaneous).

The aptamer formulations provided herein are administered to subjects, preferably human subjects, in an amount effective to prevent, ameliorate or treat thrombotic disorders such as ischemic stroke, diseases or disorders associated with ventricular assist devices and disorders arising from interactions of VWF multimers with erythrocytes, such as the interaction that occurs between VWF multimers and erythrocytes in sickle cell disease.

For oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The compounds of the invention can also be administered in such oral dosage forms as timed release and sustained release tablets or capsules, pills, powders, granules, elixirs, tinctures, suspensions, syrups and emulsions.

Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances.

The compounds of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions. In particular, the materials of the present invention can be delivered to the ocular cavity with the methods described below. In addition, the materials of the present invention can be administered to subjects in the modalities known in the art as described below.

Parenteral injectable administration is generally used for subcutaneous, intramuscular or intravenous injections and infusions. Additionally, one approach for parenteral administration employs the implantation of a slow-release or sustained-release systems, which assures that a constant level of dosage is maintained, according to U.S. Pat. No. 3,710,795, incorporated herein by reference.

Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

The formulations may be administered in combination with other drugs or therapies.

Bioavailability

As used herein, the term "bioavailability" refers to the systemic availability of a given amount of a VWF protective agent administered to a subject. Bioavailability can be assessed by measuring the area under the curve (AUC) or the maximum serum or plasma concentration ($C_{max}$) of the unchanged form of a compound following administration of the compound to a subject. AUC is a determination of the area under the curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, *Modern Pharmaceutics, Drugs and the Pharmaceutical Sciences*, v. 72, Marcel Dekker, New York, Inc., 1996, the contents of which are incorporated herein by reference in their entirety. The $C_{max}$ value is the maximum concentration of the compound achieved in the serum or plasma of a subject following administration of the compound to the subject. The $C_{max}$ value of a particular compound can be measured using methods known to those of ordinary skill in the art.

In some embodiments, VWF protective agents of the present invention are formulated into a composition with a delivery/formulation agent or vehicle as described herein to increase bioavailability. The phrases "increasing bioavailability" or "improving the pharmacokinetics," as used herein mean that the systemic availability of a VWF protective agent, measured as AUC, $C_{max}$, or $C_{min}$ in a subject is greater, when co-administered with a delivery agent as described herein, than when such co-administration does not take place. In some embodiments, the bioavailability of the VWF protective agent can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

V. Kits, Devices and Packaging

Kits and Devices

The VWF protective agent compounds and compositions of the present invention may be combined with other ingredients or reagents or prepared as components of kits or other retail products for commercial sale or distribution.

The kit will contain the compound or composition, along with instructions regarding administration and/or use of the kit. The kit may also contain one or more of the following: a syringe, an intravenous bag or bottle, the same drug in a different dosage form, or another drug. For example, the kit may contain both an intravenous formulation and a subcutaneous formulation of the present invention. Alternatively, the kit may contain lyophilized anti-thrombin aptamer and an intravenous bag of solution. The kit form is particularly advantageous when the separate components must be administered in different dosage forms (i.e., parenteral and oral) or are administered at different dosage intervals.

Preferably, the kits are stored at 5±3° C. The kits can also be stored at room temperature or frozen at −20° C.

The compositions of the present invention which are VWF protective agents may be used in conjunction with one or more therapeutic devices. Such devices include vascular assist devices (VADs), stents, or any device useful in the regulation or management of hemodynamic flow, e.g., associated with blood flow to tissues or organs. The VWF protective agents may be used as coatings on solid surfaces or as adjunct therapy where the pharmaceutical compositions are added in solid or liquid form before, during or after utilization of a device used in the regulation or management of hemodynamic flow. For example, VWF aptamers may be formulated to be added to the blood or plasma flow during surgical procedures such as transplants, angioplasty, and stent insertion or during long-term care such as those patients having internal VAD or LVAD devices implanted.

Packaging

Formulations and/or compositions of VWF protective agents of the present invention can be packaged for use in a variety of pharmaceutically acceptable containers using any pharmaceutically acceptable container closure, as the formulations are compatible with PVC-containing and PVC-free containers and container closures. Examples of pharmaceutically acceptable containers include, but are not limited to, ampules, pre-filled syringes, intravenous bags, intravenous bottles and admix bags. For example, the formulation may be an aqueous formulation containing both anti-thrombin aptamer and pharmaceutically acceptable solvent.

Alternatively, the formulation may contain lyophilized aptamer in one compartment of an admix bag and a pharmaceutically acceptable solvent in a separate compartment of the admix bag such that the two compartments may be mixed together prior to administration to a patient. Pharmaceutically acceptable containers are well known in the art and commercially available. Preferably, the formulations are stored in a Type 1 glass vial with a butyl rubber stopper. The formulations in liquid form must be stored in a refrigerated environment. Preferably, the liquid formulations are stored at 2-8° C. Alternatively, the lyophilized formulations may be stored at room temperature, or refrigerated or frozen.

Preferably, the formulations are sterile. A "sterile" formulation, as used herein, means a formulation that has been brought to a state of sterility and has not been subsequently exposed to microbiological contamination, i.e., the container holding the sterile composition has not been compromised. Sterile compositions are generally prepared by pharmaceutical manufacturers in accordance with current Good Manufacturing Practice ("cGMP") regulations of the U.S. Food and Drug Administration.

Procedures for filling pharmaceutical formulations in pharmaceutically acceptable containers, and their subsequent processing are known in the art. These procedures can be used to produce sterile pharmaceutical drug products often required for health care. See, e.g., Center for Drug Evaluation and Research (CDER) and Center for Veterinary Medicine (CVM), "Guidance for Industry for the Submission Documentation for Sterilization Process Validation in Applications for Human and Veterinary Drug Products" (November 1994). Examples of suitable procedures for producing sterile pharmaceutical drug products include, but are not limited to, terminal moist heat sterilization, ethylene oxide, radiation (i.e., gamma and electron beam) and aseptic processing techniques. Any one of these sterilization procedures can be used to produce the sterile pharmaceutical formulations described herein.

In some embodiments, sterile pharmaceutical formulations can be prepared using aseptic processing techniques. Sterility is maintained by using sterile materials and a controlled working environment. All containers and apparatus are sterilized, preferably by heat sterilization, prior to filling. Then, the container is filled under aseptic conditions, such as by passing the composition through a filter and filling the units. Therefore, the formulations can be sterile filled into a container to avoid the heat stress of terminal sterilization.

In some embodiments, the formulations are terminally sterilized using moist heat. Terminal sterilization can be used to destroy all viable microorganisms within the final, sealed container containing the pharmaceutical formulation. An autoclave is typically used to accomplish terminal heat-sterilization of drug products in their final packaging. Typical autoclave cycles in the pharmaceutical industry to achieve terminal sterilization of the final product are 121° C. for at least 10 minutes.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Where the term "about" is used, it is understood to reflect+/−10% of the recited value.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1. Preparation of Nucleic Acid Aptamers

Nucleic acid aptamers were synthesized on an ÄKTA Oligopilot (Amersham Pharmacia Biotech, Piscataway, N.J.) using standard phosphoramidite solid-phase chemistry. Phosphoramidites were acquired from Hongene Biotechnology Limited, Shanghai, P.R. China. BT-100 (SEQ ID NO: 2) was synthesized with a free amine group attached to the 5'-end through a six carbon-linker.

To prepare BT-200 (SEQ ID NO: 3), BT-100 was first purified through anion-exchange and ultrafiltration before dissolved in 100 mM sodium bicarbonate buffer (pH 8.0) at 10 mg/mL concentration. The purified BT-100 was then mixed with NHS activated branched 40K-PEG (Catalog number Y-NHS-40K, JenKem Technology USA Inc, Plano, Tex.) at the molar ratio of BT-100 to NHS activated branched 40K-PEG to 1:2. The reaction proceeded overnight at the room temperature. The resultant was then purified through anion-exchange and ultrafiltration to get rid of unconjugated 40K-PEG and BT-100, and BT-200 was obtained.

ARC15105 (PEGylated) (SEQ ID NO: 6) was prepared as described previously in Siller-Matula J M, Merhi Y, Tanguay J F et al. *ARC15105 Is a Potent Antagonist of Von Willebrand Factor Mediated Platelet Activation and Adhesion.* Arteriosclerosis, Thrombosis, and Vascular Biology 2012; 32(4):902-909, the contents of which are incorporated herein by reference in its entirety.

Synthesized BT-100 or BT-200 were predicted to naturally form a stem-loop structure (as shown in FIG. 1) when dissolved in aqueous based buffer solution. This was confirmed by several secondary structural prediction models such as Mfold.

Example 2. Vascular Assist Device (VAD) Circuit Analysis: VWF Multimers

Human volunteers donated blood which was split into two aliquots, so that two extracorporeal circuits could be run in parallel, which would permit intra-subject comparison. In addition to inter-subject comparisons.

In vitro extracorporeal circuits were established using left ventricular assist devices (HEARTWARE®) and silicone tubing with blood inlets and outlets. The pump speed was varied between 1800 and 3500 rounds per minute (rpm), and the circulating blood volume was adjusted to approximately 5 liters per minute, to correspond to normal physiologic settings for humans. Anticoagulated blood was left circulating for 1-4 hours in the extracorporeal circuits.

Figure 3:
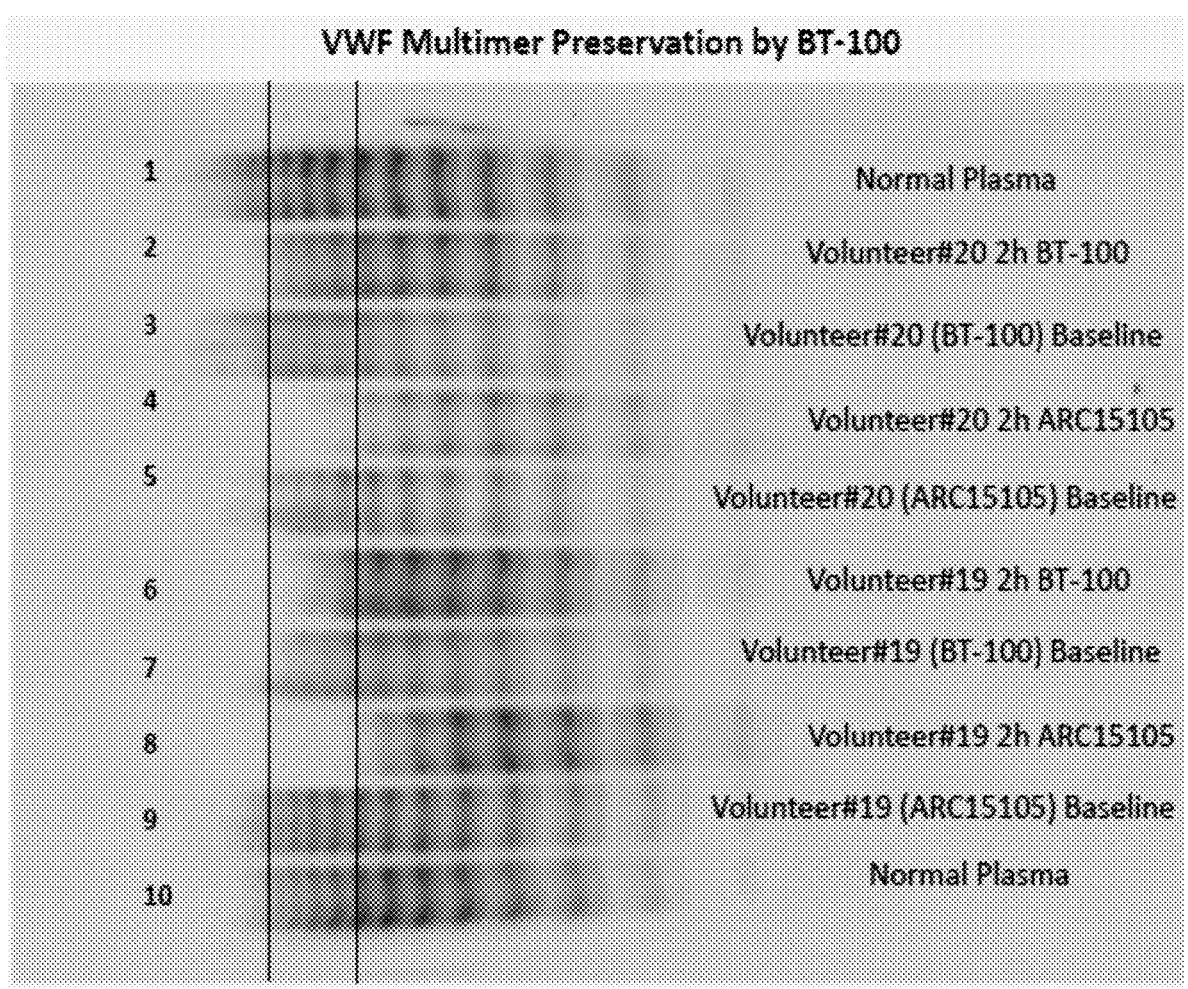
FIG. 3 shows a gel of Von Willebrand Factor multimers and the effects of BT-100 on protection of multimers in human plasma from proteolytic degradation induced by high shear conditions.

Parallel LVAD circuits were run for 2 hours and a minimum of two samples from each circuit were utilized (baseline followed by 2 h). Circuits were run at 37° C. The data are shown in FIG. 3.

Von Willebrand factor multimers were analyzed as described previously (Jilma-Stohlawetz P, et al., *The anti-von Willebrand factor aptamer ARC1779 increases von Willebrand factor levels and platelet counts in patients with type 2B von Willebrand disease*. Thromb Haemost. 2012 August; 108(2):284-90, the contents of which are incorporated herein by reference in their entirety).

Quantification of VWF multimers was performed by sodium dodecyl sulphate-agarose discontinuous gel (1.2%) electrophoresis followed by Western-Blotting and consequent quantification with a luminescence image analyzer (LAS-3000, Raytest GmbH, Berlin, Germany) (Reiter R A, et al., *Changes in ADAMTS13 (von-Willebrand-factor-cleaving protease) activity after induced release of von Willebrand factor during acute systemic inflammation*. Thromb Haemost. 2005 March; 93(3):554-8, the contents of which are incorporated herein by reference in their entirety).

Final analysis was performed using AIDA Image Analyzer software version 4.11.

In the Figure, lanes 1 and 10 are normal plasma (George King Bio-Medical Inc.).

Density analysis of the gels showed that a reduction by 6 mers corresponds to a reduction of 24.9 units to 5.3 or 3.3 units or 87% overall.

In a direct comparison between BT-100 (non-pegylated) and ARC15105 (pegylated molecule), the gel density was reduced from 23 to 5 (by 78%; compare lanes 9 and 8) under ARC15105 (pegylated) as compared to baseline and from 12.6 to 11.5 (by 8%; compare lanes 7 and 6) with BT-100, indicating that BT-100 is able to preserve 92% of the high molecular weight multimer structure.

In a second volunteer, the density on the gel was reduced from 10.0 to 3.6 (by 64%; compare lanes 5 and 4) with ARC15105 (pegylated) as compared to baseline, and from 13.8 to 10.8 (by 22%; compare lanes 3 and 2) with BT-100. From these data it is clear that BT-100 is able to blunt the loss of HMW (high molecular weight) VWF species.

Summary

The ex vivo extracorporeal circuits established proof of concept for a potential therapeutic role of BT-100 in patients with left ventricular assist devices (LVAD) and VWF deficiency syndromes. Circulation of blood in the extracorporeal circuits induced a rapid drop in VWF:RCo and reduced high molecular weight multimers of VWF, resembling the pathophysiological events that occur when an LVAD is implanted into humans.

Up to 14-15 mers were visible in the gels, which were reduced by the high shear stress by a maximum of 6-7 mers to 8 mers. This loss in high molecular weight multimers was significantly blunted by BT-100, whereas equimolar concentrations of ARC15105 did not reduce the maximal loss in multimers.

Example 3. Von Willebrand Ristocetin Cofactor [vWF:RCo] Assay

The Von Willebrand Ristocetin Cofactor [vWF:RCo] assay measures the ability of a patient's plasma to agglutinate platelets in the presence of the antibiotic Ristocetin. The rate of Ristocetin induced agglutination is related to the concentration and functional activity of the plasma Von Willebrand Factor.

Plasma activity of VWF ristocetin cofactor activity (VWF:RCo; primary endpoint) was assayed at 37° C. by turbidometry.

Plasma was pre-incubated with BT-100 or ARC15105 (pegylated) at 37° C. approximately 10 minutes prior to the addition of activating reagent, ristocetin. The assay was conducted (BC von Willebrand reagent; Dade Behring/Siemens, Marburg, Germany) (Reiter R A, et al., *Desmopressin antagonizes the in vitro platelet dysfunction induced by GPIIb/IIIa inhibitors and aspirin*. Blood 2003; 102: 4594-4599, the contents of which are incorporated herein by reference in their entirety).

In a second experiment, whole blood aggregation was determined using multiple electrode aggregometry (MEA) on a new-generation impedance aggregometry (Multiplate Analyzer; Dynabyte) (Derhaschnig U, Jilma B. *Assessment of platelets and the endothelium in patients presenting with acute coronary syndromes—is there a future?* Thromb Haemost 2009; 102: 1144-1148, the contents of which are incorporated herein by reference in their entirety).

The system detects the electrical impedance change due to the adhesion and aggregation of platelets on two independent electrode-set surfaces in the test cuvette. The area under the aggregation curve (AUC) expresses the aggregation response over the measured time (AU×min) which can predict adverse outcome of patients and even bleeding (Sibbing D, et al., *Antiplatelet effects of clopidogrel and bleeding in patients undergoing coronary stent placement*. J Thromb Haemost 2010; 8: 250-256; and Siller-Matula J M et al., *Cross validation of the Multiple Electrode Aggregometry. A prospective trial in healthy volunteers*. Thromb Haemost 2009; 102: 397-403, the contents of which each are incorporated herein by reference in their entirety).

A number of specific Multiplate test reagents (ASPItest, COLtest, TRAPtest, ADPtest, RISTOtest) are available, which permit detection of the role of different receptors/signal transduction pathways (arachidonic acid [AA], thrombin receptor, ADP receptor, collagen receptor, glycoprotein Ib-IX) in platelet activation.

Whole blood was anti-coagulated with hirudin (200 U/ml, Dynabyte) as recommended by the manufacturer and stored at room temperature (22° C.) for 30 minutes (min). Afterwards, 1:2 mixtures of 0.9% NaCl and hirudin-anticoagulated blood were stirred at 37° C. for 3 min in the test cuvettes. Whole blood was pre-incubated with BT-100 or ARC15105 (pegylated) at 37° C. approximately 10 minutes prior to the addition of activating reagent, ristocetin. Thereafter, ristocetin (0.77 mg/ml) was added to separate samples to establish concentration-effect curves. The increase in electrical impedance was recorded continuously for 6 min. The mean values of the two independent determinations are expressed as the AUC of the aggregation tracing. The MEA instrument allows two ways to express the AUC: as arbitrary aggregation units (AU×min) or as units (U). Ten AU×min correspond to 1 U. AUC was measured in U, following the current recommendation of the manufacturer and many recent studies and expressed platelet aggregation as relative increase or decrease as compared to baseline values. The data are given in Tables 1 and 2.

The data show that both aptamers (BT-100 and ARC15105 (pegylated)) inhibited von Willebrand Factor ristocetin co-factor activity. At equimolar concentrations BT-100 exhibited greater potency to inhibit VWF:RCo in both pre- and post-arterial block scenarios.

TABLE 1

Multiplate Analysis

| Multiplate | RISTO baseline | A RISTO BT-100 25 nM | B RISTO BT-100 100 nM | C RISTO ARC15105 25 nM | D RISTO ARC15105 100 nM |
|---|---|---|---|---|---|
| Sample #1 before arterial block AUC (area under curve) | 87 | 5 | 2 | 56 | 56 |
| Sample #1 after arterial block AUC (area under curve) | 105 | 20 | 4 | 56 | 50 |

TABLE 2

Dose Comparisons

| | Subject 1 | | Subject 2 | | Subject 3 | |
|---|---|---|---|---|---|---|
| | BT-100 | ARC15105 | BT-100 | ARC15105 | BT-100 | ARC15105 |
| Baseline | 87 | 87 | 88 | 88 | 107 | 107 |
| 25 nM | ND | ND | ND | ND | 14 | 115 |
| 50 nM | 5 | 56 | 4 | 83 | 8 | 101 |
| 100 nM | 2 | 50 | 5 | 69 | 4 | 94 |
| 200 nM | ND | ND | 2 | 61 | ND | ND |

*data represent area under the aggregation curve

In Ristocetin induced platelet aggregation in whole blood, BT-100 concentrations of 25-50 nM produced 90% inhibition, whereas up to 16-fold higher concentrations of ARC15105 (pegylated) were necessary to reach 90% inhibition ($p<0.05$). These data clearly demonstrate, surprisingly, that BT-100 outperforms ARC15105.

Comparisons between BT-100 and ARC15105 show that BT-100 is up to 25-fold more potent, with an overall average of 10-fold (Compare treatment columns A to C and B to D).

Example 4. Platelet Function Analyzer (PFA-100)

The PFA-100 (Dade Behring, Marburg, Germany) was used for measuring platelet function under high shear rates (5,000-6,000 s$^{-1}$). 4.5 mL blood samples were collected into blood collection tubes containing 3.8% sodium citrate (blood: sodium citrate ratio=9:1). The PFA-100 measures the time required for occlusion of the aperture by platelet plugs, which is defined as closure time (CT). The instrument aspirates a blood sample under constant vacuum from the sample reservoir through a capillary and a microscopic aperture (147 µm) cut into the membrane, which leads to high shear induced platelet plug formation (Jilma et al. 2001). The membrane is coated with collagen/adenosine diphosphate (CADP), which are very sensitive to von Willebrand factor levels. This applies to a deficiency in VWF, its blockade by anti-VWF aptamers as well as VWF release, e.g. by desmopressin or endotoxin (Jilma B. *Platelet function analyzer (PFA-100): a tool to quantify congenital or acquired platelet dysfunction.* J Lab Clin Med 2001; 138: 152-163; Jilma-Stohlawetz et al. 2012; Reiter et al. 2003; Homoncik M, Blann A D, Hollenstein U, Pernerstorfer T, Eichler H G, Jilma B. *Systemic inflammation increases shear stress-induced platelet plug formation measured by the PFA-100.* Br J Haematol. 2000 December; 111(4): 1250-2; and Homoncik M, Jilma B, Hergovich N, Stohlawetz P, Panzer S, Speiser W. *Monitoring of aspirin (ASA) pharmacodynamics with the platelet function analyzer PFA-100.* Thromb Haemost. 2000 February; 83(2):316-21, the contents of each of which are incorporated herein by reference in their entirety).

Since a good correlation exists between VWF levels and PFA-100 measurements, the test is predictive for future thromboembolic events in cardiac patients (Frossard M, Fuchs I, Leitner J M, et al. *Platelet function predicts myocardial damage in patients with acute myocardial infarction.* Circulation 2004; 110: 1392-1397; Fuchs I, Frossard M, Spiel A, et al. *Platelet function in patients with acute coronary syndrome (ACS) predicts recurrent ACS.* J Thromb Haemost 2006; 4: 2547-2552, the contents of which are both incorporated by reference in their entirety).

In this experiment, blood samples were pre-incubated at 37° C. for 10 min with increasing concentrations (ranging from 1-400 nM) of ARC15105 (pegylated) or BT-100. Both anti-VWF aptamers concentration-dependently increased collagen adenosine diphosphate closure-times in the PFA-100, but half maximal inhibitory concentration ($IC_{50}$) values were 3-8 fold higher for ARC15105 (pegylated) as compared to BT-100 ($p<0.05$). Similarly, $IC_{100}$ values were 2-16-fold higher for ARC15105 (pegylated) as compared to BT-100 ($p<0.05$). The data are shown in Tables 3-6.

These experiments unequivocally established superior potency of BT-100 over ARC15105 (pegylated) at equimolar concentrations.

TABLE 3

PFA Results

| PFA 100 | 0 nM | 5 nM | 10 nM | 25 nM | 50 nM | 100 nM |
|---|---|---|---|---|---|---|
| BT-100 | 139 | 135 | 205 | 301 | 301 | 301 |
| ARC15105 | 139 | 94 | 99 | 104 | 128 | 162 |

TABLE 4

PFA Results
Experiment A

| Dose | BT-100 | ARC15105 | native |
|---|---|---|---|
| 0 nM | | | 128 |
| 2 nM | 184 | ND | |
| 5 nM | 156 | ND | |
| 10 nM | 123 | 129 | |
| 15 nM | 277 | ND | |
| 20 nM | 301 | 152 | |
| 25 nM | 301 | ND | |
| 50 nM | ND | 204 | |

TABLE 5

PFA Results Experiment B

| Dose | BT-100 | ARC15105 | native |
|---|---|---|---|
| 0 nM | | | 112 |
| 1 nM | 91 | 88 | |
| 2.5 nM | 97 | 103 | |
| 5 nM | ND | ND | |
| 10 nM | 117 | 96 | |
| 15 nM | 226 | 118 | |
| 20 nM | 301 | 100 | |
| 25 nM | 276 | 112 | |
| 50 nM | 301 | 301 | |
| 100 nM | 208 | 236 | |

TABLE 6

PFA Results Experiment C

| Dose | BT-100 | ARC15105 | native |
|---|---|---|---|
| 0 nM | | | 90 |
| 1 nM | 95 | 82 | |
| 5 nM | 111 | ND | |
| 10 nM | 169 | 83 | |
| 15 nM | 183 | 91 | |
| 20 nM | 284 | 96 | |
| 25 nM | 301 | 109 | |
| 50 nM | 301 | 161 | |
| 75 nM | ND | 223 | |
| 100 nM | ND | 301 | |

In the tables, closure time (in seconds) is given for each treatment. Aggregation is quantified by measuring the time of aperture closure, with a maximum occlusion time of 300 seconds. "Native" refers to normal donor samples that have not been treated, which establishes the "normal" reference level of assay result; "ND" means not tested.

Example 5. Disruption of GpIb and Von Willebrand Factor Binding

The fully-automated INNOVANCE® GpIb and VWF binding assay (VWF:Ac; Siemens Healthcare Diagnostics, Marburg, Germany) measures the activity of von Willebrand Factor in a patient plasma sample, based on the binding of VWF to a recombinant GpIb. Unlike the vWF:RCO assay described in Example 3, the VWF:Ac assay does not require the use of ristocetin, since the recombinant GpIb has two gain-of-function mutations. An increase in extinction by turbidometric measurements is related to increased VWF binding and agglutination. Lawrie A S, et al., *A comparative evaluation of a new automated assay for von Willebrand factor activity*. Haemophilia 2013 March; 19(2):338-342; de Maistre E, et al., *Performance of two new automated assays for measuring von Willebrand activity: HemosIL AcuStar and Innovance*. Throm Haemost. 2014(4), the contents of each of which are herein incorporated by reference in their entirety.

Blood samples were collected from human volunteers. Samples were pre-incubated at 37° C. for 30 minutes with increasing concentrations of BT-100 or ARC15105.

VWF:Ac was measured using an INNOVANCE® VWF Activity kit on Sysmex CS2000i-analyzer (Sysmex UK Ltd), per the manufacturer instructions.

Both aptamers were able to decrease binding activity of VWF and GpIb at high concentrations, but BT-100 showed an enhanced potency as compared to AC 15105, as shown in Table 7.

TABLE 7

Percent (%) binding activity

| Dose | BT-100 | ARC15105 |
|---|---|---|
| 8 nM | 100 | 100 |
| 10 nM | 100 | 100 |
| 30 nM | 92 | 100 |
| 80 nM | 81 | 98 |
| 100 nM | 63 | 95 |
| 300 nM | 40 | 90 |
| 800 nM | 20 | 85 |

Example 6. Blocking the Interaction of Platelets, Leukocytes and Erythrocytes to Von Willebrand Factor In this example, a VWF aptamer is investigated for the ability to block the interaction of platelets, leukocytes, and erythrocytes to von Willebrand factor (VWF) strands that are secreted from activated endothelial cells. The experiment makes use of human components of a recently described in vitro microvessel system (*In vitro microvessels for the study of angiogenesis and thrombosis*. Proc. Natl. Acad. Sci. USA 2012, 109, 9342-9347, the contents of which are herein incorporated by reference in their entirety), which demonstrates the formation of very long, thick VWF strands and cables from activated endothelial cells. These VWF strands are capable of binding platelets and other blood cells, depending on the shear stresses applied. The experiment provides a model of microvascular occlusion in thrombotic microangiopathies such as thrombotic thrombocytopenic purpura and sickle cell disease and tests the ability of the anti-VWF aptamer to interfere with these processes.

Example 7. Prevention of GI Bleeding Caused by Angiodysplasia

In this experiment, a VWF aptamer is investigated in in vitro and in vivo models for the ability to prevent or inhibit an increase in angiogenesis that causes angiodysplasia and results in bleeding in the GI tract.

A VWF aptamer is contacted with Human Umbilical Vein Endothelial Cells (HUVECs) and its ability to inhibit angiogenesis is evaluated. Evaluations are made of vessel network formation, cell migration, cell proliferation and adhesion. Methods for these evaluations are taught in, for example, Starke R D, et al., *Endothelial von Willebrand factor regulates angiogenesis*. Blood, 2011, 117:1071-80, the contents of which are incorporated herein by reference in their entirety.

To evaluate the effect of the VWF aptamer on the overall angiogenic process, HUVECs contacted with VWF aptamer are subjected to in vitro tube formation in a Matrigel assay, which demonstrates the ability of the VWF aptamer to interfere with network formation. One aspect of angiogenesis is cell migration. A Scatch wound assay combined with time lapse microscopy is used to assess the ability of the aptamer to inhibit migration. In this assay, HUVEC cells contacted with the aptamer are evaluated for reduced velocity and directionality of migration. Another aspect of angiogenesis is proliferation. Reduced proliferation of HUVECs contacted with one or more VWF aptamers is measured as a decrease in the number of cells as compared to the untreated control. Yet another aspect of angiogenesis is adhesion of endothelial cells, which is measured in an adhesion assay. Using a commercially available kit (Invitrogen), the inhibitory effect of the VWF aptamer on cell migration can be measured by reduced fluorescence of bound cells in the wells.

ECs derived from circulating progenitor cells, called blood outgrowth endothelial cells (BOECs), from healthy individuals and Von Willebrand's Disease (VWD) patients are isolated according to the methods described in Starke R D, et al., *Endothelial von Willebrand factor regulates angiogenesis*. Blood, 2011, 117:1071-80 and Ingram D A, et al., *Identification of a novel hierarchy of endothelial progenitor cells using human peripheral and umbilical cord blood*. Blood 2004 104:2752-60, the contents of each of which are incorporated herein by reference in their entirety. BOECs are used to evaluate the ability of the VWF aptamer to affect a reduction in or rescue from the increased angiogenesis observed in BOECs from VWD patients, as measured by matrix assay, migration, proliferation, and adhesion assays, observed in the BOECs from VWD patients compared to BOECs from healthy controls.

Mouse models of angiogenesis (reviewed in Couffinhal et al., *Mouse models to study angiogenesis, vasculogenesis and arteriogenesis in the context of cardiovascular diseases*. Frontiers in Bioscience; 2009; 14:3310-25, the contents of which are herein incorporated by reference in their entirety) include ischemic models, such as hindlimb ischemia, heart ischemia and skin models, and non-ischemic models, such as matrigel plug assays, disc assays, eye retina and corneal assays, wound healing and ovarian models. These models are used to evaluate the effect of VWF aptamer delivery on angiogenesis in vivo. In the matrigel plug model, mice are injected with matrigel alone or containing VWF aptamer and the model can be used as described in Couffinhal et al, 2009 and Starke et al, 2011, the contents of each of which are incorporated herein by reference in their entirety, to evaluate the effect of the aptamer on blood vessel formation in the matrigel plug.

Example 8. Prevention of Intracerebral Occlusive Thrombi (Fibrin-Rich Clot Formation)

Experiments are performed on adult, male Swiss mice at 2 months old. N=5-8 animals per group, including the following groups: control-thrombin (saline) and aptamer-thrombin. The mice are housed in a temperature-controlled room on a 12-hour light/12-hour dark cycle with food and water ad libitum. Animals are deeply anesthetized with isoflurane 5% and, thereafter, maintained with 2.5% isoflurane in a 70%/30% mixture of $NO_2/O_2$. A catheter is inserted into the tail vein to allow the intravenous administration (200 µL) of saline or aptamer. A micropipette is filled with 1 µL of purified murine alpha-thrombin (approximately 1000 NIH units/mg; Sigma-Aldrich). Mice are placed in a stereotaxic device, the skin between the right eye and the right ear is incised, and the temporal muscle is retracted. A small craniotomy is performed, the dura is excised, and the middle cerebral artery (MCA) is exposed. 1 µL of purified murine alpha-thrombin (0.75 UI) is injected into the lumen of the MCA to induce the formation of a clot in situ. The pipette is removed 10 minutes after the injection of alpha thrombin to allow the clot to stabilize. To induce thrombolysis, the aptamer is intravenously injected into the tail vein 20 minutes after the injection of alpha-thrombin. The control group receives the same volume of saline under identical conditions.

Cerebral blood flow (CBF) is determined by laser Doppler flowmetry using a fiberoptic probe (Oxford Optronix) glued to the skull in the MCA territory. CBF is measured before the injection of alpha-thrombin (100% baseline) and throughout the duration of the experiment. CBF in the MCA is measured in the presence or absence of aptamer at 1 min, 5 mins, 10 mins, 15 mins, 20 mins, 25 mins, 30 mins, and 60 mins after administration of aptamer or saline. Showing that full occlusion occurs at a later time in the presence of aptamer versus saline control demonstrates that the aptamer slows the rate of occlusion in the MCA. Showing that full occlusion does not occur within 60 minutes indicates that the aptamer prevents occlusive thrombi formation.

In addition, magnetic resonance angiographies are performed using 2D-TOF sequences to measure blood flow (Gaubert et al., J. Thromb Haemost., 2013, the contents of each of which are incorporated herein by reference in their entirety). Also, ischemic brain damage in the MCA area can be assessed by magnetic resonance imaging (MRI) at 6 hours and 24 hours following full occlusion. MRI is carried out on a Pharmascan 7 T/12 cm system using surface coils to determine lesion size, which is quantified on T2 weighted images using ImageJ software. A reduction in lesion size in mice treated with aptamer compared with the lesion size of saline-treated mice indicates that the aptamer prevents or decreases occlusive thrombi formation.

Example 9. Prevention of Intracerebral Occlusive Thrombi (Platelet-Rich Clot Formation)

Experiments are performed on adult, male Swiss mice at 2 months old, N=5-8 animals per group. Mice are anesthetized with 5% isoflurane (Baxter, Paris, France), placed in a stereotaxic device and maintained under anesthesia for up to 2 hours with 2% isoflurane in a 70%/30% mixture of $N_2O/O_2$. The masseter muscle is excised through a skin incision between the right eye and ear, and a small craniotomy (diameter, 1 mm) is performed on the parietal bone to expose the right middle cerebral artery (MCA). Thrombus induction is achieved by placing a piece of WHATMAN™ filter paper strip soaked in freshly prepared $FeCl_3$ (5% to 20%, Sigma Aldrich, Lisle d'Abeau, France) on the intact dura mater, on top of the MCA for 4 minutes. Previous studies in mice have shown that 5% $FeCl_3$ fails to induce thrombosis, while 10% $FeCl_3$ induces partial thrombosis (forming a thrombus "core" formed at shear rates below 10,000 $s^{-1}$) and 20% $FeCl_3$ results in a stable and fully occlusive thrombus (formed at shear rates 10,000 $s^{-1}$ or greater). Cerebral blood flow (CBF) in the MCA territory is determined by laser Doppler flowmetry (Oxford Optronix) which measures blood movements in the probed tissue. CBF is continuously measured before MCA occlusion and throughout the duration of occlusion, ischemia and thrombolysis. Occlusion time is defined as the time between $FeCl_3$ application and CBF diminution below 20% of baseline.

Mice are administered 20% $FeCl_3$ to induce thrombosis. After approximately 4-5 minutes (when cerebral blood flow drops below 50% of basal value, i.e., after partial occlusion), either aptamer or saline (control) is administered to the mice. CBF in the MCA (as measured by Doppler flowmetry) is used to measure the degree of occlusion over time in the presence or absence of aptamer (i.e., occlusion is measured 1 min, 5 mins, 10 mins, 15 mins, 20 mins, 25 mins, 30 mins, and 60 mins after administration of aptamer or saline). Showing that full occlusion occurs at a later time in the presence of aptamer versus saline control demonstrates that the aptamer slows the rate of occlusion in the MCA. Showing that full occlusion does not occur within 60 minutes indicates that the aptamer prevents occlusive thrombi formation after the platelet adhesion phase.

In addition, magnetic resonance angiographies are performed as described in Example 8. Also, ischemic brain damage in the MCA is assessed using magnetic resonance imaging (MRI) at 6 hours and 24 hours following full occlusion as described in Example 8. A reduction in lesion size in mice treated with aptamer compared with the lesion size of saline-treated mice indicates that the aptamer prevents or decreases occlusive thrombi formation after the platelet adhesion phase. Examples of useful positive controls (that can be used in any of Examples 8-12) include aurintricarboxylic acid ("ATA", 20 mg/kg; Sigma-Aldrich), a polycarboxylated compound which binds to the A1 domain of VWF, thus preventing binding of VWF to platelet GpIbα and a monoclonal antibody or antibody fragment to the A1 domain of VWF which prevents binding to platelet GpIbα, i.e., Fab fragments of the monoclonal antibody Xia.B2 (2.5 mg/kg, Emfret Analytics, Wurzburg, Germany). Examples of useful negative controls include GR144053 trihydrochloride ("GR", 10 mg/kg; R&D Systems, Lille, France), a non-peptidic GpIIb/IIIa inhibitor, and a monoclonal antibody or antibody fragment to GpIIb/IIIa, i.e., Fab fragments of the monoclonal antibody Leo.H4 (2.5 mg/kg, Emfret Analytics, Würzburg, Germany). ATA and GR solutions are passed through 0.22 µm filters prior to administration and subsequently injected as a rapid bolus (200 µL). Control IgG (rat) can be purchased from Jackson Immunoresearch. Fab fragments are prepared using Pierce Fab preparation kit (Fisher scientific, Illkirch, France) according to the manufacturer instructions Example 10. Disaggregation of Intracerebral Occlusive Thrombi Inhibition of GpIbα-VWF interactions should disengage the VWF that cross-links platelets in the VWF-rich portion of the thrombus, thus restoring vessel patency. The mouse model of MCA thrombosis described in Example 9 is used to show the disaggregation of occlusive thrombi in the presence of aptamer. Mice with fully occlusive thrombi are generated using 20% $FeCl_3$ as described in Example 9. Saline (control) or aptamer is administered to the mice intravenously at 10 minutes following full occlusion as measured by cerebral blood flow (CBF) in the MCA as determined by laser Doppler flowmetry (CBF diminution below 20% of baseline is considered full occlusion). Immunohistological analyses of thrombi from mice euthanized 10 minutes after administration of aptamer (e.g., 20 minutes after full occlusion) is performed using fluorescently-labeled antibodies against VWF and CD41 (platelet marker) and DAPI nuclear staining of MCA. The observation of less VWF and CD41 in the MCA (as measured by fluorescence staining) in aptamer-treated mice compared with control mice indicates disaggregation of the thrombi in the presence of aptamer. Also, in other test mice, the MCA can be re-opened and examined to determine the size of the thrombus in aptamer-treated versus saline-treated mice. Examples of useful positive controls include ATA and Xia.B2. Examples of useful negative controls include GR144053 trihydrochloride and a monoclonal antibody or antibody fragment to GpIIb/IIIa.

Example 11: Restoration of Vessel Patency

The mouse model of MCA thrombosis described in Example 9 is used to show the restoration of vessel patency in the presence of the aptamer. Mice with fully occlusive thrombi are generated using 20% $FeCl_3$ as described in Example 9. Saline (control) or aptamer is administered to the mice intravenously or subcutaneously at 20 minutes following full occlusion. Doppler flowmetry is used to determine the cerebral blood flow (CBF) in the MCA, with an observed increase in CBF in the aptamer-treated mice compared with the saline-treated mice demonstrating the restoration of vessel patency. In addition, magnetic resonance angiographies are performed using 2D-TOF sequences to measure blood flow and ischemic brain damage in the MCA area is assessed by magnetic resonance imaging (MRI) at 6 hours and 24 hours following occlusion. MRI is carried out as described in Example 9. A reduction in lesion size in mice treated with aptamer compared with the lesion size of saline-treated mice indicates the restoration of vessel patency. Similar methods can be used to determine restoration of patency in larger arteries, such as the carotid artery, using the $FeCl_3$ model of thrombosis and monitoring via Doppler flowmetry MRI, and immunohistological analyses, as previously described.

Example 12. Photochemically Induced Thrombotic Middle Cerebral Artery Occlusion in Non-Human Primate Experiments are performed on adult, male non-human primates (NHP i.e., cynomolgus, squirrel or rhesus monkey) at 7-13 years old. N=2-3 animals per group, including the following groups: control (saline) and aptamer (BT-100). The NHP are housed in a temperature-controlled room on a 12-hour light/12-hour dark cycle with food and water ad libitum. Animals are lightly anesthetized with an intramuscular injection of 10 mg/kg ketamine hydrochloride, intubated and anesthesia maintained with 0.5% to 1.5% isoflurane in 30% 02. Body temperature is monitored continually and maintained at 37 to 39° C. with a heating pad. A catheter is inserted into the femoral vein to allow the intravenous administration of rose bengal, saline or BT-100 aptamer. The transorbital approach to the right MCA is performed as described in Maeda M, Moriguchi A, Mihara K, Aoki T, Takamatsu H et al. *FK419, a nonpeptide platelet glycoprotein IIb/IIIa antagonist, ameliorates brain infarction associated with thrombotic focal cerebral ischemia in monkeys: comparison with tissue plasminogen activator.* J Cereb Blood Flow Metab. 2005 January; 25:108-118, the contents of which are herein incorporated by reference in their entirety. An orbital craniotomy is performed, permitting visualization of the right MCA while keeping the dura mater intact. The region is then irradiated with green light (wavelength 540 nm) for 10 minutes coincidentally with 6 minutes of intravenous rose Bengal administration (20 mg/kg). The treatment (saline or aptamer) is applied at the end of the photoirradiation.

Cerebral blood flow (CBF) is determined by laser Doppler flowmetry using a fiberoptic probe (Oxford Optronix) placed on the MCA. CBF is measured before the photoirradiation and for up to 3 hrs following aptamer administration. CBF in the MCA is measured in the presence or absence of BT-100 aptamer at 1 min, 5 mins, 10 mins, 15 mins, 20 mins, 25 mins, 30 mins, 60 mins, 120 mins and 180 mins after administration of BT-100 aptamer or saline. Showing that full occlusion occurs at a later time in the presence of BT-100 aptamer versus saline control demonstrates that the aptamer slows the rate of occlusion in the MCA. Showing that full occlusion does not occur within 60 minutes indicates that the aptamer prevents occlusive thrombi formation. Showing that presence of BT-100 aptamer versus saline control shortens the period to reperfusion and/or prevents reocclusion after reperfusion indicates the ability of BT-100 to disaggregate occlusive thrombi.

Non-human primates are examined for neurological deficits 24 hrs after photothrombosis. Improved neurological performance in NHP treated with BT-100 aptamer vs saline suggests a faster or more efficient disaggregation of occlusive thrombi.

Example 13. Aptamer Design for Extending Duration of Action

Aptamers are optimized to improve one or more desired characteristics or properties of the aptamer. Such characteristics or properties include improvements in binding affinity, pharmacokinetic or pharmacodynamic properties, thermostability, potency, or any other characteristic or property known to one with skill in the art.

In one example, aptamers are optimized by altering the stem. The stem length may either be increased or decreased. In one embodiment, the stem length is extended and made longer. The duplexed region of the stem may be altered to be made shorter, longer or to alter the symmetry or asymmetry. Branches may be added to the stem of the aptamer.

In one example, aptamers are optimized by adding or altering one or more conjugates and/or terminal cap structures. The conjugate may be a polyethelyene glycol (PEG) moiety or any other conjugate or terminal cap known in the art. One or more conjugates are added to the aptamer to improve the desired characteristics or properties. Further, the conjugate(s) may be at the 5' or the 3' end of the aptamer.

In one example, aptamers are optimized to increase thermostability, by increasing the double stranded region of the stem to exceed 6 base pairs.

Optimized aptamers may be tested by any of the methods known in the art for assessing the desired characteristic and/or property, including those described herewithin. The optimized aptamers should exceed the performance of the equivalent, but unoptimized aptamer in at least one characteristic and/or property.

Example 14. Optimization of ARC15105 to Generate BT-200

ARC15105 is optimized to generate BT-200. The optimization is to improve thermostability and pharmacokinetic and pharmacodynamic properties such as half-life and/or duration of action. The duplexed stem region of ARC15105 is elongated from a 5-base pair duplex to a 9-base pair duplex. The extension of the stem region increases the thermostability of BT-200 and stabilizes the integrity of the aptamer, thus making it less susceptible to nuclease cleavage and prolonging the in vivo half-life and/or duration of action of the aptamer. The 40 kD PEG is retained for BT-200. The characteristics and/or properties of BT-200 are tested by any of the methods known in the art and/or described herewithin. In a direct comparison, optimized aptamer BT-200 will outperform original aptamer ARC15105.

Example 15. Optimization of BT-100 to Generate BT-200

BT-100 is optimized to generate BT-200. The 40 kD PEG is conjugated to the 5' terminus of the BT-100. By increasing the molecular mass of the aptamer and shielding them from nucleases, pegylation improves pharmacokinetics and pharmacodynamics properties such as half-life and/or duration of action. The characteristics and/or properties of BT-200 are tested by any of the methods known in the art and/or described herewithin.

Example 16. In Vitro Blocking of VWF Activity Assay (REAADS)

BT-200 was evaluated for in vivo inhibition of the VWF activity. The REAADS® von Willebrand Factor Activity Test Kit (Diapharma, Catalog #: K10826, West Chester, Ohio) was utilized to measure functional VWF in plasma samples. The assay was adapted to evaluate inhibition of VWF activity by BT-200. The test kit is an enzyme-linked immunosorbent assay (ELISA) that uses a purified murine anti-VWF monoclonal antibody to detect the A1 domain of VWF.

Whole blood was drawn from three cynomolgus monkeys (Xishan Zhongke Laboratory Animal Co., Suzhou, China) into blood collection tubes containing 3.2% sodium citrate (blood:sodium citrate ratio=9: 1). Plasma was separated by centrifugation at 3000 rpm. BT-200 stock solution was prepared as 1 mg/ml in phosphate-buffered saline (PBS). BT-200 was spiked into plasma samples to final concentrations of 10, 30, 100, 300, 1000, 3000, 10000, and 30000 ng/ml. The REAADS assay was performed according to manufacturer's instruction at room temperature. VWF activity was reported in percent (%) of normal, relative to a calibrator that has been standardized against the third International Standard for Factor VIII and von Willebrand Factor in Plasma (91/666). VWF activity was plotted against BT-200 concentration to determine $IC_{50}$ values.

Results of the in vitro REAADS assay are presented in Table 8. The data shows a dose-dependent inhibition of VWF A1 domain activity by BT-200 in monkey plasma. The $IC_{50}$ values determined for each animal were 1618 ng/ml ($R^2=0.998$), 1633 ng/ml ($R^2=0.999$), and 1606 ng/ml ($R^2=0.997$), respectively. The study confirms that BT-200 inhibits VWF activity by blocking the A1 domain of VWF.

TABLE 8

| BT-200 concentration (ng/ml) | VWF activity Percent (%) of normal | | |
|---|---|---|---|
| | Animal A | Animal B | Animal C |
| 30000 | 0.6 | 0.6 | 0.6 |
| 10000 | 4.7 | 5.6 | 4.5 |
| 3000 | 28.6 | 31.2 | 22.3 |
| 1000 | 72.4 | 72.4 | 74.3 |
| 300 | 98.7 | 98.4 | 94.9 |
| 100 | 105.8 | 104.5 | 104.5 |
| 30 | 101.9 | 109.0 | 97.5 |
| 10 | 110.0 | 111.2 | 103.5 |
| 0 | 111.2 | 109.8 | 105.9 |

Example 17. In Vivo Blocking of VWF Activity Assay (REAADS)

An in vivo experiment was carried out to assess BT-200 inhibition of VWF activity in monkeys. Three adult cynomolgus monkeys were administered 3 mg/kg BT-200 by intravenous injection (I.V.), 1 mg/kg, and 3 mg/kg BT-200 by subcutaneous injection (S.C.), respectively. VWF activity was assayed at 1 h, 4 h, 8 h, 24 h, 48 h, 96 h, 168 h, 240 h, and 336 h post injection using the REAADS test kit. The REAADS assay was performed as described in Example 16 to determine VWF A1 domain activity.

Results of the REAADS assay are presented in Table 9. The inhibition of BT-200 on VWF activity lasted more than 336 hours with a dose of 3 mg/kg administered either intravenously or subcutaneously. BT-200 blocked the VWF activity for more than 168 hours with a dose of 1 mg/kg by S.C. injection. These data indicated high affinity between BT-200 and the A1 domain of VWF in vivo.

TABLE 9

| | VWF activity | | |
|---|---|---|---|
| | Percent (%) of normal | | |
| Sample time | Animal A 3 mg/kg I.V. | Animal B 1 mg/kg S.C. | Animal C 3 mg/kg S.C. |
| 0 | 111.2 | 109.8 | 105.9 |
| 1 h | 0.2 | 62.6 | 94.0 |
| 4 h | 0.1 | 13.3 | 16.4 |
| 8 h | 0.1 | 4.4 | 4.0 |
| 24 h | 0.2 | 3.0 | 0.5 |
| 48 h | 0.4 | 5.7 | 0.4 |
| 96 h | 1.9 | 6.1 | 0.4 |
| 168 h | 9.1 | 60.6 | 4.3 |
| 240 h | 33.0 | 122.7 | 21.6 |
| 336 h | 79.9 | 122.3 | 62.3 |

Example 18. In Vitro Platelet Function Analyzer (PFA-200) Assay

BT-200 was assessed for the ability to inhibit VWF activity in vitro using the PFA assay as described in Example 4. Both human donor plasma samples and cynomolgus monkey plasma samples were utilized. Plasma samples were prepared by drawing 4.5 mL whole blood into blood collection tubes containing 3.2% sodium citrate (blood:sodium citrate ratio=9:1). BT-200 stock solution was prepared as 1 mg/ml in PBS. BT-200 was spiked into the human samples to final concentrations of 0.001, 0.003, 0.01, 0.03, 0.06, 0.1, 0.2, 0.3, 1.0, 3.0, 10.0 and 30.0 ug/mL. In monkey samples, concentrations of BT-200 were adjusted to 0.01, 0.1, 0.4, 0.6, 0.8, 1.0, 3.0 and 10.0 ug/mL. After incubation at 37° C. for 15 min, platelet plug formation was measured by collagen/adenosine diphosphate-induced closure time (CADP-CT) with a platelet function analyzer, PFA-200 (Siemens, Marburg, Germany). Normal saline was used as negative control. Maximal CT measured by PFA-200 is 5 min and the instrument gives a result >300 s if this time is exceeded. Data was plotted against BT-200 concentration and fitted in GraphPad Prism 5 (San Diego, Calif.) to obtain median effective dose ($ED_{50}$) values.

For human samples, data was collected from 14 healthy volunteers enrolled at Suzhou University, China. Closure time of the samples after incubation with BT-200 was analyzed. Analysis of variance (ANOVA) results indicated that concentration of BT-200 beyond 0.2 ug/ml prolonged CADP-CT significantly (P<0.01). BT-200 produced concentration-dependent prolongation of CADP-CT. $ED_{50}$ was calculated to be 0.187 ug/ml, with a 95% credibility interval of 0.086-0.408 ug/ml ($R^2$=0.940). Data is shown in Table 10.

TABLE 10

| | Closure time of human volunteers | | | | | | | | | | | | | |
|---|---|---|---|---|---|---|---|---|---|---|---|---|---|---|
| BT-200 | Closure Time (s) | | | | | | | | | | | | | |
| (ug/ml) | H1 | H2 | H3 | H4 | H5 | H6 | H7 | H8 | H9 | H10 | H11 | H12 | H13 | H14 |
| 30.0 | 300 | 300 | 300 | 300 | 300 | 300 | 300 | — | — | — | — | — | — | — |
| 10.0 | 300 | 300 | 300 | 300 | 300 | 300 | 300 | 300 | 300 | 300 | 300 | 300 | 300 | 300 |
| 3.0 | 300 | 300 | 300 | 300 | 300 | 300 | 300 | 300 | 300 | 300 | 300 | 300 | 300 | 300 |
| 1.0 | 300 | 300 | 300 | 300 | 300 | 300 | 300 | 300 | 300 | 300 | 300 | 300 | 300 | 300 |
| 0.3 | 275 | 300 | 300 | 267 | 300 | 300 | 300 | 243 | 191 | 300 | 258 | 300 | 300 | 300 |
| 0.2 | — | — | — | — | — | 164 | 258 | 145 | 108 | 260 | 128 | 137 | 201 | 237 |
| 0.1 | 110 | 127 | 237 | 111 | 190 | 109 | 174 | 99 | 86 | 165 | 91 | 134 | 182 | 158 |
| 0.06 | — | — | — | — | — | — | — | 91 | 77 | 145 | 83 | 115 | 157 | 113 |
| 0.01 | 74 | 109 | 122 | 102 | 127 | 82 | 104 | 85 | 73 | 121 | 77 | 112 | 133 | 103 |
| 0.003 | 85 | 85 | 130 | 83 | 106 | 83 | 121 | 77 | 85 | 117 | 68 | 84 | 103 | 93 |
| 0.001 | 77 | 101 | 98 | 101 | 113 | 69 | 92 | 73 | 79 | 113 | 80 | 95 | 100 | 95 |
| Blank | 77 | 81 | 113 | 87 | 126 | 79 | 117 | 70 | 63 | 112 | 69 | 84 | 111 | 103 |

For monkey samples, data was collected from 16 cynomolgus monkeys (Xishan Zhongke Laboratory Animal Co. (Suzhou, China)). Closure time of the samples after incubation with BT-200 was analyzed. ANOVA results indicated that concentration of BT-200 beyond 0.6 ug/ml prolonged CADP-CT significantly (P<0.01). BT-200 produced concentration-dependent prolongation of CADP-CT. $ED_{50}$ was calculated to be 0.697 ug/ml, with a 95% credibility interval of 0.135-3.599 ug/ml ($R^2$=0.852). Data is shown in Table 11.

TABLE 11

Closure time of cynomolgus monkeys

| BT-200 (ug/ml) | Closure Time (s) | | | | | | | |
| --- | --- | --- | --- | --- | --- | --- | --- | --- |
| | M1 | M2 | M3 | M4 | M5 | M6 | M7 | M8 |
| 10.00 | 300 | 300 | 300 | 300 | 300 | 300 | 300 | 300 |
| 3.00 | — | — | 300 | 300 | 300 | 300 | 300 | 300 |
| 1.00 | 215 | 300 | 300 | 300 | 300 | 300 | 300 | 300 |
| 0.80 | — | — | 179 | 105 | 300 | 300 | 300 | 176 |
| 0.60 | 65 | 152 | 109 | 96 | 130 | 300 | 101 | 130 |
| 0.40 | 56 | 86 | 73 | 57 | 90 | 88 | 68 | 104 |
| 0.10 | — | 55 | 56 | 53 | 63 | 54 | 59 | 75 |
| 0.01 | 52 | 59 | 51 | 46 | 50 | 54 | 49 | 63 |
| Blank | 55 | 55 | 54 | 53 | 57 | 50 | 50 | 75 |
| | M9 | M10 | M11 | M12 | M13 | M14 | M15 | M16 |
| 10.00 | 300 | 300 | 300 | 300 | 300 | 300 | 300 | 300 |
| 3.00 | 300 | 300 | — | — | — | — | — | — |
| 1.00 | 300 | 212 | 300 | 300 | 300 | 300 | 300 | 300 |
| 0.80 | 300 | 141 | 300 | 300 | 80 | 158 | 300 | 300 |
| 0.60 | 170 | 82 | — | 300 | 75 | 72 | 153 | 106 |
| 0.40 | 91 | 78 | 133 | 137 | 60 | 53 | 79 | 72 |

TABLE 11-continued

Closure time of cynomolgus monkeys

| 0.10 | 61 | 58 | — | — | — | — | — | — |
| --- | --- | --- | --- | --- | --- | --- | --- | --- |
| 0.01 | 76 | 63 | 58 | 73 | 53 | 40 | 49 | 50 |
| Blank | 66 | 56 | 58 | 73 | 53 | 40 | 49 | 50 |

In both sets of samples, BT-200 produced concentration-dependent inhibition of VWF activity. The mean $ED_{50}$ to prolong human or cynomolgus monkey CADP-CT was 0.158±0.105 ug/ml (n=14) and 0.576±0.390 ug/ml (n=16), respectively. The affinity of BT-200 binding to human VWF was 3.72 times higher than monkey VWF.

Example 19. In Vivo PFA-200 Assay

BT-200 was evaluated in cynomolgus monkeys for in vivo inhibition of VWF activity. Sixteen adult monkeys were selected and distributed into four treatment groups according to sex and weight. The monkeys weighed between 2.6 to 3.9 kg, and aged 3 to 5 years old. Each group contained four animals, two males and two females, and the average weight of each group was about 3.2 kg. BT-200 dosing solutions were prepared in 0.9% saline to a final concentration of 10 mg/ml. Groups 1-4 were administered 3 mg/kg BT-200 by intravenous injection (I.V.), 3.0 mg/kg, 1.0 mg/kg, and 5.0 mg/kg BT-200 by subcutaneous injection (S.C.), respectively. Blood samples were collected at 30 min before injection (−30 min), 1 h, 4 h, 12 h, 24 h, 48 h, 96 h, 168 h, and 240 h after injection. Plasma samples were prepared as described previously. CADP-CT measurement was performed with PFA-200 immediately upon sample collection.

Closure time of cynomolgus monkey pre- or post-BT-200 injection was expressed as mean±standard deviation (SD) (see Table 12), respectively. ANOVA results indicated that BT-200 prolonged CADP-CT significantly in all 4 groups 1 h after injection (P<0.01). The inhibition of BT-200 on VWF in vivo maintained at least to 240 h. ANOVA results indicated that, 1 h after injection, CADP-CTs of 4 groups were without significant difference. Moreover, the data suggested that BT-200 has a long half-life and subcutaneous injection bioavailability of BT-200 is similar as intravenous injection.

TABLE 12

Closure time (s) at different time points

| Sample time | 3 mg/kg I.V. | 3 mg/kg S.C. | 1 mg/kg S.C. | 5 mg/kg S.C. |
|---|---|---|---|---|
| −30 min | 73.5 ± 3.0 | 79.5 ± 2.4 | 73.8 ± 2.4 | 86.0 ± 5.8 |
| 1 h | 300 ± 0.0 | 255.0 ± 52.6 | 271.3 ± 57.5 | 300.0 ± 0.0 |
| 4 h | 300.0 ± 0.0 | 300.0 ± 0.0 | 300.0 ± 0.0 | 300.0 ± 0.0 |
| 8 h | 300.0 ± 0.0 | 300.0 ± 0.0 | 300.0 ± 0.0 | 300.0 ± 0.0 |
| 24 h | 300.0 ± 0.0 | 300.0 ± 0.0 | 300.0 ± 0.0 | 300.0 ± 0.0 |
| 48 h | 300.0 ± 0.0 | 300.0 ± 0.0 | 300.0 ± 0.0 | 300.0 ± 0.0 |
| 96 h | 300.0 ± 0.0 | 300.0 ± 0.0 | 300.0 ± 0.0 | 300.0 ± 0.0 |
| 168 h | 300.0 ± 0.0 | 300.0 ± 0.0 | 300.0 ± 0.0 | 300.0 ± 0.0 |
| 240 h | 300.0 ± 0.0 | 300.0 ± 0.0 | 300.0 ± 0.0 | 300.0 ± 0.0 |

Example 20. Coagulation Function

Coagulation parameters including activated partial thromboplastin time (aPTT), prothrombin time (PT), thrombin time (TT) and fibrinogen (FIB) were assayed by an automatic coagulometer (Stago, France) at 30 min before injection (pre-dose), 15 min, 1 h, 4 h, 8 h, 24 h, 48 h, 96 h, 168 h and 240 h after injection from the same 16 monkeys as in Example 19.

BT-200 prolonged aPTT significantly 1 h after intravenous injection, which maintained to 48 h. Subcutaneous injection of BT-200 prolonged aPTT later than intravenous injection. ANOVA results indicated that, 24 h after 1 mg/kg BT-200 subcutaneous injection, aPTT was prolonged significantly (P=0.03) and reclined to baseline at 48 h. 8 h after 3 mg/kg BT-200 subcutaneous injection, aPTT was prolonged significantly (P<0.05) and maintained to 96 h after injection. When injected 5 mg/kg BT-200, aPTT prolonged from 8 h after injection and maintained to 240 h. The PT, TT and FIB values did not change after BT-200 injection. The results indicate that BT-200 does not have effects on these coagulation factors except for aPTT. However, aPTT prolongation is an artifact as explained in Example 21.

Coagulation parameters of each group at different time points are presented in Tables 13-16. In the tables, aPTT, PT, TT and FIB values are presented as mean±SD (n=4); * indicates very significant difference (P<0.01); and # indicates significant difference (0.01<P<0.05).

TABLE 13

Activated Partial Thromboplastin Time (aPTT) (s)

| Sample time | 3 mg/kg I.V. | 3 mg/kg S.C. | 1 mg/kg S.C. | 5 mg/kg S.C. |
|---|---|---|---|---|
| −30 min | 31.2 ± 3.0 | 31.6 ± 2.4 | 29.4 ± 2.4 | 30.3 ± 5.8 |
| 1 h | 60.3 ± 2.9* | 34.7 ± 4.6 | 28.1 ± 4.7 | 29.7 ± 4.7 |
| 4 h | 61.4 ± 6.8* | 39.7 ± 8.2 | 29.1 ± 5.1 | 39.5 ± 10.4 |
| 8 h | 59.7 ± 3.5* | 47.1 ± 10.8* | 34.3 ± 3.5 | 53.3 ± 9.4* |
| 24 h | 60.7 ± 7.4* | 58.8 ± 9.4* | 36.0 ± 2.8# | 48.6 ± 6.0* |
| 48 h | 54.7 ± 3.9* | 54.4 ± 7.2* | 34.0 ± 5.2 | 48.6 ± 6.0* |
| 96 h | 37.5 ± 4.8 | 42.8 ± 4.9# | 30.7 ± 4.6 | 44.6 ± 4.4* |
| 168 h | 32.6 ± 6.9 | 38.1 ± 7.6 | 27.1 ± 4.3 | 45.3 ± 4.8* |
| 240 h | 26.7 ± 4.4 | 29.9 ± 6.2 | 27.6 ± 4.7 | 40.7 ± 8.9# |

TABLE 14

Prothrombin Time (PT) (s)

| Sample time | 3 mg/kg I.V. | 3 mg/kg S.C. | 1 mg/kg S.C. | 5 mg/kg S.C. |
|---|---|---|---|---|
| −30 min | 16.6 ± 5.7 | 12.8 ± 0.7 | 13.3 ± 0.5 | 12.9 ± 1.1 |
| 1 h | 13.3 ± 0.7 | 15.1 ± 2.5 | 12.7 ± 0.9 | 12.2 ± 0.5 |
| 4 h | 14.2 ± 1.8 | 13.2 ± 1.0 | 12.7 ± 0.9 | 12.1 ± 0.6 |
| 8 h | 14.3 ± 1.3 | 15.9 ± 4.2 | 12.4 ± 0.2 | 11.9 ± 0.5 |
| 24 h | 13.9 ± 1.2 | 12.8 ± 1.6 | 11.4 ± 0.5 | 11.3 ± 0.4 |
| 48 h | 13.1 ± 0.7 | 12.7 ± 1.7 | 11.1 ± 0.2 | 11.1 ± 0.5 |
| 96 h | 11.5 ± 0.4 | 11.1 ± 0.3 | 11.3 ± 0.2 | 11.3 ± 0.7 |
| 168 h | 12.7 ± 0.7 | 11.5 ± 0.7 | 11.6 ± 0.2 | 11.6 ± 0.9 |
| 240 h | 12.9 ± 0.8 | 11.7 ± 0.1 | 11.7 ± 0.2 | 12.2 ± 1.0 |

TABLE 15

Thrombin Time (TT) (s)

| Sample time | 3 mg/kg I.V. | 3 mg/kg S.C. | 1 mg/kg S.C. | 5 mg/kg S.C. |
|---|---|---|---|---|
| −30 min | 19.4 ± 2.8 | 20.6 ± 1.7 | 18.3 ± 0.4 | 19.1 ± 3.1 |
| 1 h | 18.9 ± 1.2 | 23.3 ± 2.5 | 18.4 ± 0.6 | 20.7 ± 2.9 |
| 4 h | 22.5 ± 4.1 | 20.9 ± 1.8 | 19.5 ± 3.1 | 21.5 ± 2.7 |
| 8 h | 19.8 ± 1.0 | 25.2 ± 3. | 19.2 ± 2.6 | 23.0 ± 2.9 |
| 24 h | 19.7 ± 1.8 | 21.1 ± 3.0 | 20.4 ± 1.0 | 22.9 ± 4.1 |
| 48 h | 20.1 ± 3.2 | 21.5 ± 4.3 | 20.5 ± 0.5 | 20.9 ± 0.7 |
| 96 h | 22.1 ± 1.6 | 21.7 ± 1.5 | 20.5 ± 0.8 | 20.7 ± 0.6 |
| 168 h | 22.1 ± 2.8 | 21.4 ± 1.4 | 20.4 ± 1.0 | 20.5 ± 0.5 |
| 240 h | 21.4 ± 1.1 | 21.7 ± 0.8 | 20.9 ± 0.6 | 21.0 ± 0.5 |

TABLE 16

Fibrinogen Concentrations (g/L)

| Sample time | 3 mg/kg I.V. | 3 mg/kg S.C. | 1 mg/kg S.C. | 5 mg/kg S.C. |
|---|---|---|---|---|
| −30 min | 2.80 ± 1.75 | 3.57 ± 0.78 | 2.76 ± 0.82 | 2.48 ± 0.69 |
| 1 h | 2.88 ± 1.94 | 2.60 ± 0.38 | 2.38 ± 0.41 | 2.91 ± 0.43 |
| 4 h | 2.73 ± 0.82 | 3.38 ± 0.84 | 2.41 ± 0.59 | 2.62 ± 0.39 |
| 8 h | 2.38 ± 1.11 | 2.62 ± 0.64 | 3.42 ± 0.90 | 3.08 ± 0.58 |
| 24 h | 2.64 ± 1.33 | 3.22 ± 0.22 | 3.28 ± 0.77 | 3.01 ± 0.73 |
| 48 h | 2.85 ± 1.45 | 2.84 ± 0.42 | 2.97 ± 0.57 | 2.85 ± 0.44 |
| 96 h | 3.40 ± 1.17 | 3.35 ± 0.30 | 3.07 ± 0.45 | 2.87 ± 0.53 |
| 168 h | 3.28 ± 1.70 | 3.40 ± 1.10 | 3.00 ± 1.13 | 2.89 ± 0.63 |
| 240 h | 3.14 ± 1.53 | 3.32 ± 0.78 | 2.62 ± 0.97 | 2.82 ± 0.27 |

Example 21. Additional Coagulation Assays

A. aPTT Assays

As BT-200 was not previously shown to be an anticoagulant, it was not expected to prolong clotting time. The observed prolonged aPTT in Example 20 was further investigated. The aPTT assay was repeated using aPTT reagents Actin-FS (Siemens, Marburg, Germany) and aPTT-lupus anticoagulant (LA) (Stago, France) with either silica or ellagic acid as a clot activator. Actin-FS is the most sensitive reagent to mild reductions of factors VIII, IX, and XI. The results revealed that the spurious aPTT effect is reagent specific (see Table 17). While aPTT reagents with silica as activator showed increased aPTT values in the presence of BT-200, aPTT Actin-FS with ellagic acid exhibited the same aPTT value at all BT-200 concentrations.

TABLE 17 aPTT assays

| BT-200 concentration (ug/ml) | 0 | 3 | 10 | 30 | 100 | Activator | Manufacturer |
|---|---|---|---|---|---|---|---|
| aPTT (s) | 40.1 | 48.6 | 65.1 | 77.3 | 83.2 | silica | Stago |
| aPTT Actin-FS (s) | 40.9 | 41.1 | 40.9 | 40.2 | 40.3 | ellagic acid | Stago |
| aPTT-LA (s) | 40.9 | 44.8 | 65.7 | 82.5 | 98.7 | silica | Stago |

The effect of BT-200 on coagulation factors were also evaluated with ellagic acid as activator. The results are presented in Table 18. As expected, BT-200 does not decrease Factor VIII or Factor XI activity.

TABLE 18

Factor activity

| BT200 concentration (ug/ml) | 0 | 3 | 10 | 30 | 100 | Activator | Manufacturer |
|---|---|---|---|---|---|---|---|
| Anti-Xa (heparin) (IU/ml) | <0.1 | <0.1 | <0.1 | <0.1 | <0.1 | | |
| Factor VIII activity (%) | 59 | 58 | 58 | 60 | 60 | ellagic acid | Siemens |
| Factor XI activity (%) | 80 | 79 | 81 | 79 | 80 | ellagic acid | Siemens |

Although coagulation assays such as PT and aPTT are widely performed, they are known to have intrinsic limitations. For example, these assays evaluate the clotting cascade in isolation and are thus non-physiological. As a result, they usually show a poor correlation with the clinical phenotype, i.e., the PT or aPTT may be prolonged but this does not necessarily predict the bleeding phenotype. Moreover, these assays are in general insensitive to prothrombotic states. Furthermore, the PT and aPTT assays use the formation of a fibrin clot as the endpoint of the test and this is known to occur when only less than 5% of the total thrombin has been generated.

Rotational thrombelastometry (ROTEM) is a method to measure clotting of whole blood or plasma with or without activators after re-calcification of samples. The primary result of ROTEM is a reaction curve which shows the elasticity over time as the clot forms or dissolves. Measurement parameters include clotting time (CT), clot formation time (CFT), maximum clot firmness (MCF), amplitude 5 min after CT (A5), lysis index after 30 minutes (LI 30), and maximum lysis (ML; percent decrease in amplitude 60 min after MCF). CT is the latency time from adding the start reagent to blood until the clot starts to form. CFT is the time from CT until a clot firmness of 20-millimeter point has been reached. MCF is the greatest vertical amplitude of the trace. Clotting times are typically prolonged by anticoagulants.

The effect of BT-200 on clotting time was evaluated using the ROTEM assay on a ROTEM® delta hemostasis analyzer (Tem Innovations GmbH, Germany). The EXTEM test was performed, which is a screening test for the extrinsic hemostasis system. The results are presented in Table 19. The clotting time was almost identical at all concentrations of BT-200, suggesting that BT-200 has no effect on clotting, consistent with the previous observation. For comparison, pharmacological concentrations of the direct Factor II inhibitor Dabigatran prolong the clotting time 10-fold and that of the direct Factor X inhibitor Rivaroxaban, 4-fold (Schoergenhofer C, et al., *The use of frozen plasma samples in thromboelastometry*. Clin Exp Med, DOI 10.1007/s10238-017-0454-5, the contents of which are incorporated herein by reference in their entirety).

TABLE 19

ROTEM assay

| BT-200 concentration (ug/ml) | CT (s) | CFT (s) | MCF (mm) |
|---|---|---|---|
| 30 | 73 | 540 | 22 |
| 10 | 76 | 325 | 24 |
| 2 | 80 | 493 | 23 |
| 0 | 77 | 360 | 23 |

C. Thrombin Generation Assay

Thrombin generation reflects the plasma's total ability to generate thrombin. The calibrated automated thrombogram (CAT) assay is a routine test used to measure the generation of thrombin. This assay displays the concentration of thrombin in clotting plasma as a function of time by monitoring the splitting of a fluorogenic substrate and comparing it with a constant known thrombin activity in a parallel non-clotting sample. The parameters of the thrombogram include lag time, peak height, endogenous thrombin potential (ETP) (calculated as the area under the curve), maximal rising slop, and time to peak (Hemker H C, et al., *Thrombin generation, a function test of the haemostatic-thrombotic system.* Thromb Haemost. 2006 November; 96(5):553-61, the contents of which are incorporated herein by reference in their entirety). Coagulation inhibitors such as rivaroxaban decrease the ETP, and/or the peak and lengthen the time to peak.

The effect of BT-200 on thrombin generation was assessed via the CAT assay using platelet-poor plasma (PPP) reagents low or high (Thrombinoscope BV, Netherlands). The PPP reagent is used as a trigger that is added to platelet-poor plasma to initiate thrombin generation. Readout was measured on a Fluoroskan ASCENT™ microplate fluorimeter (Thermo Scientific, Waltham, Mass.). Results are presented in Tables 20 and 21. These results confirmed that BT-200 does not alter thrombin generation.

TABLE 20

CAT with PPP reagent (low)

| | BT-200 concentration (ug/ml) | | | | |
| --- | --- | --- | --- | --- | --- |
| | 0 | 3 | 10 | 30 | 100 |
| Lag time (min) | 2.33 | 2.33 | 2 | 2 | 2 |
| ETP (nM × min) | 609 | 599 | 557 | 561 | 553 |
| Peak (nM) | 100 | 98.1 | 94.3 | 98.7 | 98.2 |
| Time to Peak (min) | 5.0 | 5.0 | 5.0 | 4.8 | 4.7 |

TABLE 21

CAT with PPP reagent (high)

| | BT-200 concentration (ug/ml) | | | | |
| --- | --- | --- | --- | --- | --- |
| | 0 | 3 | 10 | 30 | 100 |
| Lag time (min) | 1 | 1 | 1 | 1 | 1 |
| ETP (nM × min) | 577 | 581 | 579 | 570 | 553 |
| Peak (nM) | 138 | 139 | 134 | 139 | 135 |
| Time to Peak (min) | 2.7 | 2.7 | 2.7 | 2.7 | 2.7 |

Example 22. Hematology Test

Hematology parameters including hemoglobin concentration, hematocrit, white blood cell (WBC) and platelet counts were analyzed at pre-dose, 1 week and 2 weeks after BT-200 injection from the same 16 monkeys as in Example 19. The hematology tests were performed with a Sysmex XP-100 3-Part Differential hematology analyzer (Sysmex, Japan). Compared with pre-dose, hemoglobin and hematocrit values decreased slightly, without significant difference. The WBC and platelet counts did not change after injection of BT-200.

Hematology parameters are presented as mean±SD (n=4) in Tables 22-25.

TABLE 22

Hemoglobin concentrations (g/L)

| Sample time | 3 mg/kg I.V. | 3 mg/kg S.C. | 1 mg/kg S.C. | 5 mg/kg S.C. |
| --- | --- | --- | --- | --- |
| Pre-dose | 138.3 ± 11.3 | 138.5 ± 8.4 | 133.8 ± 16.3 | 132.5 ± 12.5 |
| 1 w post dose | 108.3 ± 23.3 | 95.3 ± 32.6 | 116.8 ± 13.5 | 111.0 ± 13.6 |
| 2 w post dose | 113.3 ± 18.9 | 100.5 ± 26.6 | 126.0 ± 4.3 | 114.0 ± 9.8 |

TABLE 23

Hematocrit (%)

| Sample time | 3 mg/kg I.V. | 3 mg/kg S.C. | 1 mg/kg S.C. | 5 mg/kg S.C. |
| --- | --- | --- | --- | --- |
| Pre-dose | 43.7 ± 2.5 | 45.5 ± 1.7 | 43.7 ± 3.8 | 43.0 ± 2.8 |
| 1 w post dose | 36.5 ± 5.2 | 32.0 ± 9.5 | 39.2 ± 3.6 | 37.3 ± 3.0 |
| 2 w post dose | 37.7 ± 4.7 | 34.5 ± 7.7 | 41.6 ± 0.6 | 38.1 ± 3.1 |

TABLE 24

White blood cell numbers (×10$^9$/L)

| Sample time | 3 mg/kg I.V. | 3 mg/kg S.C. | 1 mg/kg S.C. | 5 mg/kg S.C. |
| --- | --- | --- | --- | --- |
| Pre-dose | 15.3 ± 1.2 | 13.7 ± 3.7 | 15.2 ± 2.3 | 15.2 ± 2.3 |
| 1 w post dose | 15.1 ± 3.3 | 13.6 ± 5.9 | 15.0 ± 0.9 | 13.6 ± 2.4 |
| 2 w post dose | 14.5 ± 4.4 | 15.2 ± 2.6 | 17.2 ± 4.1 | 14.0 ± 3.9 |

TABLE 25

Platelets numbers (×10$^9$/L)

| Sample time | 3 mg/kg I.V. | 3 mg/kg S.C. | 1 mg/kg S.C. | 5 mg/kg S.C. |
| --- | --- | --- | --- | --- |
| Pre-dose | 476.8 ± 111.2 | 484.0 ± 79.6 | 473.8 ± 141.1 | 454.5 ± 123.1 |
| 1 w post dose | 555.0 ± 43.7 | 516.8 ± 137.7 | 463.5 ± 50.3 | 512.3 ± 110.6 |
| 2 w post dose | 528.3 ± 47.0 | 503.8 ± 160.9 | 444.8 ± 57.9 | 483.0 ± 93.7 |

Example 23. Exaggerated Pharmacology

Partial deficiency of von Willebrand Factor, as in Type 1 von Willebrand Disease, typically has a very mild clinical phenotype and commonly goes without diagnosis. Indeed, nearly 1% of the general population would be assigned a diagnosis of Type 1 VWD based solely upon the results of laboratory analysis of random blood samples (Nichols W L, et al., *von Willebrand disease (VWD): evidence-based diagnosis and management guidelines, the National Heart, Lung, and Blood Institute (NHLBI) Expert Panel report (USA)*. Haemophilia. 2008 March; 14(2): 171-232, the contents of which are incorporated herein by reference in their entirety). At the other end of the spectrum, severe deficiency of von Willebrand Factor, as in Type 3 von Willebrand Disease, can be associated with a clinical phenotype manifesting as mucocutaneous bleeding, bleeding due to trauma, or local bleeding at sites of dental or surgical procedures. There is a continuum of circulating levels of von Willebrand Factor even within the Type 3 von Willebrand Disease sub-population, and generally among these patients there is a trend for an increased frequency of bleeding symptoms at the lowest VWF levels (Schneppenheim R., et al. *Genetic heterogeneity of severe von Willebrand disease type III in the German population*. Hum Genet. 1994 December; 94(6): 640-52; Zhang Z, Lindstedt M, Blombäck M, Anvret M. *Effects of the mutant von Willebrand factor gene in von Willebrand disease*. Hum Genet. 1995 October; 96(4):388-94; and Nichols W L et al., Haemophilia. 2008 March; 14(2):171-232, the contents of which are each incorporated herein by reference in their entirety).

The genotype-phenotype correlation described by the clinical epidemiology of von Willebrand Disease suggests that administration of a pharmacologic inhibitor of von Willebrand Factor to the normal host would lead to minimal risk of a bleeding phenotype, unless that inhibitor was able to effect complete, sustained inhibition. This prediction was confirmed with the experience of a first-generation aptamer inhibitor of von Willebrand Factor, ARC1779, administered to non-human primates, normal human volunteers, and even patients with thrombocytopenia or patients on anti-coagulants, yet no bleeding manifestations were observed (Gilbert J C, et al., *First-in-human evaluation of anti von Willebrand factor therapeutic aptamer ARC1779 in healthy volunteers*. Circulation. 2007 Dec. 4; 116(23):2678-86; Diener J L, et al., *Inhibition of von Willebrand factor-mediated platelet activation and thrombosis by the anti-von Willebrand factor A1-domain aptamer ARC1779*. J Thromb Haemost. 2009 July; 7(7): 1155-62; Knöbl P, et al., *Anti-von Willebrand factor aptamer ARC1779 for refractory thrombotic thrombocytopenic purpura*. Transfusion. 2009 October; 49(10): 2181-5; Jilma-Stohlawetz P, et al., *A dose ranging phase I/II trial of the von Willebrand factor inhibiting aptamer ARC1779 in patients with congenital thrombotic thrombocytopenic purpura*. Thromb Haemost. 2011 September; 106 (3):539-47, the contents of which are each incorporated herein by reference in their entirety).

BT-200 was engineered to be more potent, longer-acting and to have better subcutaneous bioavailability than predecessor aptamer inhibitors of von Willebrand Factor, such as ARC1779 and ARC15105. These goals appear to have been fully met based upon the findings in PK/PD studies of BT-200 in cynomolgus monkeys. Most of the dosed animals in this study were observed to have mucocutaneous bleeding mostly occurred at the limbs and/or thoracic area beneath the skin. In these animals, a mucocutaneous bleeding typical of Type 3 von Willebrand Disease was observed for the first time, having never been observed even with the highest doses of ARC1779 used non-human primate toxicology studies and ARC15105 used in monkey studies dosed up to 20 mg/kg. This bleeding represents "exaggerated pharmacology," not off-target toxicity, and it was possible to avoid it by simple dose reduction to levels at which von Willebrand Factor function was still inhibited and anti-thrombotic effect would be expected, but at which bleeding was no longer observed.

This was confirmed by the subsequent study when dosing was reduced to 0.3 mg/kg or 0.1 mg/kg in cynomolgus monkeys. Full inhibition of von Willebrand Factor function was still observed using PFA-200 analysis (see Table 26) and no bleeding was observed.

TABLE 26

| | Closure time (s) by PFA-200 | | | |
| --- | --- | --- | --- | --- |
| | 0.3 mg/kg S.C. | | 0.1 mg/kg S.C. | |
| Sample time | Male | Female | Male | Female |
| Pre-dose | 86 | 66 | 70 | 76 |
| 1 h | 112 | 201 | 106 | 103 |
| 8 h | 300 | 300 | 300 | 300 |
| 24 h | 300 | 300 | 253 | 300 |

Example 24. Pharmacokinetics Study

Pharmacokinetics (PK) analysis of BT-200 was performed in plasma samples from the same 16 monkeys as described in Example 19. Blood was sampled pre-dose (−30 min), 1 h, 4 h, 8 h, 24 h, 48 h, 96 h, 168 h, 240 h, and 336 h post-dose. Approximately 0.5 ml whole blood was collected at each time point into tubes containing 1.5% K2-EDTA. Samples were centrifuged at 3000 rpm to obtain plasma. All plasma samples were stored at −80° C. until analysis. Plasma concentration of BT-200 was determined by high-performance liquid chromatography (HPLC) using Agilent 1260 Infinity System (Agilent, Santa Clara, Calif.) with a DNA PAC200 Column, 4*250 mm. PK parameters including half-life ($T_{1/2}$), time of maximum concentration observed ($T_{max}$), initial concentration ($C_0$), maximum concentration ($C_{max}$), AUC up to the last measurable concentration ($AUC_{last}$), AUC from 0 to infinity ($AUC_{inf}$), and bioavailability (F) were determined using Phoenix WinNonlin software (Certara, Princeton, N.J.).

Mean values of the PK parameters are presented in Table 27. The half-life of BT-200 in monkey plasma ($T_{1/2}$) was from 76.4 to 85.7 h. For S.C. dose of 1:3.0:5.0, the exposure vs dose level measured by $C_{max}$ was 1:2.8:5.3, and by $AUC_{inf}$ was 1:2.9:5.5. $T_{max}$ for S.C. administration was from 24 to 42 h. The bioavailability of S.C. administration was from 115% to 133% (the first sample collection time was 1 h for I.V. administration). No significant sex difference was observed. In conclusion, BT-200 has excellent S.C. bioavailability and a long half-life, which make it a great drug candidate.

TABLE 27

| | PK parameters | | | | | |
| --- | --- | --- | --- | --- | --- | --- |
| Treatment | $T_{1/2}$ (h) | $T_{max}$ (h) | $C_0/C_{max}$ (ug/mL) | $AUC_{last}$ (h*ug/mL) | $AUC_{Inf}$ (h*ug/mL) | F (%) |
| 3 mg/kg I.V. | 85.7 | 1 | 74.6 | 4213 | 4473 | NA |
| 1 mg/kg S.C. | 76.4 | 24 | 13.2 | 1602 | 1785 | 120 |
| 3 mg/kg S.C. | 83.9 | 42 | 37.0 | 4798 | 5139 | 115 |
| 5 mg/kg S.C. | 79.3 | 30 | 69.4 | 9294 | 9906 | 133 |

The invention claimed is:

1. A synthetic polynucleotide comprising the sequence of SEQ ID NO: 1.

2. The synthetic polynucleotide of claim 1 comprising a double stranded region, wherein the double stranded region comprises from 6 to 9 base pairs formed by the nucleotides at or near the 3' and 5' termini.

3. The synthetic polynucleotide of claim 1, comprising at least one chemical modification, wherein the chemical modification is made to one of the group selected from the sugar, nucleobase or internucleoside linker of the synthetic polynucleotide.

4. The synthetic polynucleotide of claim 1, wherein each nucleotide comprises at least one chemical modification, wherein the chemical modification is made to one of the group selected from the sugar, nucleobase or internucleoside linker of the synthetic polynucleotide.

5. The synthetic polynucleotide of claim 3, wherein the modification is made to a sugar and the modification consists of a 2' 0-Methyl modification.

6. The synthetic polynucleotide of claim 3, further comprising a 3' and/or 5' terminal cap.

7. The synthetic polynucleotide of claim 6, wherein the 3' and/or 5' terminal cap is an inverted deoxythymidine, or an amino group (NH2).

8. The synthetic polynucleotide of claim 6, wherein the 3' terminal cap comprises an inverted deoxythymidine and the 5' terminal cap comprises an amino group ($NH_2$).

9. The synthetic polynucleotide of claim 8 which is SEQ ID NO: 2.

10. The synthetic polynucleotide of claim 3, comprising a polyethylene glycol conjugate, wherein the polyethylene glycol conjugate is attached to the 5' terminus, or the 3' terminus, of the polynucleotide.

11. The synthetic polynucleotide of claim 10 which is SEQ ID NO: 3.

12. A complementary synthetic polynucleotide comprising the sequence of SEQ ID NO: 4.

13. The complementary synthetic polynucleotide of claim 12, wherein at least one nucleotide comprises a chemical modification.

14. The complementary synthetic polynucleotide of claim 12, wherein each of the nucleotides comprises at least one chemical modification.

15. The complementary synthetic polynucleotide of claim 13, wherein the at least one chemical modification is a 2'-O-methyl modification to a nucleotide sugar.

16. The complementary synthetic polynucleotide of claim 12, which comprises a 3' terminal cap.

17. The complementary synthetic polynucleotide of claim 16, wherein the 3' terminal cap is an inverted deoxythymidine.

18. The complementary synthetic polynucleotide of claim 12 which is SEQ ID NO: 5.

19. A method for treating a disease, disorder or complication relating to Von Willebrand Factor (VWF) in a subject, comprising administering to the subject a medicament comprising a synthetic polynucleotide having a sequence selected from SEQ ID NOs. 1-3 or a complementary synthetic polynucleotide having a sequence selected from SEQ ID NOs. 4-5.

20. The method of claim 19, wherein the disorder is a thrombotic disorder and wherein the thrombotic disorder is ischemic stroke.

21. The method of claim 19, wherein the complication or disorder is a VAD(ventricular assist device) associated complication or disorder, selected from acquired Von Willebrand Syndrome (aVWS), angiodysplasia, occlusive thrombosis, and VAD-associated pump thrombosis.

22. The method of claim 19, wherein the complication or disorder comprises aberrant binding of VWF to erythrocytes.

23. The method of claim 22, wherein the complication or disorder is sickle cell disease.

24. The method of claim 19, wherein the complication or disorder is a complication or disorder associated with gastrointestinal (GI) bleeding associated with angiodysplasia.

25. The method of claim 19, wherein the medicament is for restoring vessel patency in a subject having one or more vessel(s) occluded with at least one occlusive thrombus, wherein the vessel(s) are at least 50% occluded, the method comprising contacting said subject with a VWF protective agent such that vessel patency is restored.

26. A method for disaggregating one or more occlusive thrombi in a subject having at least one vessel that is at least 50% occluded, the method comprising contacting said subject with a VWF protective agent such that the one or more occlusive thrombi are disaggregated, wherein the VWF protective agent comprises a synthetic polynucleotide selected from the group consisting of SEQ ID NOs. 1-3, and/or a complementary synthetic polynucleotide selected from the group consisting of SEQ ID NOs: 4-5.

27. The method of claim 26, wherein the external layer of the occlusive thrombi is disaggregated.

28. The method of claim 26, wherein the occlusive thrombi are formed under conditions of shear rates that are 10,000 $s^{-1}$ or greater.

29. The method of claim 26, wherein the occlusive thrombi are resistant to fibrinolysis and/or antithrombotic agents.

30. The method of claim 26, wherein the subject has a condition selected from acute coronary syndrome, acute occlusion thrombosis, and ischemic stroke.

31. A method for preventing platelet aggregation in a subject having a thrombotic disorder or complication relating to Von Willebrand Factor (VWF), the method comprising administering to the subject a composition comprising a synthetic polynucleotide selected from the group consisting of SEQ ID NOs. 1-3, and/or a complementary synthetic polynucleotide selected from the group consisting of SEQ ID NOs 4-5.

32. The method of claim 31, wherein the synthetic polynucleotide is administered via intravenous injection, or subcutaneous injection.

33. The method of claim 32, wherein the synthetic polynucleotide is administered via subcutaneous injection by which the bioavailability of subcutaneous injection is at least 85% relative to intravenous injection.

34. The method of claim 32, wherein the synthetic polynucleotide is administered at a dose of from about 0.01 mg/kg to about 0.5 mg/kg of the subject body weight.

35. The method of claim 31, wherein the synthetic polynucleotide has a plasma half-life of from about 70 hours to about 100 hours.

36. The method of claim 31, wherein the thrombotic disorder or complication is myocardial infarction, or ischemic stroke.

37. The method of claim 19, wherein the complication or disorder is a central nervous system (CNS) thrombosis associated with severe and/or cerebral malaria.

38. The method of claim 24 wherein the disorder is gastrointestinal (GI) bleeding associated with Heyde's Syndrome.

* * * * *